United States Patent [19]
Sim et al.

[11] Patent Number: 5,849,306
[45] Date of Patent: Dec. 15, 1998

[54] **BINDING DOMAINS FROM *PLASMODIUM VIVAX* AND *PLASMODIUM FALCIPARUM* ERYTHROCYTE BINDING PROTEINS**

[75] Inventors: Kim Lee Sim, Gaithersburg, Md.; Chetan Chitnis, Washington, D.C.; Louis H. Miller, Bethesda, Md.; David S. Peterson, Rockville, Md.; Xin-Zhuan Su, Rockville, Md.; Thomas E. Wellems, Rockville, Md.

[73] Assignee: The United States of America as represented by the Department of Health and Human Services, Washington, D.C.

[21] Appl. No.: 568,459

[22] Filed: Dec. 7, 1995

Related U.S. Application Data

[63] Continuation of Ser. No. 119,677, Sep. 10, 1993, abandoned.
[51] Int. Cl.$^6$ .................... A61K 39/015; C07K 14/445
[52] U.S. Cl. .................... 424/268.1; 424/185.1; 424/192.1; 424/272.1; 435/69.3; 435/69.7; 530/350; 530/395
[58] Field of Search ............ 424/185.1, 268.1, 424/272.1; 530/350, 395; 435/69.3

[56] References Cited

U.S. PATENT DOCUMENTS 5,198,347 3/1993 Miller et al. ............ 435/69.1

FOREIGN PATENT DOCUMENTS

WO 9507353 3/1995 WIPO.

OTHER PUBLICATIONS

Borst, et al., Antigenic Variation in Malaria, *Cell* 82:1–4, Jul. 14, 1995.

Chitnis, Chetan E., and Miller, Louis H., Identification of the Erythrocyte Binding Domains . . . , *J. Exper. Med.* 180:497–506, Aug. 1994.

Sim, et al., Receptor and Ligand Domains for Invasion of Erythrocytes by *Plasmodium Falciparum*, *Science* 264:1941–1944, Jun. 24 1994.

Su, et al., The Large Diverse gene Family var Encodes Proteins Involved in Cytoadherence and Antigenic . . . , *Cell* 82:89–100, Jul. 14, 1995.

Barnwell, J.W., et al., "In vitro Evaluation of the Role of the duffy Blood Group in Erythrocyte Invasion by *Plasmodium Vivax,*" *J. Exp. Med.*, 169:1795–1802 (May 1989).

Sim, B.K.L., et al., "Primary Structure of the 175K *Plasmodium falciparum* Erythrocyte Binding Antigen and Identification of a Peptide Which Elicits Antibodies That Inhibit Malaria Merozite Invasion", *J. of Cell Biology*, 111:1877–1884 (Nov. 1990).

Haynes, J.D., et al., "Receptor–Like Specificity of a *Plasmodium Knowlesi* Malarial Protein the Binds to Duffy Antigen Ligands on Erythrocytes," *J. Exp. Med.*, 167:1873–1881 (Jun. 1988).

Miller, L.H., et al., "Identification of *Plasmodium knowlesi* erythrocyte binding proteins," *Molecular and Biochemical Parasitology*, 31:217–222 (1988).

Wertheimer, S.P., et al., "*Plasmodium vivax* Interaction with the Human Duffy Blood Group glycoprotein: Identification of a Parasite Receptor–like Protein," *Experimental Parasitology*, 69:340–350 (1989).

Adams, J.H., et al., "A family of erythrocyte binding proteins of malaria parasites," *Proc. Natl. Acad. Sci. USA*, 89:7085–7089 (Aug. 1992).

Dalton, J.P., et al., "Blocking the receptor–mediated invasion of erythrocytes by *Plasmodium knowlesi* malaria with sulfated polysaccharides and glycosaminoglycans," *Eur. J. Biochem.*, 195:789–794 (1991).

Orlandi, P.A., et al., "Characterization of the 175–kilodalton erythrocyte binding antigen of *Plasmodium falciparum,*" *Molecular and Biochemical Parasitology*, 40:285–294 (1990).

Holt, E.H., et al., "Erythrocyte Invasion by two *Plasmodium Falciparum* Isolates Differing in Sialic Acid Dependency in the Presence of Glycophorin A Antibodies," *Am. J. Trop. Med. Hyg.*, 40(3):245–251 (Mar. 1989).

Perkins, M.E., et al., "Sialic Acid–Dependent Binding of *Plasmodium falciparum* Merozoite Surface Antigen, Pf200, to Human Erythrocytes," *J. of Immunology*, 141(9):3190–3196 (Nov. 1, 1988).

*Primary Examiner*—Thomas M. Cunningham
*Attorney, Agent, or Firm*—Knobbe, Martens, Olson & Bear, LLP

[57] ABSTRACT

The present invention provides isolated polypeptides useful in the treatment and prevention of malaria caused by *Plasmodium falciparum* or *P. vivax*. In particular, the polypeptides are derived from the binding domains of the proteins in the EBL family as well as the sialic acid binding protein (SABP) on *P. falciparum* merozoites. The polypeptides may also be derived from the Duffy antigen binding protein (DABP) on *P. vivax* merozoites.

12 Claims, 4 Drawing Sheets

```
Family 1   DABP      C-X₁₂-C-X₅--VCIPDRRYQLCMKEL-X₄₇-  DFCKDIRWSLGDFGDIIMGTDMEGIGYSK-X₁₁-
           SABP F1   C-X₁₀-C-X₉--VCIPDRRIQLCIVNL-X₃₆-  KFCNDLKNSFLDYGHLAMGNDMDFGGYST-X₁₇-
           SABP F2   C-X₁₃-C-X₁₀-VCVPPRRQELCLGNI-X₃₆-  EVCKIINKTEADIRDIIGGTDYWNDLSNR-X₁₅-
           EBL-e1    C-X₁₂-C-X₁₁-VCGPPRRQQLCLGYI-X₃₆-  KICNAILGSYADIGDIVRGLDVWRDINTN-X₁₇-

Family 2   EBL-e2    ----------ACAPYRRLHLCDYNL-X₄₃-    QLCTVLARSFADIGDIVRGKDLYLGYDNK-X₃₇-
           Proj3 F1  C-X₁₅-C-X₁₅-ACAPYRRLHVCDQNL-X₄₅-  QICTMLARSFADIGDIVRGRDLYLGNPQE-X₃₀-
           Proj3 F2  C-X₁₇-C-X₃₁-VFLPPRREHMCTSNL-X₅₅-  AMCRAVRYSFADLGDIIRGRDMWDEDKSS-X₃₂-
           Proj3 F3  C-X₁₀-C-X₁₀-ACMPPRRQKLCLYYI-X₅₂-  QFLRSMMYTEGDYRDICLNTDISKKQNDV-X₁₅-
           E31a      C-X₁₀-C-X₁₁-ACIPPRRQKLCLHYL-X₅₁-  DFKRQMFYTEADYRDICLGTDISSKKDTS-X₁₅-

Family 1   DABP      TDEKAQQRRKQWMNESKAQIWTAMMYSV-X₁₁-C-X₈-- ePQIYRWIREWGRDYVSELPTEVQKLKEKC--X₁₁--C-X₁--
Cont'd     SABP F1   SEHKIKNFRKEWWNEFREKLWEAMLSEH-X₆---C-X₆-- eLQITQWIKEWHGEFLLERDNRSKLPKSKC--X₈---C-X₀--
           SABP F2   NKKNDKLFRDEWWKVIKKDVWNVISWVF-X₅---C-X₇-- IPQFFRWFSEWGDDYCQDKTKMIETLKVEC--X₄---C-X₁--
           EBL-e1    KKQNDNNERNKWWEKQRNLIWSSMVKHI-X₅---C-X₈-- IPQFLRWLKEWGDEFCEEMGTEVKQLEKIC--X₄---C-X₁--
```

*FIG. 1A*

| FIG.1A |
|--------|
| FIG.1B |

*FIG. 1*

| | | | |
|---|---|---|---|
| Family 2 Cont'd | EBL-e2 | KGGDFFQLREDWWTSNRETVWKALICHA-$X_{11}$-C-$X_{23}$-VPQYLRWFEEWAEDFCRKKKKLENLQKQC--$X_6$----C-$X_{15}$-- |
| | Proj3 F1 | NDPEFFKLREDWWTANRETVWKAITCNA-$X_9$--C-$X_{23}$-VPQYLRWFEEWAEDFCRKKNKKIKDVKRNC--$X_{12}$--C-$X_{22}$-- |
| | Proj3 F2 | KKPAYKKLRADWWEANRHQVWRAMKCAT-$X_4$--C-$X_8$--IPQRLRWMTEWAEWYCKAQSQEYDKLKKIC--$X_{11}$--C-$X_6$-- |
| | Proj3 F3 | SKSPSGLSRQEWWKTNGPEIWKGMLCAL-$X_{37}$----------KPQFLRWMIEWGEEFCAERQKKENIIKDAC--$X_8$---C-$X_3$-- |
| | E31a | KISNSIRYRKSWWETNGPVIWEGMLCAL-$X_{42}$----------RPQFLRWLTEWGENFCKEQKKEYKVLLAKC--$X_{11}$--C-$X_3$-- |
| Family 1 Cont'd | DABP | VPPCQNACKSYDQ    WITRKKN-$X_{56}$---------CX---C |
| | SABP F1 | EKECIDPCMKYRD    WIIRSKF-$X_{41}$-C-$X_7$---------CX---C |
| | SABP F2 | DDNCKSKCNSYKE    WISKKKK-$X_{36}$-C-$X_{20}$--------CXX-C |
| | EBL-e1 | EKKCKNACSSYEK    WIKERKN-$X_{38}$-C-$X_{19}$--------CXX-C |
| Family 2 Cont'd | EBL-e2 | CTNCSVWCRMYET    WIDNQKK-$X_{68}$-C-$X_{30}$--------CXX-C |
| | Proj3 F1 | CISCLYACNPYVD    WIDNQKK-$X_{69}$-C-$X_{40}$--------CXX-C |
| | Proj3 F2 | CGKCKAACDKYKEEIEKWNEQWRK-$X_{73}$-C-$X_6$-C-$X_{30}$-CXX-C |
| | Proj3 F3 | KHRCNQACRAYQE    YVENKKK-$X_{43}$-C-$X_4$--------CX--C |
| | E31a | CVACKDQCKQYHS    WIGIWID-$X_{42}$-C-$X_8$--------CXXXC |

FIG. 1B

Consensus amino acid sequences and the synthetic oligonucleotide primers designed from them.

I. UNIEBP5 and 5A:   PRRQK/ELC  (SEQ ID NO: 22)

UNIEBP5, for A+T biased condon usage:
CC(A/G)-AG(G/A)-AG(G/A)-CAA-(G/A)AA-(C/T)TA-TG  (SEQ ID NO: 23)

UNIEBP5A, for G+C biased codon usage:
CC(C/G)-(C/A)G(C/G)-(C/A)G(C/G)-CAG-CAG-(C/T)T(C/G)-TG  (SEQ ID NO: 24)

II. UNIEBP5 B and C:   FADI/YG/RDI  (SEQ ID NO: 25)

UNIEBP5B, for A+T biased codon usage:
TTT-GC(A/T)-GAT-(A/T)(A/T)(A/T)-(G/C)G(A/T)-GAT-AT  (SEQ ID NO: 26)

UNIEBP5C, for G+C biased codon usage:
TTC-GC(G/C)-GAT-(A/T)(A/T)C-(G/C)G(G/C)-GAC-AT  (SEQ ID NO: 27)

III. UNIEBP3 and 3A:   PQFL/FRW  (SEQ ID NO: 28)

UNIEBP3, for A+T biased codon usage:
CCA-(A/T)C(T/G)-(T/G)A(A/G)-(A/G)AA-TTG-(A/T)GG  (SEQ ID NO: 29)

UNIEBP3A, for G+C biased codon usage:
CCA-(C/G)C(G/T)-G(A/T)A-GA(A/T)-CTG-(C/G)GG  (SEQ ID NO: 30)

IV. UNIEBP3 and C:   EWGD/ED/EY/FC  (SEQ ID NO: 31)

UNIEBP3B, for A+T biased codon usage:
CA-A(A/T)A-(A/T)TC-(A/T)TC-(A/T)CC-CCA-TTC  (SEQ ID NO: 32)

UNIEBP3C, for G+C biased codon usage:
CA-G(A/T)A-(G/C)TC-(G/C)TC-(G/C)CC-CCA-CTC  (SEQ ID NO: 33)

*FIG. 3*

SEQUENCE LISTING ( 1 ) GENERAL INFORMATION:

( i i i ) NUMBER OF SEQUENCES: 37

( 2 ) INFORMATION FOR SEQ ID NO:1:

( i ) SEQUENCE CHARACTERISTICS:
        ( A ) LENGTH: 4084 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Plasmodium vivax ( x i ) SEQUENCE DESCRIPTION: SEQ ID NO:1:

```
AAGCTTTTAA  AAATAGCAAC  AAAATTTCGA  AACATTGCCA  CAAAAATTTT  ATGTTTTACA       60
TATATTTAGA  TTCATACAAT  TTAGGTGTAC  CCTGTTTTTT  GATATATGCG  CTTAAATTTT      120
TTTTTCGCTC  ATATGTTTAG  TTATATGTGT  AGAACAACTT  GCTGAATAAA  TTACGTACAC      180
TTTCTGTTCT  GAATAATATT  ACCACATACA  TTTAATTTTA  AATACTATGA  AAGGAAAAAA     240
CCGCTCTTTA  TTTGTTCTCC  TAGTTTTATT  ATTGTTACAC  AAGGTATCAT  ATAAGGATGA      300
TTTTTCTATC  ACACTAATAA  ATTATCATGA  AGGAAAAAAA  TATTTAATTA  TACTAAAAAG      360
AAAATTAGAA  AAAGCTAATA  ATCGTGATGT  TTGCAATTTT  TTTCTTCATT  TCTCTCAGGT      420
AAATAATGTA  TTATTAGAAC  GAACAATTGA  AACCCTTCTA  GAATGCAAAA  ATGAATATGT      480
GAAAGGTGAA  AATGGTTATA  AATTAGCTAA  AGGACACCAC  TGTGTTGAGG  AAGATAACTT      540
AGAACGATGG  TTACAAGGAA  CCAATGAAAG  AAGAAGTGAG  GAAAATATAA  AATATAAATA      600
TGGAGTAACG  GAACTAAAAA  TAAAGTATGC  GCAAATGAAT  GGAAAAAGAA  GCAGCCGCAT      660
TTTGAAGGAA  TCAATTTACG  GGGCGCATAA  CTTTGGAGGC  AACAGTTACA  TGGAGGGAAA      720
AGATGGAGGA  GATAAAACTG  GGGAGGAAAA  AGATGGAGAA  CATAAAACTG  ATAGTAAAAC      780
TGATAACGGG  AAAGGTGCAA  ACAATTTGGT  AATGTTAGAT  TATGAGACAT  CTAGCAATGG      840
CCAGCCAGCG  GGAACCCTTG  ATAATGTTCT  TGAATTTGTG  ACTGGGCATG  AGGGAAATTC      900
TCGTAAAAAT  TCCTCGAATG  GTGGCAATCC  TTACGATATT  GATCATAAGA  AAACGATCTC      960
TAGTGCTATT  ATAAATCATG  CTTTTCTTCA  AAATACTGTA  ATGAAAAACT  GTAATTATAA     1020
GAGAAAACGT  CGGGAAAGAG  ATTGGGACTG  TAACACTAAG  AAGGATGTTT  GTATACCAGA     1080
TCGAAGATAT  CAATTATGTA  TGAAGGAACT  TACGAATTTG  GTAAATAATA  CAGACACAAA     1140
TTTTCATAGG  GATATAACAT  TTCGAAAATT  ATATTTGAAA  AGGAAACTTA  TTTATGATGC     1200
TGCAGTAGAG  GGCGATTTAT  TACTTAAGTT  GAATAACTAC  AGATATAACA  AAGACTTTTG     1260
CAAGGATATA  AGATGGAGTT  TGGGAGATTT  TGGAGATATA  ATTATGGGAA  CGGATATGGA     1320
```

-continued

| | | | | | | |
|---|---|---|---|---|---|---|
| AGGCATCGGA | TATTCCAAAG | TAGTGGAAAA | TAATTTGCGC | AGCATCTTTG | GAACTGATGA | 1380 |
| AAAGGCCCAA | CAGCGTCGTA | AACAGTGGTG | GAATGAATCT | AAAGCACAAA | TTTGGACAGC | 1440 |
| AATGATGTAC | TCAGTTAAAA | AAAGATTAAA | GGGGAATTTT | ATATGGATTT | GTAAATTAAA | 1500 |
| TGTTGCGGTA | AATATAGAAC | CGCAGATATA | TAGATGGATT | CGAGAATGGG | GAAGGGATTA | 1560 |
| CGTGTCAGAA | TTGCCCACAG | AAGTGCAAAA | ACTGAAAGAA | AATGTGATG | GAAAAATCAA | 1620 |
| TTATACTGAT | AAAAAAGTAT | GTAAGGTACC | ACCATGTCAA | AATGCGTGTA | AATCATATGA | 1680 |
| TCAATGGATA | ACCAGAAAAA | AAAATCAATG | GGATGTTCTG | TCAAATAAAT | TCATAAGTGT | 1740 |
| AAAAACGCA | GAAAAGGTTC | AGACGGCAGG | TATCGTAACT | CCTTATGATA | TACTAAAACA | 1800 |
| GGAGTTAGAT | GAATTTAACG | AGGTGGCTTT | TGAGAATGAA | ATTAACAAAC | GTGATGGTGC | 1860 |
| ATATATTGAG | TTATGCGTTT | GTTCCGTTGA | AGAGGCTAAA | AAAAATACTC | AGGAAGTTGT | 1920 |
| GACAAATGTG | GACAATGCTG | CTAAATCTCA | GGCCACCAAT | TCAAATCCGA | TAAGTCAGCC | 1980 |
| TGTAGATAGT | AGTAAAGCGG | AGAAGGTTCC | AGGAGATTCT | ACGCATGGAA | ATGTTAACAG | 2040 |
| TGGCCAAGAT | AGTTCTACCA | CAGGTAAAGC | TGTTACGGGG | GATGGTCAAA | ATGGAAATCA | 2100 |
| GACACCTGCA | GAAAGCGATG | TACAGCGAAG | TGATATTGCC | GAAAGTGTAA | GTGCTAAAAA | 2160 |
| TGTTGATCCG | CAGAAATCTG | TAAGTAAAAG | AAGTGACGAC | ACTGCAAGCG | TTACAGGTAT | 2220 |
| TGCCGAAGCT | GGAAAGGAAA | ACTTAGGCGC | ATCAAATAGT | CGACCTTCTG | AGTCCACCGT | 2280 |
| TGAAGCAAAT | AGCCCAGGTG | ATGATACTGT | GAACAGTGCA | TCTATACCTG | TAGTGAGTGG | 2340 |
| TGAAAACCCA | TTGGTAACCC | CCTATAATGG | TTTGAGGCAT | TCGAAAGACA | ATAGTGATAG | 2400 |
| CGATGGACCT | GCGGAATCAA | TGGCGAATCC | TGATTCAAAT | AGTAAAGGTG | AGACGGGAAA | 2460 |
| GGGGCAAGAT | AATGATATGG | CGAAGGCTAC | TAAAGATAGT | AGTAATAGTT | CAGATGGTAC | 2520 |
| CAGCTCTGCT | ACGGGTGATA | CTACTGATGC | AGTTGATAGG | GAAATTAATA | AAGGTGTTCC | 2580 |
| TGAGGATAGG | GATAAAACTG | TAGGAAGTAA | AGATGGAGGG | GGGAAGATA | ACTCTGCAAA | 2640 |
| TAAGGATGCA | GCGACTGTAG | TTGGTGAGGA | TAGAATTCGT | GAGAACAGCG | CTGGTGGTAG | 2700 |
| CACTAATGAT | AGATCAAAAA | ATGACACGGA | AAAGAACGGG | GCCTCTACCC | CTGACAGTAA | 2760 |
| ACAAAGTGAG | GATGCAACTG | CGCTAAGTAA | AACCGAAAGT | TTAGAATCAA | CAGAAAGTGG | 2820 |
| AGATAGAACT | ACTAATGATA | CAACTAACAG | TTTAGAAAAT | AAAAATGGAG | GAAAAGAAAA | 2880 |
| GGATTTACAA | AAGCATGATT | TTAAAAGTAA | TGATACGCCG | AATGAAGAAC | CAAATTCTGA | 2940 |
| TCAAACTACA | GATGCAGAAG | GACATGACAG | GGATAGCATC | AAAAATGATA | AAGCAGAAAG | 3000 |
| GAGAAAGCAT | ATGAATAAAG | ATACTTTTAC | GAAAAATACA | AATAGTCACC | ATTTAAATAG | 3060 |
| TAATAATAAT | TTGAGTAATG | GAAAATTAGA | TATAAAAGAA | TACAAATACA | GAGATGTCAA | 3120 |
| AGCAACAAGG | GAAGATATTA | TATTAATGTC | TTCAGTACGC | AAGTGCAACA | ATAATATTTC | 3180 |
| TTTAGAGTAC | TGTAACTCTG | TAGAGGACAA | AATATCATCG | AATACTTGTT | CTAGAGAGAA | 3240 |
| AAGTAAAAAT | TTATGTTGCT | CAATATCGGA | TTTTTGTTTG | AACTATTTTG | ACGTGTATTC | 3300 |
| TTATGAGTAT | CTTAGCTGCA | TGAAAAGGA | ATTTGAAGAT | CCATCCTACA | AGTGCTTTAC | 3360 |
| GAAAGGGGC | TTTAAAGGTA | TGCAGAAAAA | GATGCTGAAT | AGAGAAAGGT | GTTGAGTAAA | 3420 |
| TTAAAAGGA | ATTAATTTTA | GGAATGTTAT | AAACATTTTT | GTACCCAAAA | TTCTTTTTGC | 3480 |
| AGACAAGACT | TACTTTGCCG | CGGCGGGAGC | GTTGCTGATA | CTGCTGTTGT | TAATTGCTTC | 3540 |
| AAGGAAGATG | ATCAAAAATG | AGTAACCAGA | AAATAAAATA | AAATAACATA | AAATAAAATA | 3600 |
| AAAACTAGAA | TAACAATTAA | AATAAAATAA | AATGAGAAAT | GCCTGTTAAT | GCACAGTTAA | 3660 |
| TTCTAACGAT | TCCATTTGTG | AAGTTTTAAA | GAGAGCACAA | ATGCATAGTC | ATTATGTCCA | 3720 |

-continued

```
TGCATATATA CACATATATG TACGTATATA TAATAAACGC ACACTTTCTT GTTCGTACAG    3780

TTCTGAAGAA GCTACATTTA ATGAGTTTGA AGAATACTGT GATAATATTC ACAGAATCCC    3840

TCTGATGCCT AACAGTAATT CAAATTTCAA GAGCAAAATT CCATTTAAAA AGAAATGTTA    3900

CATCATTTTG CGTTTTTCTT TTTTTCTTTT TTTTTCTTT TTTAGATATT GAACACATGC    3960

AGCCATCAAC CCCCCTGGAT TATTCATGAT GCTACTTTGG TAAGTAAAAG CAATTCTGAT    4020

TGTAGTGCTG ATGTAATTTT AGTCATTTTG CTTGCTGCAA TAAACGAGAA AATATATCAA    4080

GCTT                                                                  4084
```

( 2 ) INFORMATION FOR SEQ ID NO:2:

( i ) SEQUENCE CHARACTERISTICS:
        ( A ) LENGTH: 1115 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: Plasmodium vivax ( x i ) SEQUENCE DESCRIPTION: SEQ ID NO:2:

```
Met Lys Gly Lys Asn Arg Ser Leu Phe Val Leu Leu Val Leu Leu Leu
  1               5                  10                  15

Leu His Lys Val Ser Tyr Lys Asp Asp Phe Ser Ile Thr Leu Ile Asn
             20                  25                  30

Tyr His Glu Gly Lys Lys Tyr Leu Ile Ile Leu Lys Arg Lys Leu Glu
         35                  40                  45

Lys Ala Asn Asn Arg Asp Val Cys Asn Phe Phe Leu His Phe Ser Gln
     50                  55                  60

Val Asn Asn Val Leu Leu Glu Arg Thr Ile Glu Thr Leu Leu Glu Cys
 65                  70                  75                  80

Lys Asn Glu Tyr Val Lys Gly Glu Asn Gly Tyr Lys Leu Ala Lys Gly
                 85                  90                  95

His His Cys Val Glu Glu Asp Asn Leu Glu Arg Trp Leu Gln Gly Thr
            100                 105                 110

Asn Glu Arg Arg Ser Glu Glu Asn Ile Lys Tyr Lys Tyr Gly Val Thr
        115                 120                 125

Glu Leu Lys Ile Lys Tyr Ala Gln Met Asn Gly Lys Arg Ser Ser Arg
    130                 135                 140

Ile Leu Lys Glu Ser Ile Tyr Gly Ala His Asn Phe Gly Gly Asn Ser
145                 150                 155                 160

Tyr Met Glu Gly Lys Asp Gly Gly Asp Lys Thr Gly Glu Glu Lys Asp
                165                 170                 175

Gly Glu His Lys Thr Asp Ser Lys Thr Asp Asn Gly Lys Gly Ala Asn
            180                 185                 190

Asn Leu Val Met Leu Asp Tyr Glu Thr Ser Ser Asn Gly Gln Pro Ala
        195                 200                 205

Gly Thr Leu Asp Asn Val Leu Glu Phe Val Thr Gly His Glu Gly Asn
    210                 215                 220

Ser Arg Lys Asn Ser Ser Asn Gly Gly Asn Pro Tyr Asp Ile Asp His
225                 230                 235                 240

Lys Lys Thr Ile Ser Ser Ala Ile Ile Asn His Ala Phe Leu Gln Asn
                245                 250                 255
```

```
Thr Val Met Lys Asn Cys Asn Tyr Lys Arg Lys Arg Arg Glu Arg Asp
        260                 265                 270
Trp Asp Cys Asn Thr Lys Lys Asp Val Cys Ile Pro Asp Arg Arg Tyr
        275                 280                 285
Gln Leu Cys Met Lys Glu Leu Thr Asn Leu Val Asn Thr Asp Thr
    290                 295                 300
Asn Phe His Arg Asp Ile Thr Phe Arg Lys Leu Tyr Leu Lys Arg Lys
305                 310                 315                 320
Leu Ile Tyr Asp Ala Ala Val Glu Gly Asp Leu Leu Lys Leu Asn
                    325                 330                 335
Asn Tyr Arg Tyr Asn Lys Asp Phe Cys Lys Asp Ile Arg Trp Ser Leu
                340                 345                 350
Gly Asp Phe Gly Asp Ile Ile Met Gly Thr Asp Met Glu Gly Ile Gly
            355                 360                 365
Tyr Ser Lys Val Val Glu Asn Asn Leu Arg Ser Ile Phe Gly Thr Asp
        370                 375                 380
Glu Lys Ala Gln Gln Arg Arg Lys Gln Trp Trp Asn Glu Ser Lys Ala
385                 390                 395                 400
Gln Ile Trp Thr Ala Met Met Tyr Ser Val Lys Lys Arg Leu Lys Gly
                405                 410                 415
Asn Phe Ile Trp Ile Cys Lys Leu Asn Val Ala Val Asn Ile Glu Pro
                420                 425                 430
Gln Ile Tyr Arg Trp Ile Arg Glu Trp Gly Arg Asp Tyr Val Ser Glu
            435                 440                 445
Leu Pro Thr Glu Val Gln Lys Leu Lys Glu Lys Cys Asp Gly Lys Ile
    450                 455                 460
Asn Tyr Thr Asp Lys Lys Val Cys Lys Val Pro Pro Cys Gln Asn Ala
465                 470                 475                 480
Cys Lys Ser Tyr Asp Gln Trp Ile Thr Arg Lys Lys Asn Gln Trp Asp
                485                 490                 495
Val Leu Ser Asn Lys Phe Ile Ser Val Lys Asn Ala Glu Lys Val Gln
            500                 505                 510
Thr Ala Gly Ile Val Thr Pro Tyr Asp Ile Leu Lys Gln Glu Leu Asp
        515                 520                 525
Glu Phe Asn Glu Val Ala Phe Glu Asn Glu Ile Asn Lys Arg Asp Gly
    530                 535                 540
Ala Tyr Ile Glu Leu Cys Val Cys Ser Val Glu Glu Ala Lys Lys Asn
545                 550                 555                 560
Thr Gln Glu Val Val Thr Asn Val Asp Asn Ala Ala Lys Ser Gln Ala
                565                 570                 575
Thr Asn Ser Asn Pro Ile Ser Gln Pro Val Asp Ser Ser Lys Ala Glu
            580                 585                 590
Lys Val Pro Gly Asp Ser Thr His Gly Asn Val Asn Ser Gly Gln Asp
        595                 600                 605
Ser Ser Thr Thr Gly Lys Ala Val Thr Gly Asp Gly Gln Asn Gly Asn
    610                 615                 620
Gln Thr Pro Ala Glu Ser Asp Val Gln Arg Ser Asp Ile Ala Glu Ser
625                 630                 635                 640
Val Ser Ala Lys Asn Val Asp Pro Gln Lys Ser Val Ser Lys Arg Ser
                645                 650                 655
Asp Asp Thr Ala Ser Val Thr Gly Ile Ala Glu Ala Gly Lys Glu Asn
            660                 665                 670
Leu Gly Ala Ser Asn Ser Arg Pro Ser Glu Ser Thr Val Glu Ala Asn
        675                 680                 685
```

-continued

```
Ser  Pro  Gly  Asp  Asp  Thr  Val  Asn  Ser  Ala  Ser  Ile  Pro  Val  Val  Ser
     690                 695                 700

Gly  Glu  Asn  Pro  Leu  Val  Thr  Pro  Tyr  Asn  Gly  Leu  Arg  His  Ser  Lys
705                 710                 715                           720

Asp  Asn  Ser  Asp  Ser  Asp  Gly  Pro  Ala  Glu  Ser  Met  Ala  Asn  Pro  Asp
               725                 730                      735

Ser  Asn  Ser  Lys  Gly  Glu  Thr  Gly  Lys  Gly  Gln  Asp  Asn  Asp  Met  Ala
               740                 745                      750

Lys  Ala  Thr  Lys  Asp  Ser  Ser  Asn  Ser  Ser  Asp  Gly  Thr  Ser  Ser  Ala
          755                 760                 765

Thr  Gly  Asp  Thr  Thr  Asp  Ala  Val  Asp  Arg  Glu  Ile  Asn  Lys  Gly  Val
     770                 775                 780

Pro  Glu  Asp  Arg  Asp  Lys  Thr  Val  Gly  Ser  Lys  Asp  Gly  Gly  Gly  Glu
785                 790                 795                                800

Asp  Asn  Ser  Ala  Asn  Lys  Asp  Ala  Ala  Thr  Val  Val  Gly  Glu  Asp  Arg
               805                 810                      815

Ile  Arg  Glu  Asn  Ser  Ala  Gly  Gly  Ser  Thr  Asn  Asp  Arg  Ser  Lys  Asn
               820                 825                      830

Asp  Thr  Glu  Lys  Asn  Gly  Ala  Ser  Thr  Pro  Asp  Ser  Lys  Gln  Ser  Glu
          835                 840                 845

Asp  Ala  Thr  Ala  Leu  Ser  Lys  Thr  Glu  Ser  Leu  Glu  Ser  Thr  Glu  Ser
     850                 855                 860

Gly  Asp  Arg  Thr  Thr  Asn  Asp  Thr  Thr  Asn  Ser  Leu  Glu  Asn  Lys  Asn
865                 870                 875                                880

Gly  Gly  Lys  Glu  Lys  Asp  Leu  Gln  Lys  His  Asp  Phe  Lys  Ser  Asn  Asp
               885                 890                      895

Thr  Pro  Asn  Glu  Glu  Pro  Asn  Ser  Asp  Gln  Thr  Thr  Asp  Ala  Glu  Gly
               900                 905                      910

His  Asp  Arg  Asp  Ser  Ile  Lys  Asn  Asp  Lys  Ala  Glu  Arg  Arg  Lys  His
          915                 920                 925

Met  Asn  Lys  Asp  Thr  Phe  Thr  Lys  Asn  Thr  Asn  Ser  His  His  Leu  Asn
     930                 935                 940

Ser  Asn  Asn  Asn  Leu  Ser  Asn  Gly  Lys  Leu  Asp  Ile  Lys  Glu  Tyr  Lys
945                 950                 955                                960

Tyr  Arg  Asp  Val  Lys  Ala  Thr  Arg  Glu  Asp  Ile  Ile  Leu  Met  Ser  Ser
               965                 970                      975

Val  Arg  Lys  Cys  Asn  Asn  Asn  Ile  Ser  Leu  Glu  Tyr  Cys  Asn  Ser  Val
               980                 985                      990

Glu  Asp  Lys  Ile  Ser  Ser  Asn  Thr  Cys  Ser  Arg  Glu  Lys  Ser  Lys  Asn
               995                 1000                     1005

Leu  Cys  Cys  Ser  Ile  Ser  Asp  Phe  Cys  Leu  Asn  Tyr  Phe  Asp  Val  Tyr
     1010                1015                1020

Ser  Tyr  Glu  Tyr  Leu  Ser  Cys  Met  Lys  Lys  Glu  Phe  Glu  Asp  Pro  Ser
1025                1030                1035                               1040

Tyr  Lys  Cys  Phe  Thr  Lys  Gly  Gly  Phe  Lys  Ile  Asp  Lys  Thr  Tyr  Phe
               1045                1050                     1055

Ala  Ala  Ala  Gly  Ala  Leu  Leu  Ile  Leu  Leu  Leu  Ile  Ala  Ser  Arg  Lys
               1060                1065                     1070

Met  Ile  Lys  Asn  Asp  Ser  Glu  Glu  Ala  Thr  Phe  Asn  Glu  Phe  Glu  Glu
               1075                1080                     1085

Tyr  Cys  Asp  Asn  Ile  His  Arg  Ile  Pro  Leu  Met  Pro  Asn  Asn  Ile  Glu
               1090                1095                     1100

His  Met  Gln  Pro  Ser  Thr  Pro  Leu  Asp  Tyr  Ser
```

| 1105 | 1110 | 1115 |

( 2 ) INFORMATION FOR SEQ ID NO:3:

( i ) SEQUENCE CHARACTERISTICS:
        ( A ) LENGTH: 4507 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Plasmodium falciparum ( x i ) SEQUENCE DESCRIPTION: SEQ ID NO:3:

```
TATATATATA  TATATATATA  GATAATAACA  TATAAATATA  TTCAATGTGC  ATACAATGAA     60
ATGTAATATT  AGTATATATT  TTTTTGCTTC  CTTCTTTGTG  TTATATTTTG  CAAAAGCTAG    120
GAATGAATAT  GATATAAAAG  AGAATGAAAA  ATTTTTAGAC  GTGTATAAAG  AAAAATTTAA    180
TGAATTAGAT  AAAAAGAAAT  ATGGAAATGT  TCAAAAAACT  GATAAGAAAA  TATTTACTTT    240
TATAGAAAAT  AAATTAGATA  TTTTAAATAA  TTCAAAATTT  AATAAAAGAT  GGAAGAGTTA    300
TGGAACTCCA  GATAATATAG  ATAAAAATAT  GTCTTTAATA  AATAAACATA  ATAATGAAGA    360
AATGTTTAAC  AACAATTATC  AATCATTTTT  ATCGACAAGT  TCATTAATAA  AGCAAAATAA    420
ATATGTTCCT  ATTAACGCTG  TACGTGTGTC  TAGGATATTA  AGTTCCTGG   ATTCTAGAAT    480
TAATAATGGA  AGAAATACTT  CATCTAATAA  CGAAGTTTTA  AGTAATTGTA  GGGAAAAAAG    540
GAAAGGAATG  AAATGGGATT  GTAAAAGAA   AAATGATAGA  AGCAACTATG  TATGTATTCC    600
TGATCGTAGA  ATCCAATTAT  GCATTGTTAA  TCTTAGCATT  ATTAAACAT   ATACAAAAGA    660
GACCATGAAG  GATCATTTCA  TTGAAGCCTC  TAAAAAAGAA  TCTCAACTTT  TGCTTAAAAA    720
AAATGATAAC  AAATATAATT  CTAAATTTTG  TAATGATTTG  AAGAATAGTT  TTTTAGATTA    780
TGGACATCTT  GCTATGGGAA  ATGATATGGA  TTTTGGAGGT  TATTCAACTA  AGGCAGAAAA    840
CAAAATTCAA  GAAGTTTTTA  AAGGGGCTCA  TGGGGAAATA  AGTGAACATA  AAATTAAAAA    900
TTTTAGAAAA  GAATGGTGGA  ATGAATTTAG  AGAGAAACTT  TGGGAAGCTA  TGTTATCTGA    960
GCATAAAAAT  AATATAAATA  ATTGTAAAAA  TATTCCCCAA  GAAGAATTAC  AAATTACTCA   1020
ATGGATAAAA  GAATGGCATG  GAGAATTTTT  GCTTGAAAGA  GATAATAGAT  CAAAATTGCC   1080
AAAAAGTAAA  TGTAAAAATA  ATACATTATA  TGAAGCATGT  GAGAAGGAAT  GTATTGATCC   1140
ATGTATGAAA  TATAGAGATT  GGATTATTAG  AAGTAAATTT  GAATGGCATA  CGTTATCGAA   1200
AGAATATGAA  ACTCAAAAAG  TTCCAAAGGA  AAATGCGGAA  AATTATTTAA  TCAAAATTTC   1260
AGAAAACAAG  AATGATGCTA  AAGTAAGTTT  ATTATTGAAT  AATTGTGATG  CTGAATATTC   1320
AAAATATTGT  GATTGTAAAC  ATACTACTAC  TCTCGTTAAA  AGCGTTTTAA  ATGGTAACGA   1380
CAATACAATT  AAGGAAAAGC  GTGAACATAT  TGATTTAGAT  GATTTTCTA   AATTTGGATG   1440
TGATAAAAAT  TCCGTTGATA  CAAACACAAA  GGTGTGGGAA  TGTAAAAACC  CTTATATATT   1500
ATCCACTAAA  GATGTATGTG  TACCTCCGAG  GAGGCAAGAA  TTATGTCTTG  GAAACATTGA   1560
TAGAATATAC  GATAAAAACC  TATTAATGAT  AAAAGAGCAT  ATTCTTGCTA  TTGCAATATA   1620
TGAATCAAGA  ATATTGAAAC  GAAAATATAA  GAATAAAGAT  GATAAAGAAG  TTTGTAAAAT   1680
CATAAATAAA  ACTTTCGCTG  ATATAAGAGA  TATTATAGGA  GGTACTGATT  ATTGGAATGA   1740
TTTGAGCAAT  AGAAAATTAG  TAGGAAAAAT  TAACACAAAT  TCAAAATATG  TTCACAGGAA   1800
```

```
TAAAAAAAAT GATAAGCTTT TTCGTGATGA GTGGTGGAAA GTTATTAAAA AAGATGTATG    1860
GAATGTGATA TCATGGGTAT TCAAGGATAA AACTGTTTGT AAAGAAGATG ATATTGAAAA    1920
TATACCACAA TTCTTCAGAT GGTTTAGTGA ATGGGGTGAT GATTATTGCC AGGATAAAAC    1980
AAAAATGATA GAGACTCTGA AGGTTGAATG CAAAGAAAAA CCTTGTGAAG ATGACAATTG    2040
TAAAAGTAAA TGTAATTCAT ATAAAGAATG GATATCAAAA AAAAAGAAG AGTATAATAA     2100
ACAAGCCAAA CAATACCAAG AATATCAAAA AGGAAATAAT TACAAAATGT ATTCTGAATT    2160
TAAATCTATA AAACCAGAAG TTTATTTAAA GAAATACTCG GAAAATGTT CTAACCTAAA     2220
TTTCGAAGAT GAATTTAAGG AAGAATTACA TTCAGATTAT AAAAATAAAT GTACGATGTG    2280
TCCAGAAGTA AAGGATGTAC CAATTTCTAT AATAAGAAAT AATGAACAAA CTTCGCAAGA    2340
AGCAGTTCCT GAGGAAAACA CTGAAATAGC ACACAGAACG GAAACTCCAT CTATCTCTGA    2400
AGGACCAAAA GGAAATGAAC AAAAGAACG TGATGACGAT AGTTTGAGTA AAATAAGTGT     2460
ATCACCAGAA AATTCAAGAC CTGAAACTGA TGCTAAAGAT ACTTCTAACT TGTTAAAATT    2520
AAAAGGAGAT GTTGATATTA GTATGCCTAA AGCAGTTATT GGGAGCAGTC CTAATGATAA    2580
TATAAATGTT ACTGAACAAG GGGATAATAT TTCCGGGGTG AATTCTAAAC CTTTATCTGA    2640
TGATGTACGT CCAGATAAAA AGGAATTAGA AGATCAAAAT AGTGATGAAT CGGAAGAAAC    2700
TGTAGTAAAT CATATATCAA AAAGTCCATC TATAAATAAT GGAGATGATT CAGGCAGTGG    2760
AAGTGCAACA GTGAGTGAAT CTAGTAGTTC AAATACTGGA TTGTCTATTG ATGATGATAG    2820
AAATGGTGAT ACATTTGTTC GAACACAAGA TACAGCAAAT ACTGAAGATG TTATTAGAAA    2880
AGAAAATGCT GACAAGGATG AAGATGAAAA AGGCGCAGAT GAAGAAAGAC ATAGTACTTC    2940
TGAAAGCTTA AGTTCACCTG AAGAAAAAAT GTTAACTGAT AATGAAGGAG GAAATAGTTT    3000
AAATCATGAA GAGGTGAAAG AACATACTAG TAATTCTGAT AATGTTCAAC AGTCTGGAGG    3060
AATTGTTAAT ATGAATGTTG AGAAAGAACT AAAAGATACT TTAGAAAATC CTTCTAGTAG    3120
CTTGGATGAA GGAAAAGCAC ATGAAGAATT ATCAGAACCA AATCTAAGCA GTGACCAAGA    3180
TATGTCTAAT ACACCTGGAC CTTTGGATAA CACCAGTGAA GAAACTACAG AAAGAATTAG    3240
TAATAATGAA TATAAAGTTA ACGAGAGGGA AGATGAGAGA ACGCTTACTA AGGAATATGA    3300
AGATATTGTT TTGAAAAGTC ATATGAATAG AGAATCAGAC GATGGTGAAT TATATGACGA    3360
AAATTCAGAC TTATCTACTG TAAATGATGA ATCAGAAGAC GCTGAAGCAA AAATGAAAGG    3420
AAATGATACA TCTGAAATGT CGCATAATAG TAGTCAACAT ATTGAGAGTG ATCAACAGAA    3480
AAACGATATG AAAACTGTTG GTGATTTGGG AACCACACAT GTACAAAACG AAATTAGTGT    3540
TCCTGTTACA GGAGAAATTG ATGAAAAATT AAGGGAAAGT AAAGAATCAA AAATTCATAA    3600
GGCTGAAGAG GAAAGATTAA GTCATACAGA TATACATAAA ATTAATCCTG AAGATAGAAA    3660
TAGTAATACA TTACATTTAA AAGATATAAG AAATGAGGAA AACGAAAGAC ACTTAACTAA    3720
TCAAAACATT AATATTAGTC AAGAAGGGA TTTGCAAAAA CATGGATTCC ATACCATGAA     3780
TAATCTACAT GGAGATGGAG TTTCCGAAAG AAGTCAAATT AATCATAGTC ATCATGGAAA    3840
CAGACAAGAT CGGGGGGGAA ATTCTGGGAA TGTTTTAAAT ATGAGATCTA ATAATAATAA    3900
TTTTAATAAT ATTCCAAGTA GATATAATTT ATATGATAAA AAATTAGATT TAGATCTTTA    3960
TGAAACAGA AATGATAGTA CAACAAAAGA ATTAATAAAG AAATTAGCAG AAATAAATAA     4020
ATGTGAGAAC GAAATTTCTG TAAAATATTG TGACCATATG ATTCATGAAG AAATCCCATT    4080
AAAAACATGC ACTAAAGAAA AAACAAGAAA TCTGTGTTGT GCAGTATCAG ATTACTGTAT    4140
GAGCTATTTT ACATATGATT CAGAGGAATA TTATAATTGT ACGAAAAGGG AATTTGATGA    4200
```

5,849,306

33                                                                  34

-continued

| TCCATCTTAT | ACATGTTTCA | GAAAGGAGGC | TTTTTCAAGT | ATGATATTCA | AATTTTTAAT | 4260 |
| AACAAATAAA | ATATATTATT | ATTTTTATAC | TTACAAAACT | GCAAAAGTAA | CAATAAAAAA | 4320 |
| AATTAATTTC | TCATTAATTT | TTTTTTTCTT | TTTTTCTTTT | TAGGTATGCC | ATATTATGCA | 4380 |
| GGAGCAGGTG | TGTTATTTAT | TATATTGGTT | ATTTTAGGTG | CTTCACAAGC | CAAATATCAA | 4440 |
| AGGTTAGAAA | AAATAAATAA | AAATAAAATT | GAGAAGAATG | TAAATTAAAT | ATAGAATTCG | 4500 |
| AGCTCGG    |            |            |            |            |            | 4507 |

( 2 ) INFORMATION FOR SEQ ID NO:4:

( i ) SEQUENCE CHARACTERISTICS:
        ( A ) LENGTH: 1435 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: Plasmodium falciparum ( x i ) SEQUENCE DESCRIPTION: SEQ ID NO:4:

```
Met Lys Cys Asn Ile Ser Ile Tyr Phe Phe Ala Ser Phe Phe Val Leu
 1               5                  10                 15

Tyr Phe Ala Lys Ala Arg Asn Glu Tyr Asp Ile Lys Glu Asn Glu Lys
                20                 25                 30

Phe Leu Asp Val Tyr Lys Glu Lys Phe Asn Glu Leu Asp Lys Lys Lys
             35                 40                 45

Tyr Gly Asn Val Gln Lys Thr Asp Lys Lys Ile Phe Thr Phe Ile Glu
 50                 55                 60

Asn Lys Leu Asp Ile Leu Asn Asn Ser Lys Phe Asn Lys Arg Trp Lys
65                  70                 75                    80

Ser Tyr Gly Thr Pro Asp Asn Ile Asp Lys Asn Met Ser Leu Ile Asn
                85                 90                 95

Lys His Asn Asn Glu Glu Met Phe Asn Asn Tyr Gln Ser Phe Leu
             100                105                110

Ser Thr Ser Ser Leu Ile Lys Gln Asn Lys Tyr Val Pro Ile Asn Ala
            115                120                125

Val Arg Val Ser Arg Ile Leu Ser Phe Leu Asp Ser Arg Ile Asn Asn
        130                135                140

Gly Arg Asn Thr Ser Ser Asn Asn Glu Val Leu Ser Asn Cys Arg Glu
145                150                155                   160

Lys Arg Lys Gly Met Lys Trp Asp Cys Lys Lys Lys Asn Asp Arg Ser
                165                170                175

Asn Tyr Val Cys Ile Pro Asp Arg Arg Ile Gln Leu Cys Ile Val Asn
            180                185                190

Leu Ser Ile Ile Lys Thr Tyr Thr Lys Glu Thr Met Lys Asp His Phe
        195                200                205

Ile Glu Ala Ser Lys Lys Glu Ser Gln Leu Leu Leu Lys Asn Asp
    210                215                220

Asn Lys Tyr Asn Ser Lys Phe Cys Asn Asp Leu Lys Asn Ser Phe Leu
225                230                235                   240

Asp Tyr Gly His Leu Ala Met Gly Asn Asp Met Asp Phe Gly Gly Tyr
            245                250                255

Ser Thr Lys Ala Glu Asn Lys Ile Gln Glu Val Phe Lys Gly Ala His
            260                265                270
```

```
Gly Glu Ile Ser Glu His Lys Ile Lys Asn Phe Arg Lys Glu Trp Trp
        275             280                 285

Asn Glu Phe Arg Glu Lys Leu Trp Glu Ala Met Leu Ser Glu His Lys
    290             295             300

Asn Asn Ile Asn Asn Cys Lys Asn Ile Pro Gln Glu Glu Leu Gln Ile
305             310             315                         320

Thr Gln Trp Ile Lys Glu Trp His Gly Phe Leu Leu Glu Arg Asp
                325             330                     335

Asn Arg Ser Lys Leu Pro Lys Ser Lys Cys Lys Asn Asn Thr Leu Tyr
            340             345                 350

Glu Ala Cys Glu Lys Glu Cys Ile Asp Pro Cys Met Lys Tyr Arg Asp
        355             360             365

Trp Ile Ile Arg Ser Lys Phe Glu Trp His Thr Leu Ser Lys Glu Tyr
    370             375             380

Glu Thr Gln Lys Val Pro Lys Glu Asn Ala Glu Asn Tyr Leu Ile Lys
385             390             395                         400

Ile Ser Glu Asn Lys Asn Asp Ala Lys Val Ser Leu Leu Leu Asn Asn
            405             410                 415

Cys Asp Ala Glu Tyr Ser Lys Tyr Cys Asp Cys Lys His Thr Thr Thr
            420             425             430

Leu Val Lys Ser Val Leu Asn Gly Asn Asp Asn Thr Ile Lys Glu Lys
        435             440                 445

Arg Glu His Ile Asp Leu Asp Asp Phe Ser Lys Phe Gly Cys Asp Lys
    450             455             460

Asn Ser Val Asp Thr Asn Thr Lys Val Trp Glu Cys Lys Asn Pro Tyr
465             470             475                         480

Ile Leu Ser Thr Lys Asp Val Cys Val Pro Pro Arg Arg Gln Glu Leu
            485             490                 495

Cys Leu Gly Asn Ile Asp Arg Ile Tyr Asp Lys Asn Leu Leu Met Ile
            500             505                 510

Lys Glu His Ile Leu Ala Ile Ala Ile Tyr Glu Ser Arg Ile Leu Lys
        515             520                 525

Arg Lys Tyr Lys Asn Lys Asp Asp Lys Glu Val Cys Lys Ile Ile Asn
    530             535             540

Lys Thr Phe Ala Asp Ile Arg Asp Ile Ile Gly Gly Thr Asp Tyr Trp
545             550             555                         560

Asn Asp Leu Ser Asn Arg Lys Leu Val Gly Lys Ile Asn Thr Asn Ser
            565             570                 575

Lys Tyr Val His Arg Asn Lys Lys Asn Asp Lys Leu Phe Arg Asp Glu
            580             585                 590

Trp Trp Lys Val Ile Lys Lys Asp Val Trp Asn Val Ile Ser Trp Val
        595             600             605

Phe Lys Asp Lys Thr Val Cys Lys Glu Asp Asp Ile Glu Asn Ile Pro
    610             615             620

Gln Phe Phe Arg Trp Phe Ser Glu Trp Gly Asp Asp Tyr Cys Gln Asp
625             630             635                         640

Lys Thr Lys Met Ile Glu Thr Leu Lys Val Glu Cys Lys Glu Lys Pro
            645             650                 655

Cys Glu Asp Asp Asn Cys Lys Ser Lys Cys Asn Ser Tyr Lys Glu Trp
            660             665             670

Ile Ser Lys Lys Lys Glu Glu Tyr Asn Lys Gln Ala Lys Gln Tyr Gln
        675             680                 685

Glu Tyr Gln Lys Gly Asn Asn Tyr Lys Met Tyr Ser Glu Phe Lys Ser
```

```
                  690                      695                     700
Ile  Lys  Pro  Glu  Val  Tyr  Leu  Lys  Lys  Tyr  Ser  Glu  Lys  Cys  Ser  Asn
705                      710                     715                     720

Leu  Asn  Phe  Glu  Asp  Glu  Phe  Lys  Glu  Leu  His  Ser  Asp  Tyr  Lys
                         725                     730                     735

Asn  Lys  Cys  Thr  Met  Cys  Pro  Glu  Val  Lys  Asp  Val  Pro  Ile  Ser  Ile
                    740                     745                     750

Ile  Arg  Asn  Asn  Glu  Gln  Thr  Ser  Gln  Glu  Ala  Val  Pro  Glu  Glu  Asn
               755                     760                     765

Thr  Glu  Ile  Ala  His  Arg  Thr  Glu  Thr  Pro  Ser  Ile  Ser  Glu  Gly  Pro
770                      775                     780

Lys  Gly  Asn  Glu  Gln  Lys  Glu  Arg  Asp  Asp  Ser  Leu  Ser  Lys  Ile
785                      790                     795                     800

Ser  Val  Ser  Pro  Glu  Asn  Ser  Arg  Pro  Glu  Thr  Asp  Ala  Lys  Asp  Thr
                    805                     810                     815

Ser  Asn  Leu  Leu  Lys  Leu  Lys  Gly  Asp  Val  Asp  Ile  Ser  Met  Pro  Lys
                    820                     825                     830

Ala  Val  Ile  Gly  Ser  Ser  Pro  Asn  Asp  Ile  Asn  Val  Thr  Glu  Gln
               835                     840                     845

Gly  Asp  Asn  Ile  Ser  Gly  Val  Asn  Ser  Lys  Pro  Leu  Ser  Asp  Asp  Val
          850                     855                     860

Arg  Pro  Asp  Lys  Lys  Glu  Leu  Glu  Asp  Gln  Asn  Ser  Asp  Glu  Ser  Glu
865                      870                     875                     880

Glu  Thr  Val  Val  Asn  His  Ile  Ser  Lys  Ser  Pro  Ser  Ile  Asn  Asn  Gly
                    885                     890                     895

Asp  Asp  Ser  Gly  Ser  Gly  Ser  Ala  Thr  Val  Ser  Glu  Ser  Ser  Ser  Ser
               900                     905                     910

Asn  Thr  Gly  Leu  Ser  Ile  Asp  Asp  Arg  Asn  Gly  Asp  Thr  Phe  Val
               915                     920                     925

Arg  Thr  Gln  Asp  Thr  Ala  Asn  Thr  Glu  Asp  Val  Ile  Arg  Lys  Glu  Asn
          930                     935                     940

Ala  Asp  Lys  Asp  Glu  Asp  Glu  Lys  Gly  Ala  Asp  Glu  Glu  Arg  His  Ser
945                      950                     955                     960

Thr  Ser  Glu  Ser  Leu  Ser  Ser  Pro  Glu  Glu  Lys  Met  Leu  Thr  Asp  Asn
                    965                     970                     975

Glu  Gly  Gly  Asn  Ser  Leu  Asn  His  Glu  Glu  Val  Lys  Glu  His  Thr  Ser
               980                     985                     990

Asn  Ser  Asp  Asn  Val  Gln  Gln  Ser  Gly  Gly  Ile  Val  Asn  Met  Asn  Val
          995                    1000                    1005

Glu  Lys  Glu  Leu  Lys  Asp  Thr  Leu  Glu  Asn  Pro  Ser  Ser  Ser  Leu  Asp
     1010                    1015                    1020

Glu  Gly  Lys  Ala  His  Glu  Glu  Leu  Ser  Glu  Pro  Asn  Leu  Ser  Ser  Asp
1025                     1030                    1035                    1040

Gln  Asp  Met  Ser  Asn  Thr  Pro  Gly  Pro  Leu  Asp  Asn  Thr  Ser  Glu  Glu
                    1045                    1050                    1055

Thr  Thr  Glu  Arg  Ile  Ser  Asn  Asn  Glu  Tyr  Lys  Val  Asn  Glu  Arg  Glu
               1060                    1065                    1070

Asp  Glu  Arg  Thr  Leu  Thr  Lys  Glu  Tyr  Glu  Asp  Ile  Val  Leu  Lys  Ser
          1075                    1080                    1085

His  Met  Asn  Arg  Glu  Ser  Asp  Asp  Gly  Glu  Leu  Tyr  Asp  Glu  Asn  Ser
     1090                    1095                    1100

Asp  Leu  Ser  Thr  Val  Asn  Asp  Glu  Ser  Glu  Asp  Ala  Glu  Ala  Lys  Met
1105                     1110                    1115                    1120
```

Lys Gly Asn Asp Thr Ser Glu Met Ser His Asn Ser Ser Gln His Ile
1125                     1130                    1135

Glu Ser Asp Gln Gln Lys Asn Asp Met Lys Thr Val Gly Asp Leu Gly
1140                     1145                    1150

Thr Thr His Val Gln Asn Glu Ile Ser Val Pro Val Thr Gly Glu Ile
1155                     1160                    1165

Asp Glu Lys Leu Arg Glu Ser Lys Glu Ser Lys Ile His Lys Ala Glu
1170                     1175                    1180

Glu Glu Arg Leu Ser His Thr Asp Ile His Lys Ile Asn Pro Glu Asp
1185                     1190                    1195                    1200

Arg Asn Ser Asn Thr Leu His Leu Lys Asp Ile Arg Asn Glu Glu Asn
             1205                    1210                    1215

Glu Arg His Leu Thr Asn Gln Asn Ile Asn Ile Ser Gln Glu Arg Asp
             1220                    1225                    1230

Leu Gln Lys His Gly Phe His Thr Met Asn Asn Leu His Gly Asp Gly
             1235                    1240                    1245

Val Ser Glu Arg Ser Gln Ile Asn His Ser His His Gly Asn Arg Gln
             1250                    1255                    1260

Asp Arg Gly Gly Asn Ser Gly Asn Val Leu Asn Met Arg Ser Asn Asn
1265                     1270                    1275                    1280

Asn Asn Phe Asn Asn Ile Pro Ser Arg Tyr Asn Leu Tyr Asp Lys Lys
             1285                    1290                    1295

Leu Asp Leu Asp Leu Tyr Glu Asn Arg Asn Asp Ser Thr Thr Lys Glu
             1300                    1305                    1310

Leu Ile Lys Lys Leu Ala Glu Ile Asn Lys Cys Glu Asn Glu Ile Ser
             1315                    1320                    1325

Val Lys Tyr Cys Asp His Met Ile His Glu Glu Ile Pro Leu Lys Thr
             1330                    1335                    1340

Cys Thr Lys Glu Lys Thr Arg Asn Leu Cys Cys Ala Val Ser Asp Tyr
1345                     1350                    1355                    1360

Cys Met Ser Tyr Phe Thr Tyr Asp Ser Glu Glu Tyr Tyr Asn Cys Thr
             1365                    1370                    1375

Lys Arg Glu Phe Asp Asp Pro Ser Tyr Thr Cys Phe Arg Lys Glu Ala
             1380                    1385                    1390

Phe Ser Ser Met Ile Phe Lys Phe Leu Ile Thr Asn Lys Ile Tyr Tyr
             1395                    1400                    1405

Tyr Phe Tyr Thr Tyr Lys Thr Ala Lys Val Thr Ile Lys Lys Ile Asn
             1410                    1415                    1420

Phe Ser Leu Ile Phe Phe Phe Phe Phe Ser Phe
1425                     1430                    1435

( 2 ) INFORMATION FOR SEQ ID NO:5:

( i ) SEQUENCE CHARACTERISTICS:
        ( A ) LENGTH: 2288 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Plasmodium falciparum ( x i ) SEQUENCE DESCRIPTION: SEQ ID NO:5:

CACTTTATGC TTCCGGCTCG TATGTTGTGT GGAATTGTGA GCGGATAACA ATTTCACACA    60

| | | | | | |
|---|---|---|---|---|---|
| GGAAACAGCT | ATGACCATGA | TTACGCCAAG | CTCTAATACG | ACTCACTATA | GGGAAAGCTG | 120 |
| GTACGCCTGC | AGGTCCGGTC | CGGAATTCAA | TAAAATATTT | CCAGAAAGGA | ATGTGCAAAT | 180 |
| TCACATATCC | AATATATTCA | AGGAATATAA | AGAAATAAT | GTAGATATCA | TATTTGGAAC | 240 |
| GTTGAATTAT | GAATATAATA | ATTTCTGTAA | AGAAAACCT | GAATTAGTAT | CTGCTGCCAA | 300 |
| GTATAATCTG | AAAGCTCCAA | ATGCTAAATC | CCCTAGAATA | TACAAATCTA | AGGAGCATGA | 360 |
| AGAATCAAGT | GTGTTTGGTT | GCAAAACGAA | AATCAGTAAA | GTTAAAAAA | AATGGAATTG | 420 |
| TTATAGTAAT | AATAAAGTAA | CTAAACCTGA | AGGTGTATGT | GGACCACCAA | GAAGGCAACA | 480 |
| ATTATGTCTT | GGATATATAT | TTTTGATTCG | CGACGGTAAC | GAGGAAGGAT | TAAAAGATCA | 540 |
| TATTAATAAG | GCAGCTAATT | ATGAGGCAAT | GCATTTAAAA | GAGAAATATG | AGAATGCTGG | 600 |
| TGGTGATAAA | ATTTGCAATG | CTATATTGGG | AAGTTATGCA | GATATTGGAG | ATATTGTAAG | 660 |
| AGGTTTGGAT | GTTTGGAGGG | ATATAAATAC | TAATAAATTA | TCAGAAAAAT | TCCAAAAAAT | 720 |
| TTTTATGGGT | GGTGGTAATT | CTAGGAAAAA | ACAAACGAT | AATAATGAAC | GTAATAAATG | 780 |
| GTGGGAAAAA | CAAAGGAATT | TAATATGGTC | TAGTATGGTA | AAACACATTC | CAAAAGGAAA | 840 |
| AACATGTAAA | CGTCATAATA | ATTTTGAGAA | AATTCCTCAA | TTTTTGAGAT | GGTTAAAAGA | 900 |
| ATGGGGTGAT | GAATTTTGTG | AGGAAATGGG | TACGGAAGTC | AAGCAATTAG | AGAAATATG | 960 |
| TGAAAATAAA | AATTGTTCGG | AAAAAAAATG | TAAAATGCA | TGTAGTTCCT | ATGAAAAATG | 1020 |
| GATAAAGGAA | CGAAAAAATG | AATATAATTT | GCAATCAAAG | AAATTTGATA | GTGATAAAAA | 1080 |
| ATTAAATAAA | AAAAACAATC | TTTATAATAA | ATTTGAGGAT | TCTAAAGCTT | ATTTAAGGAG | 1140 |
| TGAATCAAAA | CAGTGCTCAA | ATATAGAATT | TAATGATGAA | ACATTTACAT | TTCCTAATAA | 1200 |
| ATATAAAGAG | GCTTGTATGG | TATGTGAAAA | TCCTTCATCT | TCGAAAGCTC | TTAAACCTAT | 1260 |
| AAAAACGAAT | GTGTTTCCTA | TAGAGGAATC | AAAAAAATCT | GAGTTATCAA | GTTTAACAGA | 1320 |
| TAAATCTAAG | AATACTCCTA | ATAGTTCTGG | TGGGGAAAT | TATGGAGATA | GACAAATATC | 1380 |
| AAAAAGAGAC | GATGTTCATC | ATGATGGTCC | TAAGGAAGTG | AAATCCGGAG | AAAAAGAGGT | 1440 |
| ACCAAAAATA | GATGCAGCTG | TTAAAACAGA | AAATGAATTT | ACCTCTAATC | GAAACGATAT | 1500 |
| TGAAGGAAAG | GAAAAAAGTA | AAGGTGATCA | TTCTTCTCCT | GTTCATTCTA | AAGATATAAA | 1560 |
| AAATGAGGAA | CCACAAGGG | TGGTGTCTGA | AAATTTACCT | AAAATTGAAG | AGAAAATGGA | 1620 |
| ATCTTCTGAT | TCTATACCAA | TTACTCATAT | AGAAGCTGAA | AAGGGTCAGT | CTTCTAATTC | 1680 |
| TAGCGATAAT | GATCCTGCAG | TAGTAAGTGG | TAGAGAATCT | AAAGATGTAA | ATCTTCATAC | 1740 |
| TTCTGAAAGG | ATTAAAGAAA | ATGAAGAAGG | TGTGATTAAA | ACAGATGATA | GTTCAAAAAG | 1800 |
| TATTGAAATT | TCTAAAATAC | CATCTGACCA | AAATAATCAT | AGTGATTTAT | CACAGAATGC | 1860 |
| AAATGAGGAC | TCTAATCAAG | GGAATAAGGA | AACAATAAAT | CCTCCTTCTA | CAGAAAAAAA | 1920 |
| TCTCAAAGAA | ATTCATTATA | AAACATCTGA | TTCTGATGAT | CATGGTTCTA | AAATTAAAAG | 1980 |
| TGAAATTGAA | CCAAAGGAGT | TAACGGAGGA | ATCACCTCTT | ACTGATAAAA | AAACTGAAAG | 2040 |
| TGCAGCGATT | GGTGATAAAA | ATCATGAATC | AGTAAAAGC | GCTGATATTT | TTCAATCTGA | 2100 |
| GATTCATAAT | TCTGATAATA | GAGATAGAAT | TGTTTCTGAA | AGTGTAGTTC | AGGATTCTTC | 2160 |
| AGGAAGCTCT | ATGAGTACTG | AATCTATACG | TACTGATAAC | AAGGATTTTA | AAACAAGTGA | 2220 |
| GGATATTGCA | CCTTCTATTA | ATGGTCGGAA | TTCCCGGGTC | GACGAGCTCA | CTAGTCGGCG | 2280 |
| GCCGCTCT | | | | | | 2288 |

( 2 ) INFORMATION FOR SEQ ID NO:6:

( i ) SEQUENCE CHARACTERISTICS:

(A) LENGTH: 749 amino acids
(B) TYPE: amino acid
(C) STRANDEDNESS: single
(D) TOPOLOGY: linear (ii) MOLECULE TYPE: protein (iii) HYPOTHETICAL: NO (v) ORIGINAL SOURCE:
(A) ORGANISM: Plasmodium falciparum (xi) SEQUENCE DESCRIPTION: SEQ ID NO:6:

| Ala | Asp | Asn | Asn | Phe | Thr | Gln | Glu | Thr | Ala | Met | Thr | Met | Ile | Thr | Pro |
|---|---|---|---|---|---|---|---|---|---|---|---|---|---|---|---|
| 1 | | | | 5 | | | | | 10 | | | | | 15 | |
| Ser | Ser | Asn | Thr | Thr | His | Tyr | Arg | Glu | Ser | Trp | Tyr | Ala | Cys | Arg | Ser |
| | | | 20 | | | | 25 | | | | | 30 | | | |
| Gly | Pro | Glu | Phe | Asn | Lys | Ile | Phe | Pro | Glu | Arg | Asn | Val | Gln | Ile | His |
| | | 35 | | | | | 40 | | | | | 45 | | | |
| Ile | Ser | Asn | Ile | Phe | Lys | Glu | Tyr | Lys | Glu | Asn | Asn | Val | Asp | Ile | Ile |
| | 50 | | | | | 55 | | | | | 60 | | | | |
| Phe | Gly | Thr | Leu | Asn | Tyr | Glu | Tyr | Asn | Asn | Phe | Cys | Lys | Glu | Lys | Pro |
| 65 | | | | | 70 | | | | | 75 | | | | | 80 |
| Glu | Leu | Val | Ser | Ala | Ala | Lys | Tyr | Asn | Leu | Lys | Ala | Pro | Asn | Ala | Lys |
| | | | | 85 | | | | | 90 | | | | | 95 | |
| Ser | Pro | Arg | Ile | Tyr | Lys | Ser | Lys | Glu | His | Glu | Glu | Ser | Ser | Val | Phe |
| | | | | | 100 | | | | | 105 | | | | | 110 |
| Gly | Cys | Lys | Thr | Lys | Ile | Ser | Lys | Val | Lys | Lys | Lys | Trp | Asn | Cys | Tyr |
| | | | 115 | | | | | 120 | | | | | 125 | | |
| Ser | Asn | Asn | Lys | Val | Thr | Lys | Pro | Glu | Gly | Val | Cys | Gly | Pro | Pro | Arg |
| | | 130 | | | | | 135 | | | | | 140 | | | |
| Arg | Gln | Gln | Leu | Cys | Leu | Gly | Tyr | Ile | Phe | Leu | Ile | Arg | Asp | Gly | Asn |
| 145 | | | | | 150 | | | | | 155 | | | | | 160 |
| Glu | Glu | Gly | Leu | Lys | Asp | His | Ile | Asn | Lys | Ala | Ala | Asn | Tyr | Glu | Ala |
| | | | | 165 | | | | | 170 | | | | | 175 | |
| Met | His | Leu | Lys | Glu | Lys | Tyr | Glu | Asn | Ala | Gly | Gly | Asp | Lys | Ile | Cys |
| | | | 180 | | | | | 185 | | | | | 190 | | |
| Asn | Ala | Ile | Leu | Gly | Ser | Tyr | Ala | Asp | Ile | Gly | Asp | Ile | Val | Arg | Gly |
| | | 195 | | | | | 200 | | | | | 205 | | | |
| Leu | Asp | Val | Trp | Arg | Asp | Ile | Asn | Thr | Asn | Lys | Leu | Ser | Glu | Lys | Phe |
| | 210 | | | | | 215 | | | | | 220 | | | | |
| Gln | Lys | Ile | Phe | Met | Gly | Gly | Gly | Asn | Ser | Arg | Lys | Lys | Gln | Asn | Asp |
| 225 | | | | | 230 | | | | | 235 | | | | | 240 |
| Asn | Asn | Glu | Arg | Asn | Lys | Trp | Trp | Glu | Lys | Gln | Arg | Asn | Leu | Ile | Trp |
| | | | | 245 | | | | | 250 | | | | | 255 | |
| Ser | Ser | Met | Val | Lys | His | Ile | Pro | Lys | Gly | Lys | Thr | Cys | Lys | Arg | His |
| | | | 260 | | | | | 265 | | | | | 270 | | |
| Asn | Asn | Phe | Glu | Lys | Ile | Pro | Gln | Phe | Leu | Arg | Trp | Leu | Lys | Glu | Trp |
| | | 275 | | | | | 280 | | | | | 285 | | | |
| Gly | Asp | Glu | Phe | Cys | Glu | Glu | Met | Gly | Thr | Glu | Val | Lys | Gln | Leu | Glu |
| | | 290 | | | | | 295 | | | | | 300 | | | |
| Lys | Ile | Cys | Glu | Asn | Lys | Asn | Cys | Ser | Glu | Lys | Lys | Cys | Lys | Asn | Ala |
| 305 | | | | | 310 | | | | | 315 | | | | | 320 |
| Cys | Ser | Ser | Tyr | Glu | Lys | Trp | Ile | Lys | Glu | Arg | Lys | Asn | Glu | Tyr | Asn |
| | | | | 325 | | | | | 330 | | | | | 335 | |
| Leu | Gln | Ser | Lys | Lys | Phe | Asp | Ser | Asp | Lys | Lys | Leu | Asn | Lys | Lys | Asn |
| | | | 340 | | | | | 345 | | | | | 350 | | |

```
Asn Leu Tyr Asn Lys Phe Glu Asp Ser Lys Ala Tyr Leu Arg Ser Glu
        355             360             365

Ser Lys Gln Cys Ser Asn Ile Glu Phe Asn Asp Glu Thr Phe Thr Phe
    370             375             380

Pro Asn Lys Tyr Lys Glu Ala Cys Met Val Cys Glu Asn Pro Ser Ser
385             390             395                         400

Ser Lys Ala Leu Lys Pro Ile Lys Thr Asn Val Phe Pro Ile Glu Glu
                405             410                     415

Ser Lys Lys Ser Glu Leu Ser Ser Leu Thr Asp Lys Ser Lys Asn Thr
                420             425                 430

Pro Asn Ser Ser Gly Gly Gly Asn Tyr Gly Asp Arg Gln Ile Ser Lys
            435             440             445

Arg Asp Asp Val His His Asp Gly Pro Lys Glu Val Lys Ser Gly Glu
    450             455                     460

Lys Glu Val Pro Lys Ile Asp Ala Ala Val Lys Thr Glu Asn Glu Phe
465             470             475                         480

Thr Ser Asn Arg Asn Asp Ile Glu Gly Lys Glu Lys Ser Lys Gly Asp
                485             490                     495

His Ser Ser Pro Val His Ser Lys Asp Ile Lys Asn Glu Glu Pro Gln
            500             505                     510

Arg Val Val Ser Glu Asn Leu Pro Lys Ile Glu Glu Lys Met Glu Ser
        515             520                 525

Ser Asp Ser Ile Pro Ile Thr His Ile Glu Ala Glu Lys Gly Gln Ser
    530             535                 540

Ser Asn Ser Ser Asp Asn Asp Pro Ala Val Val Ser Gly Arg Glu Ser
545             550             555                         560

Lys Asp Val Asn Leu His Thr Ser Glu Arg Ile Lys Glu Asn Glu Glu
                565             570                     575

Gly Val Ile Lys Thr Asp Asp Ser Ser Lys Ser Ile Glu Ile Ser Lys
            580             585                 590

Ile Pro Ser Asp Gln Asn Asn His Ser Asp Leu Ser Gln Asn Ala Asn
        595             600             605

Glu Asp Ser Asn Gln Gly Asn Lys Glu Thr Ile Asn Pro Pro Ser Thr
    610             615             620

Glu Lys Asn Leu Lys Glu Ile His Tyr Lys Thr Ser Asp Ser Asp Asp
625             630             635                         640

His Gly Ser Lys Ile Lys Ser Glu Ile Glu Pro Lys Glu Leu Thr Glu
                645             650                     655

Glu Ser Pro Leu Thr Asp Lys Lys Thr Glu Ser Ala Ala Ile Gly Asp
            660             665                 670

Lys Asn His Glu Ser Val Lys Ser Ala Asp Ile Phe Gln Ser Glu Ile
        675             680             685

His Asn Ser Asp Asn Arg Asp Arg Ile Val Ser Glu Ser Val Val Gln
    690             695             700

Asp Ser Ser Gly Ser Ser Met Ser Thr Glu Ser Ile Arg Thr Asp Asn
705             710             715                         720

Lys Asp Phe Lys Thr Ser Glu Asp Ile Ala Pro Ser Ile Asn Gly Arg
                725             730                     735

Asn Ser Arg Val Asp Glu Leu Thr Ser Arg Arg Pro Leu
            740             745
```

( 2 ) INFORMATION FOR SEQ ID NO:7:

( i ) SEQUENCE CHARACTERISTICS:
        ( A ) LENGTH: 2606 base pairs (B) TYPE: nucleic acid
(C) STRANDEDNESS: single
(D) TOPOLOGY: linear (ii) MOLECULE TYPE: DNA (genomic)

(iii) HYPOTHETICAL: NO (vi) ORIGINAL SOURCE:
(A) ORGANISM: Plasmodium falciparum (xi) SEQUENCE DESCRIPTION: SEQ ID NO:7:

| | | | | | |
|---|---|---|---|---|---|
| AGCTCTATTA | CGACTCACTA | TAGGGAAAGC | TGGTACGCCT | GCAGGTACCG | GTCCGGAATT | 60 |
| CCCGGGTCGA | CGAGCTCACT | AGTCGGCGGC | CGCTCTAGAG | GATCCAAGCT | TAATAGTGTT | 120 |
| TATACGTCTA | TTGGCTTATT | TTTAAATAGC | TTAAAAAGCG | GACCATGTAA | AAAGGATAAT | 180 |
| GATAATGCAG | AGGATAATAT | AGATTTTGGT | GATGAAGGTA | AACATTTAA | AGAGGCAGAT | 240 |
| AATTGTAAAC | CATGTTCTCA | ATTTACTGTT | GATTGTAAAA | ATTGTAATGG | TGGTGATACA | 300 |
| AAAGGGAAGT | GCAATGGCAG | CAATGGCAAA | AAGAATGGAA | ATGATTATAT | TACTGCAAGT | 360 |
| GATATTGAAA | ATGGAGGGAA | TTCTATTGGA | AATATAGATA | TGGTTGTTAG | TGATAAGGAT | 420 |
| GCAAATGGAT | TTAATGGTTT | AGACGCTTGT | GGAAGTGCAA | ATATCTTTAA | AGGTATTAGA | 480 |
| AAAGAACAAT | GGAAATGTGC | TAAAGTATGT | GGTTTAGATG | TATGTGGTCT | TAAAAATGGT | 540 |
| AATGGTAGTA | TAGATAAAGA | TCAAAACAA | ATTATAATTA | TTAGAGCATT | GCTTAAACGT | 600 |
| TGGGTAGAAT | ATTTTTTAGA | AGATTATAAT | AAAATTAATG | CCAAAATTTC | ACATTGTACG | 660 |
| AAAAAGGATA | ATGAATCCAC | ATGTACAAAT | GATTGTCCAA | ATAAATGTAC | ATGTGTAGAA | 720 |
| GAGTGGATAA | ATCAGAAAAG | GACAGAATGG | AAAAATATAA | AAAAACATTA | CAAACACAA | 780 |
| AATGAAAATG | GTGACAATAA | CATGAAATCT | TTGGTTACAG | ATATTTTGGG | TGCCTTGCAA | 840 |
| CCCCAAAGTG | ATGTTAACAA | AGCTATAAAA | CCTTGTAGTG | GTTTAACTGC | GTTCGAGAGT | 900 |
| TTTTGTGGTC | TTAATGGCGC | TGATAACTCA | GAAAAAAAG | AAGGTGAAGA | TTACGATCTT | 960 |
| GTTCTATGTA | TGCTTAAAAA | TCTTGAAAAA | CAAATTCAGG | AGTGCAAAAA | GAAACATGGC | 1020 |
| GAAACTAGTG | TCGAAAATGG | TGGCAAATCA | TGTACCCCCC | TTGACAACAC | CACCCTTGAG | 1080 |
| GAGGAACCCA | TAGAAGAGGA | AAACCAAGTG | GAAGCGCCGA | ACATTTGTCC | AAAACAAACA | 1140 |
| GTGGAAGATA | AAAAAAAGA | GGAAGAAGAA | GAAACTTGTA | CACCGGCATC | ACCAGTACCA | 1200 |
| GAAAAACCGG | TACCTCATGT | GGCACGTTGG | CGAACATTTA | CACCACCTGA | GGTATTCAAG | 1260 |
| ATATGGAGGG | GAAGGAGAAA | TAAAACTACG | TGCGAAATAG | TGGCAGAAAT | GCTTAAAGAT | 1320 |
| AAGAATGGAA | GGACTACAGT | AGGTGAATGT | TATAGAAAAG | AAACTTATTC | TGAATGGACG | 1380 |
| TGTGATGAAA | GTAAGATTAA | AATGGGACAG | CATGGAGCAT | GTATTCCTCC | AAGAAGACAA | 1440 |
| AAATTATGTT | TACATTATTT | AGAAAAAATA | ATGACAAATA | CAAATGAATT | GAAATACGCA | 1500 |
| TTTATTAAAT | GTGCTGCAGC | AGAAACTTTT | TTGTTATGGC | AAAACTACAA | AAAAGATAAG | 1560 |
| AATGGTAATG | CAGAAGATCT | CGATGAAAAA | TTAAAGGTG | GTATTATCCC | CGAAGATTTT | 1620 |
| AAACGGCAAA | TGTTCTATAC | GTTTGCAGAT | TATAGAGATA | TATGTTTGGG | TACGGATATA | 1680 |
| TCATCAAAAA | AAGATACAAG | TAAAGGTGTA | GGTAAAGTAA | AATGCAATAT | TGATGATGTT | 1740 |
| TTTTATAAAA | TTAGCAATAG | TATTCGTTAC | CGTAAAAGTT | GGTGGGAAAC | AAATGGTCCA | 1800 |
| GTTATATGGG | AAGGAATGTT | ATGCGCTTTA | AGTTATGATA | CGAGCCTAAA | TAATGTTAAT | 1860 |
| CCGGAAACTC | ACAAAAAACT | TACCGAAGGC | AATAACAACT | TGAGAAAGT | CATATTTGGT | 1920 |
| AGTGATAGTA | GCACTACTTT | GTCCAAATTT | TCTGAAAGAC | CTCAATTTCT | AAGATGGTTG | 1980 |
| ACTGAATGGG | GAGAAAATTT | CTGCAAAGAA | CAAAAAAAGG | AGTATAAGGT | GTTGTTGGCA | 2040 |

```
AAATGTAAGG  ATTGTGATGT  TGATGGTGAT  GGTAAATGTA  ATGGAAAATG  TGTTGCGTGC      2100

AAAGATCAAT  GTAAACAATA  TCATAGTTGG  ATTGGAATAT  GGATAGATAA  TTATAAAAAA      2160

CAAAAGGAA   GATATACTGA  GGTTAAAAAA  ATACCTCTGT  ATAAGAAGA   TAAAGACGTG      2220

AAAAACTCAG  ATGATGCTCG  CGATTATTTA  AAAACACAAT  TACAAAATAT  GAAATGTGTA      2280

AATGGAACTA  CTGATGAAAA  TTGTGAGTAT  AAGTGTATGC  ATAAAACCTC  ATCCACAAAT      2340

AGTGATATGC  CCGAATCGTT  GGACGAAAAG  CCGGAAAAGG  TCAAAGACAA  GTGTAATTGT      2400

GTACCTAATG  AATGCAATGC  ATTGAGTGTA  AGTGGTAGCG  GTTTCCTGA   TGGTCAAGCT      2460

TACGTACGCG  TGCATGCGAC  GTCATAGCTC  TTCTATAGTG  TCACCTAAAT  TCAATTCACT      2520

GGCCGTCGTT  TTACAACGTC  GTGACTGGGA  AAACCTGGCG  TTACCCAACT  TAATCGCCTT      2580

GCAGCACATC  CCCCTTTCGC  CAGCTG                                              2606
```

( 2 ) INFORMATION FOR SEQ ID NO:8:

( i ) SEQUENCE CHARACTERISTICS:
        ( A ) LENGTH: 921 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: Plasmodium falciparum ( x i ) SEQUENCE DESCRIPTION: SEQ ID NO:8:

```
Lys  Leu  Asn  Ser  Val  Tyr  Thr  Ser  Ile  Gly  Leu  Phe  Leu  Asn  Ser  Leu
  1              5                        10                         15

Lys  Ser  Gly  Pro  Cys  Lys  Lys  Asp  Asn  Asp  Ala  Glu  Asp  Asn  Ile
                20                  25                       30

Asp  Phe  Gly  Asp  Glu  Gly  Lys  Thr  Phe  Lys  Glu  Ala  Asp  Asn  Cys  Lys
             35                        40                         45

Pro  Cys  Ser  Gln  Phe  Thr  Val  Asp  Cys  Lys  Asn  Cys  Asn  Gly  Gly  Asp
     50                       55                    60

Thr  Lys  Gly  Lys  Cys  Asn  Gly  Ser  Asn  Gly  Lys  Lys  Asn  Gly  Asn  Asp
 65                       70                        75                       80

Tyr  Ile  Thr  Ala  Ser  Asp  Ile  Glu  Asn  Gly  Gly  Asn  Ser  Ile  Gly  Asn
                    85                       90                         95

Ile  Asp  Met  Val  Val  Ser  Asp  Lys  Asp  Ala  Asn  Gly  Phe  Asn  Gly  Leu
                  100                      105                        110

Asp  Ala  Cys  Gly  Ser  Ala  Asn  Ile  Phe  Lys  Gly  Ile  Arg  Lys  Glu  Gln
            115                      120                       125

Trp  Lys  Cys  Ala  Lys  Val  Cys  Gly  Leu  Asp  Val  Cys  Gly  Leu  Lys  Asn
     130                      135                       140

Gly  Asn  Gly  Ser  Ile  Asp  Lys  Asp  Gln  Lys  Gln  Ile  Ile  Ile  Ile  Arg
145                       150                      155                      160

Ala  Leu  Leu  Lys  Arg  Trp  Val  Glu  Tyr  Phe  Leu  Glu  Asp  Tyr  Asn  Lys
                    165                      170                       175

Ile  Asn  Ala  Lys  Ile  Ser  His  Cys  Thr  Lys  Lys  Asp  Asn  Glu  Ser  Thr
                180                      185                       190

Cys  Thr  Asn  Asp  Cys  Pro  Asn  Lys  Cys  Thr  Cys  Val  Glu  Glu  Trp  Ile
          195                      200                       205

Asn  Gln  Lys  Arg  Thr  Glu  Trp  Lys  Asn  Ile  Lys  Lys  His  Tyr  Lys  Thr
     210                      215                       220
```

```
Gln  Asn  Glu  Asn  Gly  Asp  Asn  Asn  Met  Lys  Ser  Leu  Val  Thr  Asp  Ile
225                 230                 235                           240

Leu  Gly  Ala  Leu  Gln  Pro  Gln  Ser  Asp  Val  Asn  Lys  Ala  Ile  Lys  Pro
               245                      250                      255

Cys  Ser  Gly  Leu  Thr  Ala  Phe  Glu  Ser  Phe  Cys  Gly  Leu  Asn  Gly  Ala
               260                 265                      270

Asp  Asn  Ser  Glu  Lys  Lys  Glu  Gly  Glu  Asp  Tyr  Asp  Leu  Val  Leu  Cys
          275                      280                      285

Met  Leu  Lys  Asn  Leu  Glu  Lys  Gln  Ile  Gln  Glu  Cys  Lys  Lys  Lys  His
     290                      295                 300

Gly  Glu  Thr  Ser  Val  Glu  Asn  Gly  Gly  Lys  Ser  Cys  Thr  Pro  Leu  Asp
305                      310                 315                           320

Asn  Thr  Thr  Leu  Glu  Glu  Pro  Ile  Glu  Glu  Asn  Gln  Val  Glu
                    325                 330                      335

Ala  Pro  Asn  Ile  Cys  Pro  Lys  Gln  Thr  Val  Glu  Asp  Lys  Lys  Lys  Glu
               340                 345                      350

Glu  Glu  Glu  Glu  Thr  Cys  Thr  Pro  Ala  Ser  Pro  Val  Pro  Glu  Lys  Pro
               355                 360                      365

Val  Pro  His  Val  Ala  Arg  Trp  Arg  Thr  Phe  Thr  Pro  Pro  Glu  Val  Phe
     370                 375                 380

Lys  Ile  Trp  Arg  Gly  Arg  Arg  Asn  Lys  Thr  Thr  Cys  Glu  Ile  Val  Ala
385                      390                 395                           400

Glu  Met  Leu  Lys  Asp  Lys  Asn  Gly  Arg  Thr  Thr  Val  Gly  Glu  Cys  Tyr
               405                 410                      415

Arg  Lys  Glu  Thr  Tyr  Ser  Glu  Trp  Thr  Cys  Asp  Glu  Ser  Lys  Ile  Lys
               420                 425                      430

Met  Gly  Gln  His  Gly  Ala  Cys  Ile  Pro  Pro  Arg  Arg  Gln  Lys  Leu  Cys
               435                 440                      445

Leu  His  Tyr  Leu  Glu  Lys  Ile  Met  Thr  Asn  Thr  Asn  Glu  Leu  Lys  Tyr
     450                      455                 460

Ala  Phe  Ile  Lys  Cys  Ala  Ala  Ala  Glu  Thr  Phe  Leu  Leu  Trp  Gln  Asn
465                      470                 475                           480

Tyr  Lys  Lys  Asp  Lys  Asn  Gly  Asn  Ala  Glu  Asp  Leu  Asp  Glu  Lys  Leu
               485                 490                      495

Lys  Gly  Gly  Ile  Ile  Pro  Glu  Asp  Phe  Lys  Arg  Gln  Met  Phe  Tyr  Thr
               500                 505                      510

Phe  Ala  Asp  Tyr  Arg  Asp  Ile  Cys  Leu  Gly  Thr  Asp  Ile  Ser  Ser  Lys
               515                 520                      525

Lys  Asp  Thr  Ser  Lys  Gly  Val  Gly  Lys  Val  Lys  Cys  Asn  Ile  Asp  Asp
     530                      535                 540

Val  Phe  Tyr  Lys  Ile  Ser  Asn  Ser  Ile  Arg  Tyr  Arg  Lys  Ser  Trp  Trp
545                      550                 555                           560

Glu  Thr  Asn  Gly  Pro  Val  Ile  Trp  Glu  Gly  Met  Leu  Cys  Ala  Leu  Ser
               565                 570                      575

Tyr  Asp  Thr  Ser  Leu  Asn  Asn  Val  Asn  Pro  Glu  Thr  His  Lys  Lys  Leu
               580                 585                      590

Thr  Glu  Gly  Asn  Asn  Asn  Phe  Glu  Lys  Val  Ile  Phe  Gly  Ser  Asp  Ser
               595                 600                      605

Ser  Thr  Thr  Leu  Ser  Lys  Phe  Ser  Glu  Arg  Pro  Gln  Phe  Leu  Arg  Trp
     610                      615                 620

Leu  Thr  Glu  Trp  Gly  Glu  Asn  Phe  Cys  Lys  Glu  Gln  Lys  Lys  Glu  Tyr
625                      630                 635                           640

Lys  Val  Leu  Leu  Ala  Lys  Cys  Lys  Asp  Cys  Asp  Val  Asp  Gly  Asp  Gly
```

|     |     |     |     |     |     |     |     |     |     |     |     |     |     |     |
| --- | --- | --- | --- | --- | --- | --- | --- | --- | --- | --- | --- | --- | --- | --- |
|     |     |     | 645 |     |     |     |     | 650 |     |     |     |     | 655 |     |
| Lys | Cys | Asn | Gly<br>660 | Lys | Cys | Val | Ala | Cys<br>665 | Lys | Asp | Gln | Cys | Lys<br>670 | Gln | Tyr |
| His | Ser | Trp<br>675 | Ile | Gly | Ile | Trp | Ile<br>680 | Asp | Asn | Tyr | Lys | Lys<br>685 | Gln | Lys | Gly |
| Arg | Tyr<br>690 | Thr | Glu | Val | Lys | Lys<br>695 | Ile | Pro | Leu | Tyr | Lys<br>700 | Glu | Asp | Lys | Asp |
| Val<br>705 | Lys | Asn | Ser | Asp | Asp<br>710 | Ala | Arg | Asp | Tyr | Leu<br>715 | Lys | Thr | Gln | Leu | Gln<br>720 |
| Asn | Met | Lys | Cys | Val<br>725 | Asn | Gly | Thr | Thr | Asp<br>730 | Glu | Asn | Cys | Glu | Tyr<br>735 | Lys |
| Cys | Met | His | Lys<br>740 | Thr | Ser | Ser | Thr | Asn<br>745 | Ser | Asp | Met | Pro | Glu<br>750 | Ser | Leu |
| Asp | Glu | Lys<br>755 | Pro | Glu | Lys | Val | Lys<br>760 | Asp | Lys | Cys | Asn | Cys<br>765 | Val | Pro | Asn |
| Glu | Cys<br>770 | Asn | Ala | Leu | Ser | Val<br>775 | Ser | Gly | Ser | Gly | Phe<br>780 | Pro | Asp | Gly | Gln |
| Ala<br>785 | Phe | Gly | Gly | Gly | Val<br>790 | Leu | Glu | Gly | Thr | Cys<br>795 | Lys | Gly | Leu | Gly | Glu<br>800 |
| Pro | Lys | Lys | Lys | Ile<br>805 | Glu | Pro | Pro | Gln | Tyr<br>810 | Asp | Pro | Thr | Asn | Asp<br>815 | Ile |
| Leu | Lys | Ser | Thr<br>820 | Ile | Pro | Val | Thr | Ile<br>825 | Val | Leu | Ala | Leu | Gly<br>830 | Ser | Ile |
| Ala | Phe | Leu<br>835 | Phe | Met | Lys | Val | Ile<br>840 | Tyr | Ile | Tyr | Val | Trp<br>845 | Tyr | Ile | Tyr |
| Met | Leu<br>850 | Cys | Val | Gly | Ala | Leu<br>855 | Asp | Thr | Tyr | Ile | Cys<br>860 | Gly | Cys | Ile | Cys |
| Ile<br>865 | Cys | Ile | Phe | Ile | Cys<br>870 | Val | Ser | Val | Tyr | Val<br>875 | Cys | Val | Tyr | Val | Tyr<br>880 |
| Val | Phe | Leu | Tyr | Met<br>885 | Cys | Val | Phe | Tyr | Ile<br>890 | Tyr | Phe | Ile | Tyr | Ile<br>895 | Tyr |
| Val | Phe | Ile | Leu<br>900 | Lys | Met | Lys | Lys | Met<br>905 | Lys | Lys | Met | Lys | Lys<br>910 | Met | Lys |
| Lys | Met | Lys<br>915 | Lys | Arg | Lys | Lys | Arg<br>920 | Ile |     |     |     |     |     |     |     |

( 2 ) INFORMATION FOR SEQ ID NO:9:

( i ) SEQUENCE CHARACTERISTICS:
        ( A ) LENGTH: 2101 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Plasmodium falciparum ( x i ) SEQUENCE DESCRIPTION: SEQ ID NO:9:

| | | | | | |
|---|---|---|---|---|---|
| GGAACAGGGT | GATAATAAAG | TAGGAGCCTG | TGCTCCGTAT | AGACGATTAC | ATTTATGTGA | 60 |
| TTATAATTTG | GAATCTATAG | ACACAACGTC | GACGACGCAT | AAGTTGTTGT | TAGAGGTGTG | 120 |
| TATGGCAGCA | AAATACGAAG | GAAACTCAAT | AAATACACAT | TATACACAAC | ATCAACGAAC | 180 |
| TAATGAGGAT | TCTGCTTCCC | AATTATGTAC | TGTATTAGCA | CGAAGTTTTG | CAGATATAGG | 240 |
| TGATATCGTA | AGAGGAAAAG | ATCTATATCT | CGGTTATGAT | AATAAAGAAA | AGAACAAAG | 300 |

```
AAAAAAATTA  GAACAGAAAT  TGAAAGATAT  TTTCAAGAAA  ATACATAAGG  ACGTGATGAA    360

GACGAATGGC  GCACAAGAAC  GCTACATAGA  TGATGCCAAA  GGAGGAGATT  TTTTTCAATT    420

AAGAGAAGAT  TGGTGGACGT  CGAATCGAGA  AACAGTATGG  AAAGCATTAA  TATGTCATGC    480

ACCAAAAGAA  GCTAATTATT  TTATAAAAAC  AGCGTGTAAT  GTAGGAAAAG  GAACTAATGG    540

TCAATGCCAT  TGCATTGGTG  GAGATGTTCC  CACATATTTC  GATTATGTGC  CGCAGTATCT    600

TCGCTGGTTC  GAGGAATGGG  CAGAAGACTT  TTGCAGGAAA  AAAAAAAAAA  AACTAGAAAA    660

TTTGCAAAAA  CAGTGTCGTG  ATTACGAACA  AAATTTATAT  TGTAGTGGTA  ATGGCTACGA    720

TTGCACAAAA  ACTATATATA  AAAAGGTAA   ACTTGTTATA  GGTGAACATT  GTACAAACTG    780

TTCTGTTTGG  TGTCGTATGT  ATGAAACTTG  GATAGATAAC  CAGAAAAAG   AATTTCTAAA    840

ACAAAAAGA   AAATACGAAA  CAGAAATATC  AGGTGGTGGT  AGTGGTAAGA  GTCCTAAAAG    900

GACAAAACGG  GCTGCACGTA  GTAGTAGTAG  TAGTGATGAT  AATGGGTATG  AAAGTAAATT    960

TTATAAAAAA  CTGAAAGAAG  TTGGCTACCA  AGATGTCGAT  AAATTTTAA   AAATATTAAA   1020

CAAAGAAGGA  ATATGTCAAA  AACAACCTCA  AGTAGGAAAT  GAAAAGCAG   ATAATGTTGA   1080

TTTTACTAAT  GAAAAATATG  TAAAAACATT  TTCTCGTACA  GAAATTTGTG  AACCGTGCCC   1140

ATGGTGTGGA  TTGGAAAAAG  GTGGTCCACC  ATGGAAAGTT  AAAGGTGACA  AAACCTGCGG   1200

AAGTGCAAAA  ACAAAGACAT  ACGATCCTAA  AAATATTACC  GATATACCAG  TACTCTACCC   1260

TGATAAATCA  CAGCAAAATA  TACTAAAAAA  ATATAAAAAT  TTTTGTGAAA  AAGGTGCACC   1320

TGGTGGTGGT  CAAATTAAAA  AATGGCAATG  TTATTATGAT  GAACATAGGC  CTAGTAGTAA   1380

AAATAATAAT  AATTGTGTAG  AAGGAACATG  GGACAAGTTT  ACACAAGGTA  AACAAACCGT   1440

TAAGTCCTAT  AATGTTTTTT  TTTGGGATTG  GGTTCATGAT  ATGTTACACG  ATTCTGTAGA   1500

GTGGAAGACA  GAACTTAGTA  AGTGTATAAA  TAATAACACT  AATGGCAACA  CATGTAGAAA   1560

CAATAATAAA  TGTAAAACAG  ATTGTGGTTG  TTTTCAAAAA  TGGGTTGAAA  AAAACAACA    1620

AGAATGGATG  GCAATAAAAG  ACCATTTTGG  AAAGCAAACA  GATATTGTCC  AACAAAAAGG   1680

TCTTATCGTA  TTTAGTCCCT  ATGGAGTTCT  TGACCTTGTT  TTGAAGGGCG  GTAATCTGTT   1740

GCAAAATATT  AAAGATGTTC  ATGGAGATAC  AGATGACATA  AAACACATTA  AGAAACTGTT   1800

GGATGAGGAA  GACGCAGTAG  CAGTTGTTCT  TGGTGGCAAG  GACAATACCA  CAATTGATAA   1860

ATTACTACAA  CACGAAAAAG  AACAAGCAGA  ACAATGCAAA  CAAAAGCAGG  AAGAATGCGA   1920

GAAAAAAGCA  CAACAAGAAA  GTCGTGGTCG  CTCCGCCGAA  ACCCGCGAAG  ACGAAAGGAC   1980

ACAACAACCT  GCTGATAGTG  CCGGCGAAGT  CGAAGAAGAA  GAAGACGACG  ACGACTACGA   2040

CGAAGACGAC  GAAGATGACG  ACGTAGTCCA  GGACGTAGAT  GTAAGTGAAA  TAAGAGGTCC   2100

G                                                                      2101
```

( 2 ) INFORMATION FOR SEQ ID NO:10:

( i ) SEQUENCE CHARACTERISTICS:
        ( A ) LENGTH: 700 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: Plasmodium falciparum ( x i ) SEQUENCE DESCRIPTION: SEQ ID NO:10:

```
Glu  Gln  Gly  Asp  Asn  Lys  Val  Gly  Ala  Cys  Ala  Pro  Tyr  Arg  Arg  Leu
 1              5                   10                        15

His  Leu  Cys  Asp  Tyr  Asn  Leu  Glu  Ser  Ile  Asp  Thr  Thr  Ser  Thr  Thr
               20                   25                        30

His  Lys  Leu  Leu  Leu  Glu  Val  Cys  Met  Ala  Ala  Lys  Tyr  Glu  Gly  Asn
          35                        40                   45

Ser  Ile  Asn  Thr  His  Tyr  Thr  Gln  His  Gln  Arg  Thr  Asn  Glu  Asp  Ser
          50                   55                        60

Ala  Ser  Gln  Leu  Cys  Thr  Val  Leu  Ala  Arg  Ser  Phe  Ala  Asp  Ile  Gly
 65                      70                   75                             80

Asp  Ile  Val  Arg  Gly  Lys  Asp  Leu  Tyr  Leu  Gly  Tyr  Asp  Asn  Lys  Glu
                    85                   90                        95

Lys  Glu  Gln  Arg  Lys  Lys  Leu  Glu  Gln  Lys  Leu  Lys  Asp  Ile  Phe  Lys
               100                 105                        110

Lys  Ile  His  Lys  Asp  Val  Met  Lys  Thr  Asn  Gly  Ala  Gln  Glu  Arg  Tyr
          115                      120                       125

Ile  Asp  Asp  Ala  Lys  Gly  Gly  Asp  Phe  Phe  Gln  Leu  Arg  Glu  Asp  Trp
          130                 135                       140

Trp  Thr  Ser  Asn  Arg  Glu  Thr  Val  Trp  Lys  Ala  Leu  Ile  Cys  His  Ala
145                      150                 155                            160

Pro  Lys  Glu  Ala  Asn  Tyr  Phe  Ile  Lys  Thr  Ala  Cys  Asn  Val  Gly  Lys
                    165                      170                            175

Gly  Thr  Asn  Gly  Gln  Cys  His  Cys  Ile  Gly  Gly  Asp  Val  Pro  Thr  Tyr
               180                      185                       190

Phe  Asp  Tyr  Val  Pro  Gln  Tyr  Leu  Arg  Trp  Phe  Glu  Glu  Trp  Ala  Glu
          195                      200                       205

Asp  Phe  Cys  Arg  Lys  Lys  Lys  Lys  Leu  Glu  Asn  Leu  Gln  Lys  Gln
     210                 215                      220

Cys  Arg  Asp  Tyr  Glu  Gln  Asn  Leu  Tyr  Cys  Ser  Gly  Asn  Gly  Tyr  Asp
225                      230                      235                      240

Cys  Thr  Lys  Thr  Ile  Tyr  Lys  Lys  Gly  Lys  Leu  Val  Ile  Gly  Glu  His
                    245                      250                       255

Cys  Thr  Asn  Cys  Ser  Val  Trp  Cys  Arg  Met  Tyr  Glu  Thr  Trp  Ile  Asp
               260                      265                       270

Asn  Gln  Lys  Lys  Glu  Phe  Leu  Lys  Gln  Lys  Arg  Lys  Tyr  Glu  Thr  Glu
          275                      280                       285

Ile  Ser  Gly  Gly  Gly  Ser  Gly  Lys  Ser  Pro  Lys  Arg  Thr  Lys  Arg  Ala
290                      295                      300

Ala  Arg  Ser  Ser  Ser  Ser  Ser  Asp  Asp  Asn  Gly  Tyr  Glu  Ser  Lys  Phe
305                      310                      315                      320

Tyr  Lys  Lys  Leu  Lys  Glu  Val  Gly  Tyr  Gln  Asp  Val  Asp  Lys  Phe  Leu
                    325                      330                       335

Lys  Ile  Leu  Asn  Lys  Glu  Gly  Ile  Cys  Gln  Lys  Gln  Pro  Gln  Val  Gly
               340                      345                       350

Asn  Glu  Lys  Ala  Asp  Asn  Val  Asp  Phe  Thr  Asn  Glu  Lys  Tyr  Val  Lys
          355                      360                       365

Thr  Phe  Ser  Arg  Thr  Glu  Ile  Cys  Glu  Pro  Cys  Pro  Trp  Cys  Gly  Leu
370                      375                      380

Glu  Lys  Gly  Gly  Pro  Pro  Trp  Lys  Val  Lys  Gly  Asp  Lys  Thr  Cys  Gly
385                      390                      395                      400

Ser  Ala  Lys  Thr  Lys  Thr  Tyr  Asp  Pro  Lys  Asn  Ile  Thr  Asp  Ile  Pro
                    405                      410                       415

Val  Leu  Tyr  Pro  Asp  Lys  Ser  Gln  Gln  Asn  Ile  Leu  Lys  Lys  Tyr  Lys
```

|     |     |     |     | 420 |     |     |     | 425 |     |     |     | 430 |     |     |
| --- | --- | --- | --- | --- | --- | --- | --- | --- | --- | --- | --- | --- | --- | --- |
| Asn | Phe | Cys<br>435 | Glu | Lys | Gly | Ala | Pro<br>440 | Gly | Gly | Gly | Gln | Ile<br>445 | Lys | Lys | Trp |
| Gln | Cys<br>450 | Tyr | Tyr | Asp | Glu | His<br>455 | Arg | Pro | Ser | Ser | Lys<br>460 | Asn | Asn | Asn | Asn |
| Cys<br>465 | Val | Glu | Gly | Thr | Trp<br>470 | Asp | Lys | Phe | Thr | Gln<br>475 | Gly | Lys | Gln | Thr | Val<br>480 |
| Lys | Ser | Tyr | Asn | Val<br>485 | Phe | Phe | Trp | Asp | Trp<br>490 | Val | His | Asp | Met | Leu<br>495 | His |
| Asp | Ser | Val | Glu<br>500 | Trp | Lys | Thr | Glu | Leu<br>505 | Ser | Lys | Cys | Ile | Asn<br>510 | Asn | Asn |
| Thr | Asn | Gly<br>515 | Asn | Thr | Cys | Arg | Asn<br>520 | Asn | Asn | Lys | Cys | Lys<br>525 | Thr | Asp | Cys |
| Gly | Cys<br>530 | Phe | Gln | Lys | Trp | Val<br>535 | Glu | Lys | Lys | Gln | Gln<br>540 | Glu | Trp | Met | Ala |
| Ile<br>545 | Lys | Asp | His | Phe | Gly<br>550 | Lys | Gln | Thr | Asp | Ile<br>555 | Val | Gln | Gln | Lys | Gly<br>560 |
| Leu | Ile | Val | Phe | Ser<br>565 | Pro | Tyr | Gly | Val | Leu<br>570 | Asp | Leu | Val | Leu | Lys<br>575 | Gly |
| Gly | Asn | Leu | Leu<br>580 | Gln | Asn | Ile | Lys | Asp<br>585 | Val | His | Gly | Asp | Thr<br>590 | Asp | Asp |
| Ile | Lys | His<br>595 | Ile | Lys | Lys | Leu | Leu<br>600 | Asp | Glu | Glu | Asp | Ala<br>605 | Val | Ala | Val |
| Val | Leu<br>610 | Gly | Gly | Lys | Asp | Asn<br>615 | Thr | Thr | Ile | Asp | Lys<br>620 | Leu | Leu | Gln | His |
| Glu<br>625 | Lys | Glu | Gln | Ala | Glu<br>630 | Gln | Cys | Lys | Gln | Lys<br>635 | Gln | Glu | Glu | Cys | Glu<br>640 |
| Lys | Lys | Ala | Gln | Gln<br>645 | Glu | Ser | Arg | Gly | Arg<br>650 | Ser | Ala | Glu | Thr | Arg<br>655 | Glu |
| Asp | Glu | Arg | Thr<br>660 | Gln | Gln | Pro | Ala | Asp<br>665 | Ser | Ala | Gly | Glu | Val<br>670 | Glu | Glu |
| Glu | Glu | Asp<br>675 | Asp | Asp | Asp | Tyr | Asp<br>680 | Glu | Asp | Asp | Glu | Asp<br>685 | Asp | Asp | Val |
| Val | Gln<br>690 | Asp | Val | Asp | Val | Ser<br>695 | Glu | Ile | Arg | Gly | Pro<br>700 |     |     |     |     |

(2) INFORMATION FOR SEQ ID NO:11:

(i) SEQUENCE CHARACTERISTICS:
  (A) LENGTH: 8220 base pairs
  (B) TYPE: nucleic acid
  (C) STRANDEDNESS: single
  (D) TOPOLOGY: linear (ii) MOLECULE TYPE: DNA (genomic)

(iii) HYPOTHETICAL: NO (vi) ORIGINAL SOURCE:
  (A) ORGANISM: Plasmodium falciparum (xi) SEQUENCE DESCRIPTION: SEQ ID NO:11:

```
AAAAATGGGG CCCAAGGAGG CTGCAGGTGG GGATGATATT GAGGATGAAA GTGCCAAACA        60
TATGTTTGAT AGGATAGGAA AAGATGTGTA CGATAAAGTA AAAGAGGAAG CTAAAGAACG       120
TGGTAAAGGC TTGCAAGGAC GTTTGTCAGA AGCAAAATTT GAGAAAAATG AAAGCGATCC       180
ACAAACACCA GAAGATCCAT GCGATCTTGA TCATAAATAT CATACAAATG TAACTACTAA       240
TGTAATTAAT CCGTGCGCTG ATAGATCTGA CGTGCGTTTT TCCGATGAAT ATGGAGGTCA       300
```

```
ATGTACACAT AATAGAATAA AAGATAGTCA ACAGGGTGAT AATAAAGGTG CATGTGCTCC    360

ATATAGGCGA TTGCATGTAT GCGATCAAAA TTTAGAACAG ATAGAGCCTA TAAAATAAC     420

AAATACTCAT AATTTATTGG TAGATGTGTG TATGGCAGCA AAATTTGAAG GACAATCAAT    480

AACACAAGAT TATCCAAAAT ATCAAGCAAC ATATGGTGAT TCTCCTTCTC AAATATGTAC    540

TATGCTGGCA CGAAGTTTTG CGGACATAGG GGACATTGTC AGAGGAAGAG ATTTGTATTT    600

AGGTAATCCA CAAGAAATAA AACAAAGACA ACAATTAGAA ATAATTTGA AACAATTTT     660

CGGGAAAATA TATGAAAAAT TGAATGGCGC AGAAGCACGC TACGAAATG ATCCGGAATT     720

TTTTAAATTA CGAGAAGATT GGTGGACTGC TAATCGAGAA ACAGTATGGA AAGCCATCAC   780

ATGTAACGCT TGGGGTAATA CATATTTTCA TGCAACGTGC AATAGAGGAG AACGAACTAA   840

AGGTTACTGC CGGTGTAACG ACGACCAAGT TCCCACATAT TTTGATTATG TGCCGCAGTA   900

TCTTCGCTGG TTCGAGGAAT GGGCAGAAGA TTTTTGTAGG AAAAAAAATA AAAAATAAA    960

AGATGTTAAA AGAAATTGTC GTGGAAAAGA TAAAGAGGAT AAGGATCGAT ATTGTAGCCG  1020

TAATGGCTAC GATTGCGAAA AAACTAAACG AGCGATTGGT AAGTTGCGTT ATGGTAAGCA  1080

ATGCATTAGC TGTTTGTATG CATGTAATCC TTACGTTGAT TGGATAAATA ACCAAAAAGA  1140

ACAATTTGAC AAACAGAAAA AAAATATGA TGAAGAAATA AAAAATATG AAAATGGAGC    1200

ATCAGGTGGT AGTAGGCAAA AACGGGATGC AGGTGGTACA ACTACTACTA ATTATGATGG  1260

ATATGAAAAA AAATTTTATG ACGAACTTAA TAAAAGTGAA TATAGAACCG TTGATAAATT  1320

TTTGGAAAAA TTAAGTAATG AAGAAATATG CACAAAAGTT AAAGACGAAG AAGGAGGAAC  1380

AATTGATTTT AAAAACGTTA ATAGTGATAG TACTAGTGGT GCTAGTGGCA CTAATGTTGA  1440

AAGTCAAGGA ACATTTTATC GTTCAAAATA TTGCCAACCC TGCCCTTATT GTGGAGTGAA  1500

AAAGGTAAAT AATGGTGGTA GTAGTAATGA ATGGGAAGAG AAAAATAATG GCAAGTGCAA  1560

GAGTGGAAAA CTTTATGAGC CTAAACCCGA CAAAGAAGGT ACTACTATTA CAATCCTTAA  1620

AAGTGGTAAA GGACATGATG ATATTGAAGA AAAATTAAAC AAATTTTGTG ATGAAAAAA   1680

TGGTGATACA ATAAATAGTG GTGGTAGTGG TACGGGTGGT AGTGGTGGTG GTAACAGTGG  1740

TAGACAGGAA TTGTATGAAG AATGGAAATG TTATAAAGGT GAAGATGTAG TGAAAGTTGG  1800

ACACGATGAG GATGACGAGG AGGATTATGA AAATGTAAAA AATGCAGGCG GATTATGTAT  1860

ATTAAAAAAC CAAAAAAAGA ATAAAGAAGA AGGTGGAAAT ACGTCTGAAA AGGAGCCTGA  1920

TGAAATCCAA AAGACATTCA ATCCTTTTTT TTACTATTGG GTTGCACATA TGTTAAAGA   1980

TTCCATACAT TGGAAAAAAA AACTTCAGAG ATGTTTACAA ATGGTAACA GAATAAAATG   2040

TGGAAACAAT AAATGTAATA ATGATTGTGA ATGTTTTAAA AGATGGATTA CACAAAAAAA  2100

AGACGAATGG GGGAAAATAG TACAACATTT TAAAACGCAA AATATTAAAG GTAGAGGAGG  2160

TAGTGACAAT ACGGCAGAAT TAATCCCATT TGATCACGAT TATGTTCTTC AATACAATTT  2220

GCAAGAAGAA TTTTTGAAAG GCGATTCCGA AGACGCTTCC GAAGAAAAAT CCGAAAATAG  2280

TCTGGATGCA GAGGAGGCAG AGGAACTAAA ACACCTTCGC GAAATCATTG AAAGTGAAGA  2340

CAATAATCAA GAAGCATCTG TTGGTGGTGG CGTCACTGAA CAAAAAAATA TAATGGATAA  2400

ATTGCTCAAC TACGAAAAAG ACGAAGCCGA TTTATGCCTA GAAATTCACG AAGATGAGGA  2460

AGAGGAAAAA GAAAAAGGAG ACGGAAACGA ATGTATCGAA GAGGGCGAAA ATTTTCGTTA  2520

TAATCCATGT AGTGGCGAAA GTGGTAACAA ACGATACCCC GTTCTTGCGA ACAAAGTAGC  2580

GTATCAAATG CATCACAAGG CAAAGACACA ATTGGCTAGT CGTGCTGGTA GAAGTGCGTT  2640

GAGAGGTGAT ATATCCTTAG CGCAATTTAA AAATGGTCGT AACGGAAGTA CATTGAAAGG  2700
```

-continued

| | | | | | | |
|---|---|---|---|---|---|---|
| ACAAATTTGC | AAAATTAACG | AAAACTATTC | CAATGATAGT | CGTGGTAATA | GTGGTGGACC | 2760 |
| ATGTACAGGC | AAAGATGGAG | ATCACGGAGG | TGTGCGCATG | AGAATAGGAA | CGGAATGGTC | 2820 |
| AAATATTGAA | GGAAAAAAAC | AAACGTCATA | CAAAAACGTC | TTTTTACCTC | CCCGACGAGA | 2880 |
| ACACATGTGT | ACATCCAATT | TAGAAAATTT | AGATGTTGGT | AGTGTCACTA | AAAATGATAA | 2940 |
| GGCTAGCCAC | TCATTATTGG | GAGATGTTCA | GCTCGCAGCA | AAAACTGATG | CAGCTGAGAT | 3000 |
| AATAAAACGC | TATAAAGATC | AAAATAATAT | ACAACTAACT | GATCCAATAC | AACAAAAAGA | 3060 |
| CCAGGAGGCT | ATGTGTCGAG | CTGTACGTTA | TAGTTTTGCC | GATTAGGAG | ACATTATTCG | 3120 |
| AGGAAGAGAT | ATGTGGGATG | AGGATAAGAG | CTCAACAGAC | ATGGAAACAC | GTTTGATAAC | 3180 |
| CGTATTTAAA | AACATTAAAG | AAAAACATGA | TGGAATCAAA | GACAACCCTA | AATATACCGG | 3240 |
| TGATGAAAGC | AAAAAGCCCG | CATATAAAAA | ATTACGAGCA | GATTGGTGGG | AAGCAAATAG | 3300 |
| ACATCAAGTG | TGGAGAGCCA | TGAAATGCGC | AACAAAGGC | ATCATATGTC | CTGGTATGCC | 3360 |
| AGTTGACGAT | TATATCCCCC | AACGTTTACG | CTGGATGACT | GAATGGGCTG | AATGGTATTG | 3420 |
| TAAAGCGCAA | TCACAGGAGT | ATGACAAGTT | AAAAAAAATC | TGTGCAGATT | GTATGAGTAA | 3480 |
| GGGTGATGGA | AAATGTACGC | AAGGTGATGT | CGATTGTGGA | AAGTGCAAAG | CAGCATGTGA | 3540 |
| TAAATATAAA | GAGGAAATAG | AAAATGGAA | TGAACAATGG | AGAAAAATAT | CAGATAAATA | 3600 |
| CAATCTATTA | TACCTACAAG | CAAAAACTAC | TTCTACTAAT | CCTGGCCGTA | CTGTTCTTGG | 3660 |
| TGATGACGAT | CCCGACTATC | AACAAATGGT | AGATTTTTG | ACCCCAATAC | ACAAAGCAAG | 3720 |
| TATTGCCGCA | CGTGTTCTTG | TTAAACGTGC | TGCTGGTAGT | CCCACTGAGA | TCGCCGCCGC | 3780 |
| CGCCCCGATC | ACCCCCTACA | GTACTGCTGC | CGGATATATA | CACCAGGAAA | TAGGATATGG | 3840 |
| GGGGTGCCAG | GAACAAACAC | AATTTTGTGA | AAAAAAACAT | GGTGCAACAT | CAACTAGTAC | 3900 |
| CACGAAAGAA | AACAAGAAT | ACACCTTTAA | ACAACCTCCG | CCGGAGTATG | CTACAGCGTG | 3960 |
| TGATTGCATA | AATAGGTCGC | AAACAGAGGA | GCCGAAGAAA | AAGGAAGAAA | ATGTAGAGAG | 4020 |
| TGCCTGCAAA | ATAGTGGAGA | AAATACTTGA | GGGTAAGAAT | GGAAGGACTA | CAGTAGGTGA | 4080 |
| ATGTAATCCA | AAAGAGAGTT | ATCCTGATTG | GGATTGCAAA | AACAATATTG | ACATTAGTCA | 4140 |
| TGATGGTGCT | TGTATGCCTC | CAAGGAGACA | AAAACTATGT | TTATATTATA | TAGCACATGA | 4200 |
| GAGTCAAACA | GAAAATATAA | AAACAGACGA | TAATTTGAAA | GATGCTTTTA | TTAAAACTGC | 4260 |
| AGCAGCAGAA | ACTTTTCTTT | CATGGCAATA | TTATAAGAGT | AAGAATGATA | GTGAAGCTAA | 4320 |
| AATATTAGAT | AGAGGCCTTA | TTCCATCCCA | ATTTTTAAGA | TCCATGATGT | ACACGTTTGG | 4380 |
| AGATTATAGA | GATATATGTT | TGAACACAGA | TATATCTAAA | AAACAAATG | ATGTAGCTAA | 4440 |
| GGCAAAAGAT | AAAATAGGTA | AATTTTTCTC | AAAAGATGGC | AGCAAATCTC | CTAGTGGCTT | 4500 |
| ATCACGCCAA | GAATGGTGGA | AAACAAATGG | TCCAGAGATT | TGGAAAGGAA | TGTTATGTGC | 4560 |
| CTTAACAAAA | TACGTCACAG | ATACCGATAA | CAAAGAAAA | ATCAAAACG | ACTACTCATA | 4620 |
| CGATAAAGTC | AACCAATCCC | AAAATGGCAA | CCCTTCCCTT | GAAGAGTTTG | CTGCTAAACC | 4680 |
| TCAATTTCTA | CGTTGGATGA | TCGAATGGGG | AGAAGAGTTT | TGTGCTGAAC | GTCAGAAGAA | 4740 |
| GGAAAATATC | ATAAAAGATG | CATGTAATGA | AATAAATTCT | ACACAACAGT | GTAATGATGC | 4800 |
| GAAACATCGT | TGTAATCAAG | CATGTAGAGC | ATATCAAGAA | TATGTTGAAA | ATAAAAAAAA | 4860 |
| AGAATTTTCG | GGACAAACAA | ATAACTTTGT | TCTAAAGGCA | AATGTTCAGC | CCCAAGATCC | 4920 |
| AGAATATAAA | GGATATGAAT | ATAAAGACGG | CGTACAACCG | ATACAGGGA | ATGAGTATTT | 4980 |
| ACTGCAAAAA | TGTGATAATA | ATAAATGTTC | TTGCATGGAT | GGAAATGTAC | TTTCCGTCTC | 5040 |
| TCCAAAAGAA | AAACCTTTTG | GAAAATATGC | CCATAAATAT | CCTGAGAAAT | GTGATTGTTA | 5100 |

```
TCAAGGAAAA CATGTACCTA GCATACCACC TCCCCCCCCA CCTGTACAAC CACAACCGGA    5160
AGCACCAACA GTAACAGTAG ACGTTTGCAG CATAGTAAAA ACACTATTTA AAGACACAAA    5220
CAATTTTTCC GACGCTTGTG GTCTAAAATA CGGCAAAACC GCACCATCCA GTTGGAAATG    5280
TATACCAAGT GACACAAAAA GTGGTGCTGG TGCCACCACC GGCAAAAGTG GTAGTGATAG    5340
TGGTAGTATT TGTATCCCAC CCAGGAGGCG ACGATTATAT GTGGGGAAAC TACAGGAGTG    5400
GGCTACCGCG CTCCCACAAG GTGAGGGCGC CGCGCCGTCC CACTCACGCG CCGACGACTT    5460
GCGCAATGCG TTCATCCAAT CTGCTGCAAT AGAGACTTTT TTCTTATGGG ATAGATATAA    5520
AGAAGAGAAA AAACCACAGG GTGATGGGTC ACAACAAGCA CTATCACAAC TAACCAGTAC    5580
ATACAGTGAT GACGAGGAGG ACCCCCCCGA CAAACTGTTA CAAAATGGTA AGATACCCCC    5640
CGATTTTTTG AGATTAATGT TCTATACATT AGGAGATTAT AGGGATATTT TAGTACACGG    5700
TGGTAACACA AGTGACAGTG GTAACACAAA TGGTAGTAAC AACAACAATA TTGTGCTTGA    5760
AGCGAGTGGT AACAAGGAGG ACATGCAAAA AATACAAGAG AAAATAGAAC AAATTCTCCC    5820
AAAAAATGGT GGCACACCTC TTGTCCCAAA ATCTAGTGCC CAAACACCTG ATAAATGGTG    5880
GAATGAACAC GCCGAATCTA TCTGGAAAGG TATGATATGT GCATTGACAT ATACAGAAAA    5940
GAACCCTGAC ACCAGTGCAA GAGGCGACGA AAACAAAATA GAAAGGATG ATGAAGTGTA     6000
CGAGAAATTT TTTGGCAGCA CAGCCGACAA ACATGGCACA GCCTCAACCC CAACCGGCAC    6060
ATACAAAACC CAATACGACT ACGAAAAAGT CAAACTTGAG GATACAAGTG GTGCCAAAAC    6120
CCCCTCAGCC TCTAGTGATA CACCCCTTCT CTCCGATTTC GTGTTACGCC CCCCCTACTT    6180
CCGTTACCTT GAAGAATGGG GTCAAAATTT TTGTAAAAAA AGAAAGCATA AATTGGCACA    6240
AATAAAACAT GAGTGTAAAG TAGAAGAAAA TGGTGGTGGT AGTCGTCGTG GTGGTATAAC    6300
AAGACAATAT AGTGGGGATG GCGAAGCGTG TAATGAGATG CTTCCAAAAA ACGATGGAAC    6360
TGTTCCGGAT TTAGAAAAGC CGAGTTGTGC CAAACCTTGT AGTTCTTATA GAAAATGGAT    6420
AGAAAGCAAG GGAAAAGAGT TTGAGAAACA AGAAAAGGCA TATGAACAAC AAAAAGACAA    6480
ATGTGTAAAT GGAAGTAATA AGCATGATAA TGGATTTTGT GAAACACTAA CAACGTCCTC    6540
TAAAGCTAAA GACTTTTTAA AAACGTTAGG ACCATGTAAA CCTAATAATG TAGAGGGTAA    6600
AACAATTTTT GATGATGATA AAACCTTTAA ACATACAAAA GATTGTGATC CATGTCTTAA    6660
ATTTAGTGTT AATTGTAAAA AAGATGAATG TGATAATTCT AAAGGAACCG ATTGCCGAAA    6720
TAAAAATAGT ATTGATGCAA CAGATATTGA AAATGGAGTG GATTCTACTG TACTAGAAAT    6780
GCGTGTCAGT GCTGATAGTA AAAGTGGATT TAATGGTGAT GGTTTAGAGA ATGCTTGTAG    6840
AGGTGCTGGT ATCTTTGAAG GTATTAGAAA AGATGAATGG AAATGTCGTA ATGTATGTGG    6900
TTATGTTGTA TGTAAACCGG AAAACGTTAA TGGGGAAGCA AAGGGAAAAC ACATTATACA    6960
AATTAGAGCA CTGGTTAAAC GTTGGGTAGA ATATTTTTT GAAGATTATA ATAAAATAAA     7020
ACATAAAATT TCACATCGCA TAAAAAATGG TGAAATATCT CCATGTATAA AAAATTGTGT    7080
AGAAAAATGG GTAGATCAGA AAAGAAAAGA ATGGAAGGAA ATTACTGAAC GTTTCAAAGA    7140
TCAATATAAA AATGACAATT CAGATGATGA CAATGTGAGA AGTTTTTTGG AGACCTTGAT    7200
ACCTCAAATT ACTGATGCAA ACGCTAAAAA TAAGGTTATA AAATTAAGTA AGTTCGGTAA    7260
TTCTTGTGGA TGTAGTGCCA GTGCGAACGA ACAAAACAAA AATGGTGAAT ACAAGGACGC    7320
TATAGATTGT ATGCTTAAAA AGCTTAAAGA TAAAATTGGC GAGTGCGAAA AGAAACACCA    7380
TCAAACTAGT GATACCGAGT GTTCCGACAC ACCACAACCG CAAACCCTTG AAGACGAAAC    7440
TTTGGATGAT GATATAGAAA CAGAGGAGGC GAAGAAGAAC ATGATGCCGA AAATTTGTGA    7500
```

```
AAATGTGTTA  AAAACAGCAC  AACAAGAGGA  TGAAGGCGGT  TGTGTCCCAG  CAGAAAATAG    7560

TGAAGAACCG  GCAGCAACAG  ATAGTGGTAA  GGAAACCCCC  GAACAAACCC  CCGTTCTCAA    7620

ACCCGAAGAA  GAAGCAGTAC  CGGAACCACC  ACCTCCACCC  CCACAGGAAA  AAGCCCCGGC    7680

ACCAATACCC  CAACCACAAC  CACCAACCCC  CCCCACACAA  CTCTTGGATA  ATCCCACGT     7740

TCTAACCGCC  CTGGTGACCT  CCACCCTCGC  CTGGAGCGTT  GGCATCGGTT  TTGCTACATT    7800

CACTTATTTT  TATCTAAAGG  TAAATGGAAG  TATATATATG  GGGATGTGGA  TGTATGTGGA    7860

TGTATGTGAA  TGTATGTGGA  TGTATGTGGA  TGTATGTGGA  TGTGTTTTAT  GGATATGTAT    7920

TTGTGATTAT  GTTTGGATAT  ATATATATAT  ATATATATGT  TTATGTATAT  GTGTTTTTGG    7980

ATATATATAT  GTGTATGTAT  ATGATTTTCT  GTATATGTAT  TTGTGGGTTA  AGGATATATA    8040

TATATGGATG  TACTTGTATG  TGTTTTATAT  ATATATTTTA  TATATATGTA  TTTATATTAA    8100

AAAAGAAATA  TAAAACAAA   TTTATTAAAA  TGAAAAAAAG  AAAAATGAAA  TATAAAAAAA    8160

AATTTATTAA  AATAAAAAAA  AAAAAAAAAA  AAAAGGAGAA  AAATTTTTA   AAAAATAATA    8220
```

( 2 ) INFORMATION FOR SEQ ID NO:12:

( i ) SEQUENCE CHARACTERISTICS:
        ( A ) LENGTH: 2710 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: Plasmodium falciparum ( x i ) SEQUENCE DESCRIPTION: SEQ ID NO:12:

```
Asn  Val  Met  Val  Glu  Leu  Ala  Lys  Met  Gly  Pro  Lys  Glu  Ala  Ala  Gly
 1              5                   10                  15

Gly  Asp  Asp  Ile  Glu  Asp  Glu  Ser  Ala  Lys  His  Met  Phe  Asp  Arg  Ile
              20                  25                  30

Gly  Lys  Asp  Val  Tyr  Asp  Lys  Val  Lys  Glu  Glu  Ala  Lys  Glu  Arg  Gly
         35                  40                  45

Lys  Gly  Leu  Gln  Gly  Arg  Leu  Ser  Glu  Ala  Lys  Phe  Glu  Lys  Asn  Glu
     50                  55                  60

Ser  Asp  Pro  Gln  Thr  Pro  Glu  Asp  Pro  Cys  Asp  Leu  Asp  His  Lys  Tyr
65                  70                  75                  80

His  Thr  Asn  Val  Thr  Thr  Asn  Val  Ile  Asn  Pro  Cys  Ala  Asp  Arg  Ser
                85                  90                  95

Asp  Val  Arg  Phe  Ser  Asp  Glu  Tyr  Gly  Gly  Gln  Cys  Thr  His  Asn  Arg
              100                 105                 110

Ile  Lys  Asp  Ser  Gln  Gln  Gly  Asp  Asn  Lys  Gly  Ala  Cys  Ala  Pro  Tyr
         115                 120                 125

Arg  Arg  Leu  His  Val  Cys  Asp  Gln  Asn  Leu  Glu  Gln  Ile  Glu  Pro  Ile
     130                 135                 140

Lys  Ile  Thr  Asn  Thr  His  Asn  Leu  Leu  Val  Asp  Val  Cys  Met  Ala  Ala
145                 150                 155                 160

Lys  Phe  Glu  Gly  Gln  Ser  Ile  Thr  Gln  Asp  Tyr  Pro  Lys  Tyr  Gln  Ala
              165                 170                 175

Thr  Tyr  Gly  Asp  Ser  Pro  Ser  Gln  Ile  Cys  Thr  Met  Leu  Ala  Arg  Ser
              180                 185                 190

Phe  Ala  Asp  Ile  Gly  Asp  Ile  Val  Arg  Gly  Arg  Asp  Leu  Tyr  Leu  Gly
```

```
                      195                          200                          205
    Asn  Pro  Gln  Glu  Ile  Lys  Gln  Arg  Gln  Leu  Glu  Asn  Asn  Leu  Lys
         210                      215                      220
    Thr  Ile  Phe  Gly  Lys  Ile  Tyr  Glu  Lys  Leu  Asn  Gly  Ala  Glu  Ala  Arg
    225                      230                      235                           240
    Tyr  Gly  Asn  Asp  Pro  Glu  Phe  Phe  Lys  Leu  Arg  Glu  Asp  Trp  Trp  Thr
                        245                      250                      255
    Ala  Asn  Arg  Glu  Thr  Val  Trp  Lys  Ala  Ile  Thr  Cys  Asn  Ala  Trp  Gly
                   260                      265                      270
    Asn  Thr  Tyr  Phe  His  Ala  Thr  Cys  Asn  Arg  Gly  Glu  Arg  Thr  Lys  Gly
              275                      280                      285
    Tyr  Cys  Arg  Cys  Asn  Asp  Asp  Gln  Val  Pro  Thr  Tyr  Phe  Asp  Tyr  Val
         290                      295                      300
    Pro  Gln  Tyr  Leu  Arg  Trp  Phe  Glu  Glu  Trp  Ala  Glu  Asp  Phe  Cys  Arg
    305                      310                      315                           320
    Lys  Lys  Asn  Lys  Lys  Ile  Lys  Asp  Val  Lys  Arg  Asn  Cys  Arg  Gly  Lys
                        325                      330                           335
    Asp  Lys  Glu  Asp  Lys  Asp  Arg  Tyr  Cys  Ser  Arg  Asn  Gly  Tyr  Asp  Cys
                   340                      345                      350
    Glu  Lys  Thr  Lys  Arg  Ala  Ile  Gly  Lys  Leu  Arg  Tyr  Gly  Lys  Gln  Cys
              355                      360                      365
    Ile  Ser  Cys  Leu  Tyr  Ala  Cys  Asn  Pro  Tyr  Val  Asp  Trp  Ile  Asn  Asn
         370                      375                      380
    Gln  Lys  Glu  Gln  Phe  Asp  Lys  Gln  Lys  Lys  Tyr  Asp  Glu  Glu  Ile
    385                      390                      395                           400
    Lys  Lys  Tyr  Glu  Asn  Gly  Ala  Ser  Gly  Ser  Arg  Gln  Lys  Arg  Asp
                        405                      410                           415
    Ala  Gly  Gly  Thr  Thr  Thr  Thr  Asn  Tyr  Asp  Gly  Tyr  Glu  Lys  Lys  Phe
                   420                      425                      430
    Tyr  Asp  Glu  Leu  Asn  Lys  Ser  Glu  Tyr  Arg  Thr  Val  Asp  Lys  Phe  Leu
              435                      440                      445
    Glu  Lys  Leu  Ser  Asn  Glu  Glu  Ile  Cys  Thr  Lys  Val  Lys  Asp  Glu  Glu
         450                      455                      460
    Gly  Gly  Thr  Ile  Asp  Phe  Lys  Asn  Val  Asn  Ser  Asp  Ser  Thr  Ser  Gly
    465                      470                      475                           480
    Ala  Ser  Gly  Thr  Asn  Val  Glu  Ser  Gln  Gly  Thr  Phe  Tyr  Arg  Ser  Lys
                        485                      490                           495
    Tyr  Cys  Gln  Pro  Cys  Pro  Tyr  Cys  Gly  Val  Lys  Lys  Val  Asn  Asn  Gly
                   500                      505                      510
    Gly  Ser  Ser  Asn  Glu  Trp  Glu  Glu  Lys  Asn  Asn  Gly  Lys  Cys  Lys  Ser
              515                      520                      525
    Gly  Lys  Leu  Tyr  Glu  Pro  Lys  Pro  Asp  Lys  Glu  Gly  Thr  Thr  Ile  Thr
         530                      535                      540
    Ile  Leu  Lys  Ser  Gly  Lys  Gly  His  Asp  Asp  Ile  Glu  Glu  Lys  Leu  Asn
    545                      550                      555                           560
    Lys  Phe  Cys  Asp  Glu  Lys  Asn  Gly  Asp  Thr  Ile  Asn  Ser  Gly  Gly  Ser
                        565                      570                           575
    Gly  Thr  Gly  Gly  Ser  Gly  Gly  Gly  Asn  Ser  Gly  Arg  Gln  Glu  Leu  Tyr
                   580                      585                      590
    Glu  Glu  Trp  Lys  Cys  Tyr  Lys  Gly  Glu  Asp  Val  Val  Lys  Val  Gly  His
              595                      600                      605
    Asp  Glu  Asp  Asp  Glu  Glu  Asp  Tyr  Glu  Asn  Val  Lys  Asn  Ala  Gly  Gly
         610                      615                      620
```

```
Leu Cys Ile Leu Lys Asn Gln Lys Lys Asn Lys Glu Glu Gly Gly Asn
625                 630                 635                 640

Thr Ser Glu Lys Glu Pro Asp Glu Ile Gln Lys Thr Phe Asn Pro Phe
                645                 650                 655

Phe Tyr Tyr Trp Val Ala His Met Leu Lys Asp Ser Ile His Trp Lys
            660                 665                 670

Lys Lys Leu Gln Arg Cys Leu Gln Asn Gly Asn Arg Ile Lys Cys Gly
        675                 680                 685

Asn Asn Lys Cys Asn Asn Asp Cys Glu Cys Phe Lys Arg Trp Ile Thr
    690                 695                 700

Gln Lys Lys Asp Glu Trp Gly Lys Ile Val Gln His Phe Lys Thr Gln
705                 710                 715                 720

Asn Ile Lys Gly Arg Gly Gly Ser Asp Asn Thr Ala Glu Leu Ile Pro
                725                 730                 735

Phe Asp His Asp Tyr Val Leu Gln Tyr Asn Leu Gln Glu Glu Phe Leu
            740                 745                 750

Lys Gly Asp Ser Glu Asp Ala Ser Glu Glu Lys Ser Glu Asn Ser Leu
        755                 760                 765

Asp Ala Glu Glu Ala Glu Glu Leu Lys His Leu Glu Arg Glu Ile Ile Glu
    770                 775                 780

Ser Glu Asp Asn Asn Gln Glu Ala Ser Val Gly Gly Gly Val Thr Glu
785                 790                 795                 800

Gln Lys Asn Ile Met Asp Lys Leu Leu Asn Tyr Glu Lys Asp Glu Ala
                805                 810                 815

Asp Leu Cys Leu Glu Ile His Glu Asp Glu Glu Glu Glu Lys Glu Lys
            820                 825                 830

Gly Asp Gly Asn Glu Cys Ile Glu Glu Gly Glu Asn Phe Arg Tyr Asn
        835                 840                 845

Pro Cys Ser Gly Glu Ser Gly Asn Lys Arg Tyr Pro Val Leu Ala Asn
    850                 855                 860

Lys Val Ala Tyr Gln Met His His Lys Ala Lys Thr Gln Leu Ala Ser
865                 870                 875                 880

Arg Ala Gly Arg Ser Ala Leu Arg Gly Asp Ile Ser Leu Ala Gln Phe
                885                 890                 895

Lys Asn Gly Arg Asn Gly Ser Thr Leu Lys Gly Gln Ile Cys Lys Ile
            900                 905                 910

Asn Glu Asn Tyr Ser Asn Asp Ser Arg Gly Asn Ser Gly Gly Pro Cys
        915                 920                 925

Thr Gly Lys Asp Gly Asp His Gly Gly Val Arg Met Arg Ile Gly Thr
    930                 935                 940

Glu Trp Ser Asn Ile Glu Gly Lys Lys Gln Thr Ser Tyr Lys Asn Val
945                 950                 955                 960

Phe Leu Pro Pro Arg Arg Glu His Met Cys Thr Ser Asn Leu Glu Asn
                965                 970                 975

Leu Asp Val Gly Ser Val Thr Lys Asn Asp Lys Ala Ser His Ser Leu
            980                 985                 990

Leu Gly Asp Val Gln Leu Ala Ala Lys Thr Asp Ala Ala Glu Ile Ile
        995                 1000                1005

Lys Arg Tyr Lys Asp Gln Asn Asn Ile Gln Leu Thr Asp Pro Ile Gln
    1010                1015                1020

Gln Lys Asp Gln Glu Ala Met Cys Arg Ala Val Arg Tyr Ser Phe Ala
1025                1030                1035                1040

Asp Leu Gly Asp Ile Ile Arg Gly Arg Asp Met Trp Asp Glu Asp Lys
                1045                1050                1055
```

Ser Ser Thr Asp Met Glu Thr Arg Leu Ile Thr Val Phe Lys Asn Ile
                1060                1065                1070

Lys Glu Lys His Asp Gly Ile Lys Asp Asn Pro Lys Tyr Thr Gly Asp
            1075                1080                1085

Glu Ser Lys Lys Pro Ala Tyr Lys Lys Leu Arg Ala Asp Trp Trp Glu
        1090                1095                1100

Ala Asn Arg His Gln Val Trp Arg Ala Met Lys Cys Ala Thr Lys Gly
1105                1110                1115                1120

Ile Ile Cys Pro Gly Met Pro Val Asp Asp Tyr Ile Pro Gln Arg Leu
                1125                1130                1135

Arg Trp Met Thr Glu Trp Ala Glu Trp Tyr Cys Lys Ala Gln Ser Gln
                1140                1145                1150

Glu Tyr Asp Lys Leu Lys Lys Ile Cys Ala Asp Cys Met Ser Lys Gly
                1155                1160                1165

Asp Gly Lys Cys Thr Gln Gly Asp Val Asp Cys Gly Lys Cys Lys Ala
        1170                1175                1180

Ala Cys Asp Lys Tyr Lys Glu Glu Ile Glu Lys Trp Asn Glu Gln Trp
1185                1190                1195                1200

Arg Lys Ile Ser Asp Lys Tyr Asn Leu Leu Tyr Leu Gln Ala Lys Thr
                1205                1210                1215

Thr Ser Thr Asn Pro Gly Arg Thr Val Leu Gly Asp Asp Pro Asp
                1220                1225                1230

Tyr Gln Gln Met Val Asp Phe Leu Thr Pro Ile His Lys Ala Ser Ile
            1235                1240                1245

Ala Ala Arg Val Leu Val Lys Arg Ala Ala Gly Ser Pro Thr Glu Ile
        1250                1255                1260

Ala Ala Ala Ala Pro Ile Thr Pro Tyr Ser Thr Ala Ala Gly Tyr Ile
1265                1270                1275                1280

His Gln Glu Ile Gly Tyr Gly Gly Cys Gln Glu Gln Thr Gln Phe Cys
                1285                1290                1295

Glu Lys Lys His Gly Ala Thr Ser Thr Ser Thr Thr Lys Glu Asn Lys
            1300                1305                1310

Glu Tyr Thr Phe Lys Gln Pro Pro Pro Glu Tyr Ala Thr Ala Cys Asp
            1315                1320                1325

Cys Ile Asn Arg Ser Gln Thr Glu Glu Pro Lys Lys Lys Glu Glu Asn
        1330                1335                1340

Val Glu Ser Ala Cys Lys Ile Val Glu Lys Ile Leu Glu Gly Lys Asn
1345                1350                1355                1360

Gly Arg Thr Thr Val Gly Glu Cys Asn Pro Lys Glu Ser Tyr Pro Asp
                1365                1370                1375

Trp Asp Cys Lys Asn Asn Ile Asp Ile Ser His Asp Gly Ala Cys Met
            1380                1385                1390

Pro Pro Arg Arg Gln Lys Leu Cys Leu Tyr Tyr Ile Ala His Glu Ser
        1395                1400                1405

Gln Thr Glu Asn Ile Lys Thr Asp Asp Asn Leu Lys Asp Ala Phe Ile
        1410                1415                1420

Lys Thr Ala Ala Ala Glu Thr Phe Leu Ser Trp Gln Tyr Tyr Lys Ser
1425                1430                1435                1440

Lys Asn Asp Ser Glu Ala Lys Ile Leu Asp Arg Gly Leu Ile Pro Ser
                1445                1450                1455

Gln Phe Leu Arg Ser Met Met Tyr Thr Phe Gly Asp Tyr Arg Asp Ile
                1460                1465                1470

Cys Leu Asn Thr Asp Ile Ser Lys Lys Gln Asn Asp Val Ala Lys Ala

```
            1475                    1480                        1485
Lys  Asp  Lys  Ile  Gly  Lys  Phe  Phe  Ser  Lys  Asp  Gly  Ser  Lys  Ser  Pro
          1490                    1495                    1500

Ser  Gly  Leu  Ser  Arg  Gln  Glu  Trp  Trp  Lys  Thr  Asn  Gly  Pro  Glu  Ile
1505                    1510                    1515                        1520

Trp  Lys  Gly  Met  Leu  Cys  Ala  Leu  Thr  Lys  Tyr  Val  Thr  Asp  Thr  Asp
                    1525                    1530                    1535

Asn  Lys  Arg  Lys  Ile  Lys  Asn  Asp  Tyr  Ser  Tyr  Asp  Lys  Val  Asn  Gln
                    1540                    1545                    1550

Ser  Gln  Asn  Gly  Asn  Pro  Ser  Leu  Glu  Glu  Phe  Ala  Ala  Lys  Pro  Gln
          1555                    1560                    1565

Phe  Leu  Arg  Trp  Met  Ile  Glu  Trp  Gly  Glu  Glu  Phe  Cys  Ala  Glu  Arg
          1570                    1575                    1580

Gln  Lys  Lys  Glu  Asn  Ile  Ile  Lys  Asp  Ala  Cys  Asn  Glu  Ile  Asn  Ser
1585                    1590                    1595                        1600

Thr  Gln  Gln  Cys  Asn  Asp  Ala  Lys  His  Arg  Cys  Asn  Gln  Ala  Cys  Arg
                    1605                    1610                    1615

Ala  Tyr  Gln  Glu  Tyr  Val  Glu  Asn  Lys  Lys  Lys  Glu  Phe  Ser  Gly  Gln
                    1620                    1625                    1630

Thr  Asn  Asn  Phe  Val  Leu  Lys  Ala  Asn  Val  Gln  Pro  Gln  Asp  Pro  Glu
                    1635                    1640                    1645

Tyr  Lys  Gly  Tyr  Glu  Tyr  Lys  Asp  Gly  Val  Gln  Pro  Ile  Gln  Gly  Asn
          1650                    1655                    1660

Glu  Tyr  Leu  Leu  Gln  Lys  Cys  Asp  Asn  Lys  Cys  Ser  Cys  Met  Asp
1665                    1670                    1675                        1680

Gly  Asn  Val  Leu  Ser  Val  Ser  Pro  Lys  Glu  Lys  Pro  Phe  Gly  Lys  Tyr
                    1685                    1690                    1695

Ala  His  Lys  Tyr  Pro  Glu  Lys  Cys  Asp  Cys  Tyr  Gln  Gly  Lys  His  Val
                    1700                    1705                    1710

Pro  Ser  Ile  Pro  Pro  Pro  Pro  Pro  Val  Gln  Pro  Gln  Pro  Glu  Ala
          1715                    1720                    1725

Pro  Thr  Val  Thr  Val  Asp  Val  Cys  Ser  Ile  Val  Lys  Thr  Leu  Phe  Lys
          1730                    1735                    1740

Asp  Thr  Asn  Asn  Phe  Ser  Asp  Ala  Cys  Gly  Leu  Lys  Tyr  Gly  Lys  Thr
1745                    1750                    1755                        1760

Ala  Pro  Ser  Ser  Trp  Lys  Cys  Ile  Pro  Ser  Asp  Thr  Lys  Ser  Gly  Ala
                    1765                    1770                    1775

Gly  Ala  Thr  Thr  Gly  Lys  Ser  Gly  Ser  Asp  Ser  Gly  Ser  Ile  Cys  Ile
                    1780                    1785                    1790

Pro  Pro  Arg  Arg  Arg  Arg  Leu  Tyr  Val  Gly  Lys  Leu  Gln  Glu  Trp  Ala
                    1795                    1800                    1805

Thr  Ala  Leu  Pro  Gln  Gly  Glu  Gly  Ala  Ala  Pro  Ser  His  Ser  Arg  Ala
          1810                    1815                    1820

Asp  Asp  Leu  Arg  Asn  Ala  Phe  Ile  Gln  Ser  Ala  Ala  Ile  Glu  Thr  Phe
1825                    1830                    1835                        1840

Phe  Leu  Trp  Asp  Arg  Tyr  Lys  Glu  Glu  Lys  Lys  Pro  Gln  Gly  Asp  Gly
                    1845                    1850                    1855

Ser  Gln  Gln  Ala  Leu  Ser  Gln  Leu  Thr  Ser  Thr  Tyr  Ser  Asp  Asp  Glu
                    1860                    1865                    1870

Glu  Asp  Pro  Pro  Asp  Lys  Leu  Leu  Gln  Asn  Gly  Lys  Ile  Pro  Pro  Asp
                    1875                    1880                    1885

Phe  Leu  Arg  Leu  Met  Phe  Tyr  Thr  Leu  Gly  Asp  Tyr  Arg  Asp  Ile  Leu
          1890                    1895                    1900
```

```
Val His Gly Gly Asn Thr Ser Asp Ser Gly Asn Thr Asn Gly Ser Asn
1905                1910                1915                1920

Asn Asn Asn Ile Val Leu Glu Ala Ser Gly Asn Lys Glu Asp Met Gln
            1925                1930                1935

Lys Ile Gln Glu Lys Ile Glu Gln Ile Leu Pro Lys Asn Gly Gly Thr
        1940                1945                1950

Pro Leu Val Pro Lys Ser Ser Ala Gln Thr Pro Asp Lys Trp Trp Asn
        1955                1960                1965

Glu His Ala Glu Ser Ile Trp Lys Gly Met Ile Cys Ala Leu Thr Tyr
        1970                1975                1980

Thr Glu Lys Asn Pro Asp Thr Ser Ala Arg Gly Asp Glu Asn Lys Ile
1985                1990                1995                2000

Glu Lys Asp Asp Glu Val Tyr Glu Lys Phe Phe Gly Ser Thr Ala Asp
            2005                2010                2015

Lys His Gly Thr Ala Ser Thr Pro Thr Gly Thr Tyr Lys Thr Gln Tyr
            2020                2025                2030

Asp Tyr Glu Lys Val Lys Leu Glu Asp Thr Ser Gly Ala Lys Thr Pro
        2035                2040                2045

Ser Ala Ser Ser Asp Thr Pro Leu Leu Ser Asp Phe Val Leu Arg Pro
        2050                2055                2060

Pro Tyr Phe Arg Tyr Leu Glu Glu Trp Gly Gln Asn Phe Cys Lys Lys
2065                2070                2075                2080

Arg Lys His Lys Leu Ala Gln Ile Lys His Glu Cys Lys Val Glu Glu
                2085                2090                2095

Asn Gly Gly Gly Ser Arg Arg Gly Gly Ile Thr Arg Gln Tyr Ser Gly
                2100                2105                2110

Asp Gly Glu Ala Cys Asn Glu Met Leu Pro Lys Asn Asp Gly Thr Val
            2115                2120                2125

Pro Asp Leu Glu Lys Pro Ser Cys Ala Lys Pro Cys Ser Ser Tyr Arg
        2130                2135                2140

Lys Trp Ile Glu Ser Lys Gly Lys Glu Phe Glu Lys Gln Glu Lys Ala
2145                2150                2155                2160

Tyr Glu Gln Gln Lys Asp Lys Cys Val Asn Gly Ser Asn Lys His Asp
                2165                2170                2175

Asn Gly Phe Cys Glu Thr Leu Thr Thr Ser Ser Lys Ala Lys Asp Phe
            2180                2185                2190

Leu Lys Thr Leu Gly Pro Cys Lys Pro Asn Asn Val Glu Gly Lys Thr
        2195                2200                2205

Ile Phe Asp Asp Asp Lys Thr Phe Lys His Thr Lys Asp Cys Asp Pro
        2210                2215                2220

Cys Leu Lys Phe Ser Val Asn Cys Lys Lys Asp Glu Cys Asp Asn Ser
2225                2230                2235                2240

Lys Gly Thr Asp Cys Arg Asn Lys Asn Ser Ile Asp Ala Thr Asp Ile
            2245                2250                2255

Glu Asn Gly Val Asp Ser Thr Val Leu Glu Met Arg Val Ser Ala Asp
            2260                2265                2270

Ser Lys Ser Gly Phe Asn Gly Asp Gly Leu Glu Asn Ala Cys Arg Gly
            2275                2280                2285

Ala Gly Ile Phe Glu Gly Ile Arg Lys Asp Glu Trp Lys Cys Arg Asn
            2290                2295                2300

Val Cys Gly Tyr Val Val Cys Lys Pro Glu Asn Val Asn Gly Glu Ala
2305                2310                2315                2320

Lys Gly Lys His Ile Ile Gln Ile Arg Ala Leu Val Lys Arg Trp Val
                2325                2330                2335
```

Glu Tyr Phe Phe Glu Asp Tyr Asn Lys Ile Lys His Lys Ile Ser His
                2340                2345               2350

Arg Ile Lys Asn Gly Glu Ile Ser Pro Cys Ile Lys Asn Cys Val Glu
            2355            2360            2365

Lys Trp Val Asp Gln Lys Arg Lys Glu Trp Lys Glu Ile Thr Glu Arg
        2370            2375            2380

Phe Lys Asp Gln Tyr Lys Asn Asp Asn Ser Asp Asp Asn Val Arg
2385            2390            2395                        2400

Ser Phe Leu Glu Thr Leu Ile Pro Gln Ile Thr Asp Ala Asn Ala Lys
                2405            2410                2415

Asn Lys Val Ile Lys Leu Ser Lys Phe Gly Asn Ser Cys Gly Cys Ser
            2420            2425            2430

Ala Ser Ala Asn Glu Gln Asn Lys Asn Gly Glu Tyr Lys Asp Ala Ile
            2435            2440            2445

Asp Cys Met Leu Lys Lys Leu Lys Asp Lys Ile Gly Glu Cys Glu Lys
        2450            2455            2460

Lys His His Gln Thr Ser Asp Thr Glu Cys Ser Asp Thr Pro Gln Pro
2465            2470            2475            2480

Gln Thr Leu Glu Asp Glu Thr Leu Asp Asp Asp Ile Glu Thr Glu Glu
                2485            2490            2495

Ala Lys Lys Asn Met Met Pro Lys Ile Cys Glu Asn Val Leu Lys Thr
                2500            2505            2510

Ala Gln Gln Glu Asp Glu Gly Gly Cys Val Pro Ala Glu Asn Ser Glu
            2515            2520            2525

Glu Pro Ala Ala Thr Asp Ser Gly Lys Glu Thr Pro Glu Gln Thr Pro
        2530            2535            2540

Val Leu Lys Pro Glu Glu Glu Ala Val Pro Glu Pro Pro Pro Pro
2545            2550            2555            2560

Pro Gln Glu Lys Ala Pro Ala Pro Ile Pro Gln Pro Gln Pro Pro Thr
            2565            2570            2575

Pro Pro Thr Gln Leu Leu Asp Asn Pro His Val Leu Thr Ala Leu Val
            2580            2585            2590

Thr Ser Thr Leu Ala Trp Ser Val Gly Ile Gly Phe Ala Thr Phe Thr
            2595            2600            2605

Tyr Phe Tyr Leu Lys Val Asn Gly Ser Ile Tyr Met Gly Met Trp Met
2610            2615            2620

Tyr Val Asp Val Cys Glu Cys Met Trp Met Tyr Val Asp Val Cys Gly
2625            2630            2635            2640

Cys Val Leu Trp Ile Cys Ile Cys Asp Tyr Val Trp Ile Tyr Ile Tyr
                2645            2650            2655

Ile Tyr Ile Cys Leu Cys Ile Cys Val Phe Gly Tyr Ile Tyr Val Tyr
            2660            2665            2670

Val Tyr Asp Phe Leu Tyr Met Tyr Leu Trp Val Lys Asp Ile Tyr Ile
        2675            2680            2685

Trp Met Tyr Leu Tyr Val Phe Tyr Ile Tyr Ile Leu Tyr Ile Cys Ile
        2690            2695            2700

Tyr Ile Lys Lys Glu Ile
2705            2710

( 2 ) INFORMATION FOR SEQ ID NO:13:

( i ) SEQUENCE CHARACTERISTICS:
        ( A ) LENGTH: 291 amino acids
        ( B ) TYPE: amino acid
        ( C ) STRANDEDNESS: single (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:13:

| Cys | Xaa | Xaa | Xaa | Xaa | Xaa | Xaa | Xaa | Xaa | Xaa | Xaa | Xaa | Xaa | Cys | Xaa | Xaa |
|---|---|---|---|---|---|---|---|---|---|---|---|---|---|---|---|
| 1 | | | | 5 | | | | | 10 | | | | | 15 | |
| Xaa | Xaa | Xaa | Val | Cys | Ile | Pro | Asp | Arg | Arg | Tyr | Gln | Leu | Cys | Met | Lys |
| | | | 20 | | | | | 25 | | | | | 30 | | |
| Glu | Leu | Xaa | Xaa | Xaa | Xaa | Xaa | Xaa | Xaa | Xaa | Xaa | Xaa | Xaa | Xaa | Xaa | Xaa |
| | | 35 | | | | | 40 | | | | | 45 | | | |
| Xaa | Xaa | Xaa | Xaa | Xaa | Xaa | Xaa | Xaa | Xaa | Xaa | Xaa | Xaa | Xaa | Xaa | Xaa | Xaa |
| | 50 | | | | | 55 | | | | | 60 | | | | |
| Xaa | Xaa | Xaa | Xaa | Xaa | Xaa | Xaa | Xaa | Xaa | Xaa | Xaa | Xaa | Xaa | Xaa | Xaa | Xaa |
| 65 | | | | | 70 | | | | | 75 | | | | | 80 |
| Xaa | Asp | Phe | Cys | Lys | Asp | Ile | Arg | Trp | Ser | Leu | Gly | Asp | Phe | Gly | Asp |
| | | | | 85 | | | | | 90 | | | | | 95 | |
| Ile | Ile | Met | Gly | Thr | Asp | Met | Glu | Gly | Ile | Gly | Tyr | Ser | Lys | Xaa | Xaa |
| | | | 100 | | | | | 105 | | | | | 110 | | |
| Xaa | Xaa | Xaa | Xaa | Xaa | Xaa | Xaa | Xaa | Xaa | Thr | Asp | Glu | Lys | Ala | Gln | Gln |
| | | | 115 | | | | | 120 | | | | | 125 | | |
| Arg | Arg | Lys | Gln | Trp | Trp | Asn | Glu | Ser | Lys | Ala | Gln | Ile | Trp | Thr | Ala |
| | 130 | | | | | 135 | | | | | 140 | | | | |
| Met | Met | Tyr | Ser | Val | Xaa | Xaa | Xaa | Xaa | Xaa | Xaa | Xaa | Xaa | Xaa | Xaa | Xaa |
| 145 | | | | | 150 | | | | | 155 | | | | | 160 |
| Cys | Xaa | Xaa | Xaa | Xaa | Xaa | Xaa | Xaa | Xaa | Glu | Pro | Gln | Ile | Tyr | Arg | Trp |
| | | | | 165 | | | | | 170 | | | | | 175 | |
| Ile | Arg | Glu | Trp | Gly | Arg | Asp | Tyr | Val | Ser | Glu | Leu | Pro | Thr | Glu | Val |
| | | | 180 | | | | | 185 | | | | | 190 | | |
| Gln | Lys | Leu | Lys | Glu | Lys | Cys | Xaa | Xaa | Xaa | Xaa | Xaa | Xaa | Xaa | Xaa | Xaa |
| | | | 195 | | | | | 200 | | | | | 205 | | |
| Xaa | Xaa | Cys | Xaa | Val | Pro | Pro | Cys | Gln | Asn | Ala | Cys | Lys | Ser | Tyr | Asp |
| | 210 | | | | | 215 | | | | | 220 | | | | |
| Gln | Trp | Ile | Thr | Arg | Lys | Lys | Asn | Xaa | Xaa | Xaa | Xaa | Xaa | Xaa | Xaa | Xaa |
| 225 | | | | | 230 | | | | | 235 | | | | | 240 |
| Xaa | Xaa | Xaa | Xaa | Xaa | Xaa | Xaa | Xaa | Xaa | Xaa | Xaa | Xaa | Xaa | Xaa | Xaa | Xaa |
| | | | | 245 | | | | | 250 | | | | | 255 | |
| Xaa | Xaa | Xaa | Xaa | Xaa | Xaa | Xaa | Xaa | Xaa | Xaa | Xaa | Xaa | Xaa | Xaa | Xaa | Xaa |
| | | | 260 | | | | | 265 | | | | | 270 | | |
| Xaa | Xaa | Xaa | Xaa | Xaa | Xaa | Xaa | Xaa | Xaa | Xaa | Xaa | Xaa | Xaa | Xaa | Xaa | Xaa |
| | | | 275 | | | | | 280 | | | | | 285 | | |
| Cys | Xaa | Cys | | | | | | | | | | | | | |
| | | 290 | | | | | | | | | | | | | |

(2) INFORMATION FOR SEQ ID NO:14:

(i) SEQUENCE CHARACTERISTICS:
(A) LENGTH: 271 amino acids
(B) TYPE: amino acid
(C) STRANDEDNESS: single
(D) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:14:

| Cys | Xaa | Xaa | Xaa | Xaa | Xaa | Xaa | Xaa | Xaa | Xaa | Xaa | Cys | Xaa | Xaa | Xaa | Xaa |
|---|---|---|---|---|---|---|---|---|---|---|---|---|---|---|---|
| 1 |   |   |   | 5 |   |   |   |   |   | 10 |   |   |   | 15 |   |
| Xaa | Xaa | Xaa | Xaa | Xaa | Val | Cys | Ile | Pro | Asp | Arg | Arg | Ile | Gln | Leu | Cys |
|   |   |   | 20 |   |   |   |   | 25 |   |   |   |   | 30 |   |   |
| Ile | Val | Asn | Leu | Xaa | Xaa | Xaa | Xaa | Xaa | Xaa | Xaa | Xaa | Xaa | Xaa | Xaa | Xaa |
|   |   |   | 35 |   |   |   |   | 40 |   |   |   |   | 45 |   |   |
| Xaa | Xaa | Xaa | Xaa | Xaa | Xaa | Xaa | Xaa | Xaa | Xaa | Xaa | Xaa | Xaa | Xaa | Xaa | Xaa |
|   |   |   | 50 |   |   |   |   | 55 |   |   |   |   | 60 |   |   |
| Xaa | Xaa | Xaa | Xaa | Xaa | Xaa | Xaa | Xaa | Lys | Phe | Cys | Asn | Asp | Leu | Lys | Asn |
| 65 |   |   |   |   |   | 70 |   |   |   | 75 |   |   |   |   | 80 |
| Ser | Phe | Leu | Asp | Tyr | Gly | His | Leu | Ala | Met | Gly | Asn | Asp | Met | Asp | Phe |
|   |   |   |   | 85 |   |   |   |   | 90 |   |   |   |   | 95 |   |
| Gly | Gly | Tyr | Ser | Thr | Xaa | Xaa | Xaa | Xaa | Xaa | Xaa | Xaa | Xaa | Xaa | Xaa | Xaa |
|   |   |   | 100 |   |   |   |   | 105 |   |   |   |   | 110 |   |   |
| Xaa | Xaa | Xaa | Xaa | Xaa | Xaa | Ser | Glu | His | Lys | Ile | Lys | Asn | Phe | Arg | Lys |
|   |   |   | 115 |   |   |   |   | 120 |   |   |   |   | 125 |   |   |
| Glu | Trp | Trp | Asn | Glu | Phe | Arg | Glu | Lys | Leu | Trp | Glu | Ala | Met | Leu | Ser |
|   |   | 130 |   |   |   |   | 135 |   |   |   |   | 140 |   |   |   |
| Glu | His | Xaa | Xaa | Xaa | Xaa | Xaa | Xaa | Cys | Xaa | Xaa | Xaa | Xaa | Xaa | Xaa | Glu |
| 145 |   |   |   |   |   | 150 |   |   |   |   |   | 155 |   |   | 160 |
| Leu | Gln | Ile | Thr | Gln | Trp | Ile | Lys | Glu | Trp | His | Gly | Glu | Phe | Leu | Leu |
|   |   |   |   |   | 165 |   |   |   |   | 170 |   |   |   |   | 175 |
| Glu | Arg | Asp | Asn | Arg | Ser | Lys | Leu | Pro | Lys | Ser | Lys | Cys | Xaa | Xaa | Xaa |
|   |   |   | 180 |   |   |   |   | 185 |   |   |   |   | 190 |   |   |
| Xaa | Xaa | Xaa | Xaa | Xaa | Cys | Xaa | Glu | Lys | Glu | Cys | Ile | Asp | Pro | Cys | Met |
|   |   |   | 195 |   |   |   |   | 200 |   |   |   |   | 205 |   |   |
| Lys | Tyr | Arg | Asp | Trp | Ile | Ile | Arg | Ser | Lys | Phe | Xaa | Xaa | Xaa | Xaa | Xaa |
|   |   | 210 |   |   |   |   | 215 |   |   |   |   | 220 |   |   |   |
| Xaa | Xaa | Xaa | Xaa | Xaa | Xaa | Xaa | Xaa | Xaa | Xaa | Xaa | Xaa | Xaa | Xaa | Xaa | Xaa |
| 225 |   |   |   |   |   | 230 |   |   |   |   |   | 235 |   |   | 240 |
| Xaa | Xaa | Xaa | Xaa | Xaa | Xaa | Xaa | Xaa | Xaa | Xaa | Xaa | Xaa | Xaa | Xaa | Xaa | Xaa |
|   |   |   |   | 245 |   |   |   |   | 250 |   |   |   |   | 255 |   |
| Xaa | Xaa | Xaa | Xaa | Cys | Xaa | Xaa | Xaa | Xaa | Xaa | Xaa | Xaa | Cys | Xaa | Cys |   |
|   |   |   | 260 |   |   |   |   | 265 |   |   |   |   | 270 |   |   |

( 2 ) INFORMATION FOR SEQ ID NO:15:

( i ) SEQUENCE CHARACTERISTICS:
        ( A ) LENGTH: 277 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:15:

| | | | | | | | | | | | | | | | |
|---|---|---|---|---|---|---|---|---|---|---|---|---|---|---|---|
| Cys | Xaa | Xaa | Xaa | Xaa | Xaa | Xaa | Xaa | Xaa | Xaa | Xaa | Xaa | Xaa | Xaa | Cys | Xaa |
| 1 | | | | 5 | | | | | 10 | | | | | 15 | |
| Xaa | Xaa | Xaa | Xaa | Xaa | Xaa | Xaa | Xaa | Xaa | Val | Cys | Val | Pro | Pro | Arg | Arg |
| | | | 20 | | | | | 25 | | | | | 30 | | |
| Gln | Glu | Leu | Cys | Leu | Gly | Asn | Ile | Xaa | Xaa | Xaa | Xaa | Xaa | Xaa | Xaa | Xaa |
| | | 35 | | | | | 40 | | | | | | 45 | | |
| Xaa | Xaa | Xaa | Xaa | Xaa | Xaa | Xaa | Xaa | Xaa | Xaa | Xaa | Xaa | Xaa | Xaa | Xaa | Xaa |
| | 50 | | | | | 55 | | | | | | 60 | | | |
| Xaa | Xaa | Xaa | Xaa | Xaa | Xaa | Xaa | Xaa | Xaa | Xaa | Xaa | Xaa | Glu | Val | Cys | Lys |
| 65 | | | | | 70 | | | | | 75 | | | | | 80 |
| Ile | Ile | Asn | Lys | Thr | Phe | Ala | Asp | Ile | Arg | Asp | Ile | Ile | Gly | Gly | Thr |
| | | | | 85 | | | | | 90 | | | | | 95 | |
| Asp | Tyr | Trp | Asn | Asp | Leu | Ser | Asn | Arg | Xaa | Xaa | Xaa | Xaa | Xaa | Xaa | Xaa |
| | | | 100 | | | | | 105 | | | | | 110 | | |
| Xaa | Xaa | Xaa | Xaa | Xaa | Xaa | Xaa | Xaa | Asn | Lys | Lys | Asn | Asp | Lys | Leu | Phe |
| | | 115 | | | | | 120 | | | | | 125 | | | |
| Arg | Asp | Glu | Trp | Trp | Lys | Val | Ile | Lys | Lys | Asp | Val | Trp | Asn | Val | Ile |
| | 130 | | | | 135 | | | | | 140 | | | | | |
| Ser | Trp | Phe | Xaa | Xaa | Xaa | Xaa | Cys | Xaa | Xaa | Xaa | Xaa | Xaa | Xaa | Xaa | Xaa |
| 145 | | | | | 150 | | | | | 155 | | | | | 160 |
| Ile | Pro | Gln | Phe | Phe | Arg | Trp | Phe | Ser | Glu | Trp | Gly | Asp | Asp | Tyr | Cys |
| | | | | 165 | | | | | 170 | | | | | 175 | |
| Gln | Asp | Lys | Thr | Lys | Met | Ile | Glu | Thr | Leu | Lys | Val | Glu | Cys | Xaa | Xaa |
| | | | 180 | | | | | 185 | | | | | 190 | | |
| Xaa | Xaa | Cys | Xaa | Asp | Asp | Asn | Cys | Lys | Ser | Lys | Cys | Asn | Ser | Tyr | Lys |
| | | 195 | | | | | 200 | | | | | 205 | | | |
| Glu | Trp | Ile | Ser | Lys | Lys | Lys | Lys | Xaa | Xaa | Xaa | Xaa | Xaa | Xaa | Xaa | Xaa |
| | | | 210 | | | | 215 | | | | | 220 | | | |
| Xaa | Xaa | Xaa | Xaa | Xaa | Xaa | Xaa | Xaa | Xaa | Xaa | Xaa | Xaa | Xaa | Xaa | Xaa | Xaa |
| 225 | | | | | 230 | | | | | 235 | | | | | 240 |
| Xaa | Xaa | Xaa | Xaa | Xaa | Xaa | Xaa | Xaa | Xaa | Xaa | Xaa | Xaa | Cys | Xaa | Xaa | Xaa |
| | | | | 245 | | | | | 250 | | | | | 255 | |
| Xaa | Xaa | Xaa | Xaa | Xaa | Xaa | Xaa | Xaa | Xaa | Xaa | Xaa | Xaa | Xaa | Xaa | Xaa | Xaa |
| | | | 260 | | | | | 265 | | | | | 270 | | |
| Xaa | Cys | Xaa | Xaa | Cys | | | | | | | | | | | |
| | | 275 | | | | | | | | | | | | | |

( 2 ) INFORMATION FOR SEQ ID NO:16:

( i ) SEQUENCE CHARACTERISTICS:
        ( A ) LENGTH: 282 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:16:

Cys Xaa Xaa Xaa Xaa Xaa Xaa Xaa Xaa Xaa Xaa Xaa Xaa Cys Xaa Xaa

```
  1                   5                             10                              15
Xaa  Xaa  Xaa  Xaa  Xaa  Xaa  Xaa  Xaa  Xaa  Val  Cys  Gly  Pro  Pro  Arg  Arg
               20                   25                   30

Gln  Gln  Leu  Cys  Leu  Gly  Tyr  Ile  Xaa  Xaa  Xaa  Xaa  Xaa  Xaa  Xaa  Xaa
               35                   40                   45

Xaa  Xaa  Xaa  Xaa  Xaa  Xaa  Xaa  Xaa  Xaa  Xaa  Xaa  Xaa  Xaa  Xaa  Xaa  Xaa
     50                             55                   60

Xaa  Xaa  Xaa  Xaa  Xaa  Xaa  Xaa  Xaa  Xaa  Xaa  Xaa  Xaa  Lys  Ile  Cys  Asn
65                        70                        75                        80

Ala  Ile  Leu  Gly  Ser  Tyr  Ala  Asp  Ile  Gly  Asp  Ile  Val  Arg  Gly  Leu
               85                   90                   95

Asp  Val  Trp  Arg  Asp  Ile  Asn  Thr  Asn  Xaa  Xaa  Xaa  Xaa  Xaa  Xaa  Xaa
               100                  105                  110

Xaa  Xaa  Xaa  Xaa  Xaa  Xaa  Xaa  Xaa  Xaa  Xaa  Lys  Lys  Gln  Asn  Asp  Asn
               115                  120                  125

Asn  Glu  Arg  Asn  Lys  Trp  Trp  Glu  Lys  Gln  Arg  Asn  Leu  Ile  Trp  Ser
     130                            135                  140

Ser  Met  Val  Lys  His  Ile  Xaa  Xaa  Xaa  Xaa  Xaa  Cys  Xaa  Xaa  Xaa  Xaa
145                       150                  155                            160

Xaa  Xaa  Xaa  Xaa  Ile  Pro  Gln  Phe  Leu  Arg  Trp  Leu  Lys  Glu  Trp  Gly
               165                  170                  175

Asp  Glu  Phe  Cys  Glu  Glu  Met  Gly  Thr  Glu  Val  Lys  Gln  Leu  Glu  Lys
               180                  185                  190

Ile  Cys  Xaa  Xaa  Xaa  Xaa  Cys  Xaa  Glu  Lys  Lys  Cys  Lys  Asn  Ala  Cys
               195                  200                  205

Ser  Ser  Tyr  Glu  Lys  Trp  Ile  Lys  Glu  Arg  Lys  Asn  Xaa  Xaa  Xaa  Xaa
     210                            215                  220

Xaa  Xaa  Xaa  Xaa  Xaa  Xaa  Xaa  Xaa  Xaa  Xaa  Xaa  Xaa  Xaa  Xaa  Xaa  Xaa
225                       230                  235                            240

Xaa  Xaa  Xaa  Xaa  Xaa  Xaa  Xaa  Xaa  Xaa  Xaa  Xaa  Xaa  Xaa  Xaa  Xaa  Xaa
               245                  250                            255

Xaa  Xaa  Cys  Xaa  Xaa  Xaa  Xaa  Xaa  Xaa  Xaa  Xaa  Xaa  Xaa  Xaa  Xaa  Xaa
               260                  265                            270

Xaa  Xaa  Xaa  Xaa  Xaa  Xaa  Cys  Xaa  Xaa  Cys
               275                  280
```

(2) INFORMATION FOR SEQ ID NO:17:

(i) SEQUENCE CHARACTERISTICS:
        (A) LENGTH: 324 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:17:

```
Cys  Xaa  Xaa  Xaa  Xaa  Xaa  Xaa  Xaa  Xaa  Xaa  Xaa  Cys  Xaa  Xaa  Xaa  Xaa
1                         5                        10                        15

Xaa  Xaa  Xaa  Xaa  Xaa  Xaa  Xaa  Ala  Cys  Ile  Pro  Pro  Arg  Arg  Gln  Lys
               20                   25                   30
```

| Leu | Cys | Leu | His | Tyr | Leu | Xaa | Xaa | Xaa | Xaa | Xaa | Xaa | Xaa | Xaa | Xaa |
|-----|-----|-----|-----|-----|-----|-----|-----|-----|-----|-----|-----|-----|-----|-----|
|     |     | 35  |     |     |     | 40  |     |     |     |     |     | 45  |     |     |
| Xaa | Xaa | Xaa | Xaa | Xaa | Xaa | Xaa | Xaa | Xaa | Xaa | Xaa | Xaa | Xaa | Xaa | Xaa |
|     |     | 50  |     |     |     | 55  |     |     |     |     |     | 60  |     |     |
| Xaa | Xaa | Xaa | Xaa | Xaa | Xaa | Xaa | Xaa | Xaa | Xaa | Xaa | Xaa | Xaa | Xaa | Xaa |
| 65  |     |     |     |     | 70  |     |     |     |     | 75  |     |     |     | 80  |
| Xaa | Xaa | Xaa | Xaa | Xaa | Xaa | Xaa | Xaa | Xaa | Asp | Phe | Lys | Arg | Gln | Met | Phe |
|     |     |     |     | 85  |     |     |     |     | 90  |     |     |     | 95  |     |     |
| Tyr | Thr | Phe | Ala | Asp | Tyr | Arg | Asp | Ile | Cys | Leu | Gly | Thr | Asp | Ile | Ser |
|     |     |     | 100 |     |     |     |     | 105 |     |     |     |     | 110 |     |     |
| Ser | Lys | Lys | Asp | Thr | Ser | Xaa | Xaa | Xaa | Xaa | Xaa | Xaa | Xaa | Xaa | Xaa |
|     |     | 115 |     |     |     | 120 |     |     |     |     |     | 125 |     |     |
| Xaa | Xaa | Xaa | Xaa | Xaa | Lys | Ile | Ser | Asn | Ser | Ile | Arg | Tyr | Arg | Lys | Ser |
|     |     | 130 |     |     |     |     | 135 |     |     |     |     | 140 |     |     |     |
| Trp | Trp | Glu | Thr | Asn | Gly | Pro | Val | Ile | Trp | Glu | Gly | Met | Leu | Cys | Ala |
| 145 |     |     |     |     | 150 |     |     |     |     | 155 |     |     |     |     | 160 |
| Leu | Xaa | Xaa | Xaa | Xaa | Xaa | Xaa | Xaa | Xaa | Xaa | Xaa | Xaa | Xaa | Xaa | Xaa |
|     |     |     |     | 165 |     |     |     |     |     | 170 |     |     |     | 175 |
| Xaa | Xaa | Xaa | Xaa | Xaa | Xaa | Xaa | Xaa | Xaa | Xaa | Xaa | Xaa | Xaa | Xaa | Xaa |
|     |     |     | 180 |     |     |     |     |     | 185 |     |     |     | 190 |     |
| Xaa | Xaa | Xaa | Xaa | Xaa | Xaa | Xaa | Xaa | Xaa | Xaa | Xaa | Arg | Pro | Gln | Phe | Leu |
|     |     |     |     | 195 |     |     |     |     | 200 |     |     |     | 205 |     |     |
| Arg | Trp | Leu | Thr | Glu | Trp | Gly | Glu | Asn | Phe | Cys | Lys | Glu | Gln | Lys | Lys |
|     | 210 |     |     |     |     | 215 |     |     |     |     | 220 |     |     |     |     |
| Glu | Tyr | Lys | Val | Leu | Leu | Ala | Lys | Cys | Xaa | Xaa | Xaa | Xaa | Xaa | Xaa |
| 225 |     |     |     |     | 230 |     |     |     |     | 235 |     |     |     | 240 |
| Xaa | Xaa | Xaa | Xaa | Cys | Xaa | Xaa | Xaa | Cys | Val | Ala | Cys | Lys | Asp | Gln | Cys |
|     |     |     | 245 |     |     |     |     | 250 |     |     |     |     | 255 |     |     |
| Lys | Gln | Tyr | His | Ser | Trp | Ile | Gly | Ile | Trp | Ile | Asp | Xaa | Xaa | Xaa | Xaa |
|     |     |     | 260 |     |     |     |     | 265 |     |     |     |     | 270 |     |     |
| Xaa | Xaa | Xaa | Xaa | Xaa | Xaa | Xaa | Xaa | Xaa | Xaa | Xaa | Xaa | Xaa | Xaa | Xaa |
|     |     | 275 |     |     |     |     | 280 |     |     |     |     | 285 |     |     |
| Xaa | Xaa | Xaa | Xaa | Xaa | Xaa | Xaa | Xaa | Xaa | Xaa | Xaa | Xaa | Xaa | Xaa | Xaa |
|     | 290 |     |     |     |     | 295 |     |     |     |     | 300 |     |     |     |
| Xaa | Xaa | Xaa | Xaa | Xaa | Xaa | Cys | Xaa | Xaa | Xaa | Xaa | Xaa | Xaa | Xaa | Xaa | Cys |
| 305 |     |     |     |     | 310 |     |     |     |     | 315 |     |     |     |     | 320 |
| Xaa | Xaa | Xaa | Cys |

( 2 ) INFORMATION FOR SEQ ID NO:18:

( i ) SEQUENCE CHARACTERISTICS:
        ( A ) LENGTH: 362 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:18:

| Ala | Cys | Ala | Pro | Tyr | Arg | Arg | Leu | His | Leu | Cys | Asp | Tyr | Asn | Leu | Xaa |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| | | | | | | | | | | | | | | |
|---|---|---|---|---|---|---|---|---|---|---|---|---|---|---|
| Xaa | Xaa | Xaa | Xaa<br>20 | Xaa | Xaa | Xaa | Xaa | Xaa | Xaa<br>25 | Xaa | Xaa | Xaa | Xaa<br>30 | Xaa |
| Xaa | Xaa | Xaa<br>35 | Xaa | Xaa | Xaa | Xaa | Xaa<br>40 | Xaa | Xaa | Xaa | Xaa | Xaa<br>45 | Xaa | Xaa |
| Xaa | Xaa<br>50 | Xaa | Xaa | Xaa | Xaa | Xaa<br>55 | Xaa | Xaa | Xaa | Gln | Leu<br>60 | Cys | Thr | Val | Leu |
| Ala<br>65 | Arg | Ser | Phe | Ala | Asp<br>70 | Ile | Gly | Asp | Ile | Val<br>75 | Arg | Gly | Lys | Asp | Leu<br>80 |
| Tyr | Leu | Gly | Tyr | Asp<br>85 | Asn | Lys | Xaa | Xaa | Xaa<br>90 | Xaa | Xaa | Xaa | Xaa | Xaa<br>95 |
| Xaa | Xaa | Xaa | Xaa<br>100 | Xaa | Xaa | Xaa | Xaa | Xaa<br>105 | Xaa | Xaa | Xaa | Xaa | Xaa<br>110 | Xaa |
| Xaa | Xaa | Xaa | Xaa | Xaa<br>115 | Xaa | Xaa | Xaa | Xaa | Xaa<br>120 | Xaa | Xaa | Lys<br>125 | Gly | Gly | Asp |
| Phe | Phe<br>130 | Gln | Leu | Arg | Glu | Asp<br>135 | Trp | Trp | Thr | Ser | Asn<br>140 | Arg | Glu | Thr | Val |
| Trp<br>145 | Lys | Ala | Leu | Ile | Cys<br>150 | His | Ala | Xaa | Xaa | Xaa<br>155 | Xaa | Xaa | Xaa | Xaa<br>160 |
| Xaa | Xaa | Xaa | Cys<br>165 | Xaa | Xaa | Xaa | Xaa | Xaa<br>170 | Xaa | Xaa | Xaa | Xaa<br>175 | Xaa |
| Xaa | Xaa | Xaa | Xaa<br>180 | Xaa | Xaa | Xaa | Xaa | Xaa | Xaa<br>185 | Val | Pro | Gln | Tyr<br>190 | Leu |
| Arg | Trp | Phe<br>195 | Glu | Glu | Trp | Ala | Glu<br>200 | Asp | Phe | Cys | Arg | Lys<br>205 | Lys | Lys | Lys |
| Lys | Leu<br>210 | Glu | Asn | Leu | Gln | Lys<br>215 | Gln | Cys | Xaa | Xaa | Xaa<br>220 | Xaa | Xaa | Cys |
| Xaa<br>225 | Xaa | Xaa | Xaa | Xaa | Xaa<br>230 | Xaa | Xaa | Xaa | Xaa | Xaa<br>235 | Xaa | Xaa | Xaa | Cys<br>240 |
| Thr | Asn | Cys | Ser | Val<br>245 | Trp | Cys | Arg | Met | Tyr<br>250 | Glu | Thr | Trp | Ile | Asp<br>255 | Asn |
| Gln | Lys | Lys | Xaa<br>260 | Xaa | Xaa | Xaa | Xaa<br>265 | Xaa | Xaa | Xaa | Xaa | Xaa<br>270 | Xaa |
| Xaa | Xaa | Xaa<br>275 | Xaa | Xaa | Xaa | Xaa | Xaa<br>280 | Xaa | Xaa | Xaa | Xaa | Xaa<br>285 | Xaa | Xaa |
| Xaa | Xaa<br>290 | Xaa | Xaa | Xaa | Xaa | Xaa<br>295 | Xaa | Xaa | Xaa | Xaa | Xaa<br>300 | Xaa | Xaa | Xaa |
| Xaa<br>305 | Xaa | Xaa | Xaa | Xaa | Xaa<br>310 | Xaa | Xaa | Xaa | Xaa | Xaa<br>315 | Xaa | Xaa | Xaa | Xaa<br>320 |
| Xaa | Xaa | Xaa | Xaa | Xaa<br>325 | Xaa | Xaa | Cys | Xaa | Xaa<br>330 | Xaa | Xaa | Xaa | Xaa | Xaa<br>335 | Xaa |
| Xaa | Xaa | Xaa | Xaa<br>340 | Xaa | Xaa | Xaa | Xaa | Xaa<br>345 | Xaa | Xaa | Xaa | Xaa | Xaa<br>350 | Xaa |
| Xaa | Xaa | Xaa<br>355 | Xaa | Xaa | Xaa | Cys | Xaa<br>360 | Xaa | Cys |

( 2 ) INFORMATION FOR SEQ ID NO:19:

( i ) SEQUENCE CHARACTERISTICS:
        ( A ) LENGTH: 411 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:19:

| Cys | Xaa | Xaa | Xaa | Xaa | Xaa | Xaa | Xaa | Xaa | Xaa | Xaa | Xaa | Xaa | Xaa | Xaa |
| 1 | | | | 5 | | | | | 10 | | | | | 15 |
| Cys | Xaa | Xaa | Xaa | Xaa | Xaa | Xaa | Xaa | Xaa | Xaa | Xaa | Xaa | Xaa | Xaa | Xaa |
| | | | 20 | | | | | 25 | | | | | 30 | |
| Ala | Cys | Ala | Pro | Tyr | Arg | Arg | Leu | His | Val | Cys | Asp | Gln | Asn | Leu | Xaa |
| | | 35 | | | | | 40 | | | | | 45 | | | |
| Xaa | Xaa | Xaa | Xaa | Xaa | Xaa | Xaa | Xaa | Xaa | Xaa | Xaa | Xaa | Xaa | Xaa | Xaa |
| | 50 | | | | | 55 | | | | | 60 | | | |
| Xaa | Xaa | Xaa | Xaa | Xaa | Xaa | Xaa | Xaa | Xaa | Xaa | Xaa | Xaa | Xaa | Xaa | Xaa |
| 65 | | | | | 70 | | | | | 75 | | | | 80 |
| Xaa | Xaa | Xaa | Xaa | Xaa | Xaa | Xaa | Xaa | Xaa | Xaa | Xaa | Xaa | Gln | Ile | Cys | Thr |
| | | | | 85 | | | | | 90 | | | | | 95 | |
| Met | Leu | Ala | Arg | Ser | Phe | Ala | Asp | Ile | Gly | Asp | Ile | Val | Arg | Gly | Arg |
| | | | 100 | | | | | 105 | | | | | 110 | | |
| Asp | Leu | Tyr | Leu | Gly | Asn | Pro | Gln | Glu | Xaa | Xaa | Xaa | Xaa | Xaa | Xaa |
| | | 115 | | | | | 120 | | | | | 125 | | |
| Xaa | Xaa | Xaa | Xaa | Xaa | Xaa | Xaa | Xaa | Xaa | Xaa | Xaa | Xaa | Xaa | Xaa | Xaa |
| | 130 | | | | | 135 | | | | | 140 | | | |
| Xaa | Xaa | Xaa | Xaa | Xaa | Xaa | Xaa | Asn | Asp | Pro | Glu | Phe | Phe | Lys | Leu | Arg |
| 145 | | | | | 150 | | | | | 155 | | | | | 160 |
| Glu | Asp | Trp | Trp | Thr | Ala | Asn | Arg | Glu | Thr | Val | Trp | Lys | Ala | Ile | Thr |
| | | | | 165 | | | | | 170 | | | | | 175 | |
| Cys | Asn | Ala | Xaa | Xaa | Xaa | Xaa | Xaa | Xaa | Xaa | Xaa | Xaa | Cys | Xaa | Xaa | Xaa |
| | | | 180 | | | | | 185 | | | | | 190 | | |
| Xaa | Xaa | Xaa | Xaa | Xaa | Xaa | Xaa | Xaa | Xaa | Xaa | Xaa | Xaa | Xaa | Xaa | Xaa |
| | | 195 | | | | | 200 | | | | | 205 | | |
| Xaa | Xaa | Xaa | Xaa | Val | Pro | Gln | Tyr | Leu | Arg | Trp | Phe | Glu | Glu | Trp | Ala |
| | 210 | | | | | 215 | | | | | 220 | | | | |
| Glu | Asp | Phe | Cys | Arg | Lys | Lys | Asn | Lys | Lys | Ile | Lys | Asp | Val | Lys | Arg |
| 225 | | | | | 230 | | | | | 235 | | | | | 240 |
| Asn | Cys | Xaa | Xaa | Xaa | Xaa | Xaa | Xaa | Xaa | Xaa | Xaa | Xaa | Xaa | Cys | Xaa |
| | | | | 245 | | | | | 250 | | | | | 255 |
| Xaa | Xaa | Xaa | Xaa | Xaa | Xaa | Xaa | Xaa | Xaa | Xaa | Xaa | Xaa | Xaa | Xaa | Xaa |
| | | | 260 | | | | | 265 | | | | | 270 | |
| Xaa | Xaa | Xaa | Xaa | Xaa | Cys | Ile | Ser | Cys | Leu | Tyr | Ala | Cys | Asn | Pro | Tyr |
| | | 275 | | | | | 280 | | | | | 285 | | | |
| Val | Asp | Trp | Ile | Asn | Asn | Gln | Lys | Glu | Xaa | Xaa | Xaa | Xaa | Xaa | Xaa |
| | 290 | | | | | 295 | | | | | 300 | | | |
| Xaa | Xaa | Xaa | Xaa | Xaa | Xaa | Xaa | Xaa | Xaa | Xaa | Xaa | Xaa | Xaa | Xaa | Xaa |
| 305 | | | | | 310 | | | | | 315 | | | | | 320 |
| Xaa | Xaa | Xaa | Xaa | Xaa | Xaa | Xaa | Xaa | Xaa | Xaa | Xaa | Xaa | Xaa | Xaa | Xaa |
| | | | | 325 | | | | | 330 | | | | | 335 |
| Xaa | Xaa | Xaa | Xaa | Xaa | Xaa | Xaa | Xaa | Xaa | Xaa | Xaa | Xaa | Xaa | Xaa | Xaa |
| | | | 340 | | | | | 345 | | | | | 350 | |
| Xaa | Xaa | Xaa | Xaa | Xaa | Xaa | Xaa | Xaa | Xaa | Xaa | Xaa | Xaa | Xaa | Cys | Xaa |
| | | 355 | | | | | 360 | | | | | 365 | | |
| Xaa | Xaa | Xaa | Xaa | Xaa | Xaa | Xaa | Xaa | Xaa | Xaa | Xaa | Xaa | Xaa | Xaa | Xaa |
| | 370 | | | | | 375 | | | | | 380 | | | |
| Xaa | Xaa | Xaa | Xaa | Xaa | Xaa | Xaa | Xaa | Xaa | Xaa | Xaa | Xaa | Xaa | Xaa | Xaa |

```
              385                    390                      395                      400
Xaa   Xaa   Xaa   Xaa   Xaa   Xaa   Xaa   Cys   Xaa   Xaa   Cys
                        405                    410
```

( 2 ) INFORMATION FOR SEQ ID NO:20:

( i ) SEQUENCE CHARACTERISTICS:
        ( A ) LENGTH: 411 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:20:

```
Cys   Xaa   Xaa   Xaa   Xaa   Xaa   Xaa   Xaa   Xaa   Xaa   Xaa   Xaa   Xaa   Xaa   Xaa
  1                     5                              10                           15

Xaa   Xaa   Cys   Xaa   Xaa   Xaa   Xaa   Xaa   Xaa   Xaa   Xaa   Xaa   Xaa   Xaa   Xaa
              20                            25                           30

Xaa   Xaa   Xaa   Xaa   Xaa   Xaa   Xaa   Xaa   Xaa   Xaa   Xaa   Xaa   Xaa   Xaa   Xaa
              35                            40                           45

Xaa   Xaa   Val   Phe   Leu   Pro   Pro   Arg   Arg   Glu   His   Met   Cys   Thr   Ser   Asn
       50                     55                           60

Leu   Xaa   Xaa   Xaa   Xaa   Xaa   Xaa   Xaa   Xaa   Xaa   Xaa   Xaa   Xaa   Xaa   Xaa
 65                           70                           75                           80

Xaa   Xaa   Xaa   Xaa   Xaa   Xaa   Xaa   Xaa   Xaa   Xaa   Xaa   Xaa   Xaa   Xaa   Xaa
              85                            90                           95

Xaa   Xaa   Xaa   Xaa   Xaa   Xaa   Xaa   Xaa   Xaa   Xaa   Xaa   Xaa   Xaa   Xaa   Xaa
             100                           105                          110

Xaa   Xaa   Xaa   Xaa   Xaa   Xaa   Xaa   Xaa   Ala   Met   Cys   Arg   Ala   Val   Arg   Tyr
             115                           120                          125

Ser   Phe   Ala   Asp   Leu   Gly   Asp   Ile   Ile   Arg   Gly   Arg   Asp   Met   Trp   Asp
       130                           135                          140

Glu   Asp   Lys   Ser   Ser   Xaa   Xaa   Xaa   Xaa   Xaa   Xaa   Xaa   Xaa   Xaa   Xaa
145                           150                          155                          160

Xaa   Xaa   Xaa   Xaa   Xaa   Xaa   Xaa   Xaa   Xaa   Xaa   Xaa   Xaa   Xaa   Xaa   Xaa
                  165                            170                          175

Xaa   Xaa   Xaa   Xaa   Xaa   Lys   Lys   Pro   Ala   Tyr   Lys   Lys   Leu   Arg   Ala   Asp
                  180                            185                          190

Trp   Trp   Glu   Ala   Asn   Arg   His   Gln   Val   Trp   Arg   Ala   Met   Lys   Cys   Ala
             195                           200                          205

Thr   Xaa   Xaa   Xaa   Xaa   Cys   Xaa   Xaa   Xaa   Xaa   Xaa   Xaa   Xaa   Xaa   Ile   Pro
       210                           215                          220

Gln   Arg   Leu   Arg   Trp   Met   Thr   Glu   Trp   Ala   Glu   Trp   Tyr   Cys   Lys   Ala
225                           230                          235                          240

Gln   Ser   Gln   Glu   Tyr   Asp   Lys   Leu   Lys   Lys   Ile   Cys   Xaa   Xaa   Xaa   Xaa
                  245                            250                          255

Xaa   Xaa   Xaa   Xaa   Xaa   Xaa   Xaa   Cys   Xaa   Xaa   Xaa   Xaa   Xaa   Xaa   Cys   Gly
             260                           265                          270

Lys   Cys   Lys   Ala   Ala   Cys   Asp   Tyr   Lys   Glu   Glu   Ile   Glu   Lys   Trp
       275                           280                          285
```

| Asn | Glu | Gln | Trp | Arg | Lys | Xaa | Xaa | Xaa | Xaa | Xaa | Xaa | Xaa | Xaa | Xaa |
|---|---|---|---|---|---|---|---|---|---|---|---|---|---|---|
| 290 | | | | | 295 | | | | 300 | | | | | |
| Xaa | Xaa | Xaa | Xaa | Xaa | Xaa | Xaa | Xaa | Xaa | Xaa | Xaa | Xaa | Xaa | Xaa | Xaa |
| 305 | | | | 310 | | | | | 315 | | | | | 320 |
| Xaa | Xaa | Xaa | Xaa | Xaa | Xaa | Xaa | Xaa | Xaa | Xaa | Xaa | Xaa | Xaa | Xaa | Xaa |
| | | | | 325 | | | | | 330 | | | | 335 | |
| Xaa | Xaa | Xaa | Xaa | Xaa | Xaa | Xaa | Xaa | Xaa | Xaa | Xaa | Xaa | Xaa | Xaa | Xaa |
| | | | 340 | | | | | 345 | | | | | 350 | |
| Xaa | Xaa | Xaa | Xaa | Xaa | Xaa | Xaa | Xaa | Xaa | Xaa | Xaa | Xaa | Xaa | Xaa | Cys |
| | | 355 | | | | | | 360 | | | | | 365 | |
| Xaa | Xaa | Xaa | Xaa | Xaa | Xaa | Xaa | Cys | Xaa | Xaa | Xaa | Xaa | Xaa | Xaa | Xaa |
| | 370 | | | | | | 375 | | | | | 380 | | |
| Xaa | Xaa | Xaa | Xaa | Xaa | Xaa | Xaa | Xaa | Xaa | Xaa | Xaa | Xaa | Xaa | Xaa | Xaa |
| 385 | | | | | 390 | | | | | 395 | | | | 400 |
| Xaa | Xaa | Xaa | Xaa | Xaa | Xaa | Xaa | Cys | Xaa | Xaa | Cys | | | | |
| | | | | 405 | | | | | 410 | | | | | |

( 2 ) INFORMATION FOR SEQ ID NO:21:

( i ) SEQUENCE CHARACTERISTICS:
        ( A ) LENGTH: 311 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:21:

| Cys | Xaa | Xaa | Xaa | Xaa | Xaa | Xaa | Xaa | Xaa | Xaa | Xaa | Cys | Xaa | Xaa | Xaa | Xaa |
|---|---|---|---|---|---|---|---|---|---|---|---|---|---|---|---|
| 1 | | | | | 5 | | | | | 10 | | | | | 15 |
| Xaa | Xaa | Xaa | Xaa | Xaa | Xaa | Xaa | Ala | Cys | Met | Pro | Pro | Arg | Arg | Gln | Lys | Leu |
| | | | 20 | | | | | | 25 | | | | | 30 | | |
| Cys | Leu | Tyr | Tyr | Ile | Xaa | Xaa | Xaa | Xaa | Xaa | Xaa | Xaa | Xaa | Xaa | Xaa |
| | | | 35 | | | | | 40 | | | | | 45 | |
| Xaa | Xaa | Xaa | Xaa | Xaa | Xaa | Xaa | Xaa | Xaa | Xaa | Xaa | Xaa | Xaa | Xaa | Xaa |
| | 50 | | | | | 55 | | | | | 60 | | | |
| Xaa | Xaa | Xaa | Xaa | Xaa | Xaa | Xaa | Xaa | Xaa | Xaa | Xaa | Xaa | Xaa | Xaa | Xaa |
| 65 | | | | | 70 | | | | | 75 | | | | 80 |
| Xaa | Xaa | Xaa | Xaa | Xaa | Xaa | Xaa | Xaa | Xaa | Gln | Phe | Leu | Arg | Ser | Met | Met |
| | | | | 85 | | | | | 90 | | | | | 95 | |
| Tyr | Thr | Phe | Gly | Asp | Tyr | Arg | Asp | Ile | Cys | Leu | Asn | Thr | Asp | Ile | Ser |
| | | | 100 | | | | | 105 | | | | | 110 | | |
| Lys | Lys | Gln | Asn | Asp | Val | Xaa | Xaa | Xaa | Xaa | Xaa | Xaa | Xaa | Xaa |
| | | | 115 | | | | | 120 | | | | | 125 |
| Xaa | Xaa | Xaa | Xaa | Xaa | Ser | Lys | Ser | Pro | Ser | Gly | Leu | Ser | Arg | Gln | Glu |
| | | 130 | | | | 135 | | | | | 140 | | | | |
| Trp | Trp | Lys | Thr | Asn | Gly | Pro | Glu | Ile | Trp | Lys | Gly | Met | Leu | Cys | Ala |
| 145 | | | | | 150 | | | | | 155 | | | | | 160 |
| Leu | Xaa | Xaa | Xaa | Xaa | Xaa | Xaa | Xaa | Xaa | Xaa | Xaa | Xaa | Xaa | Xaa | Xaa |
| | | | | | 165 | | | | | 170 | | | | 175 |
| Xaa | Xaa | Xaa | Xaa | Xaa | Xaa | Xaa | Xaa | Xaa | Xaa | Xaa | Xaa | Xaa | Xaa | Xaa |
| | | | 180 | | | | | 185 | | | | | 190 | |

| | | | | | | | | | | | | | | |
|---|---|---|---|---|---|---|---|---|---|---|---|---|---|---|
| Xaa | Xaa | Xaa<br>195 | Xaa | Xaa | Xaa | Lys | Pro<br>200 | Gln | Phe | Leu | Arg | Trp<br>205 | Met | Ile | Glu |
| Trp | Gly<br>210 | Glu | Glu | Phe | Cys | Ala<br>215 | Glu | Arg | Gln | Lys | Lys<br>220 | Glu | Asn | Ile | Ile |
| Lys<br>225 | Asp | Ala | Cys | Xaa | Xaa<br>230 | Xaa | Xaa | Xaa | Xaa | Xaa<br>235 | Xaa | Cys | Xaa | Xaa | Xaa<br>240 |
| Lys | His | Arg | Cys | Asn<br>245 | Gln | Ala | Cys | Arg | Ala<br>250 | Tyr | Gln | Glu | Tyr | Val<br>255 | Glu |
| Asn | Lys | Lys | Lys<br>260 | Xaa | Xaa | Xaa | Xaa | Xaa<br>265 | Xaa | Xaa | Xaa | Xaa | Xaa<br>270 | Xaa | Xaa |
| Xaa | Xaa | Xaa<br>275 | Xaa | Xaa | Xaa | Xaa | Xaa | Xaa<br>280 | Xaa | Xaa | Xaa | Xaa | Xaa<br>285 | Xaa | Xaa |
| Xaa | Xaa | Xaa<br>290 | Xaa | Xaa | Xaa | Xaa | Xaa | Xaa<br>295 | Xaa | Xaa | Xaa | Xaa | Xaa<br>300 | Xaa | Xaa | Cys |
| Xaa<br>305 | Xaa | Xaa | Xaa | Cys | Xaa<br>310 | Cys |

(2) INFORMATION FOR SEQ ID NO:22:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO:22:

| | | | | | | |
|---|---|---|---|---|---|---|
| Pro<br>1 | Arg | Arg | Gln | Xaa<br>5 | Leu | Cys |

(2) INFORMATION FOR SEQ ID NO:23:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:23:

CCRAGRAGRC AARAAYTATG    20

(2) INFORMATION FOR SEQ ID NO:24:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: NO (v) FRAGMENT TYPE:

(v i) ORIGINAL SOURCE:

(x i) SEQUENCE DESCRIPTION: SEQ ID NO:24:

CCSMGSMGSC AGCAGYTSTG 20

(2) INFORMATION FOR SEQ ID NO:25:

(i) SEQUENCE CHARACTERISTICS:
        (A) LENGTH: 7 amino acids
        (B) TYPE: amino acid
        (C) STRANDEDNESS: single
        (D) TOPOLOGY: linear (i i) MOLECULE TYPE: peptide (i i i) HYPOTHETICAL: NO (i v) ANTI-SENSE: NO (v) FRAGMENT TYPE: N-terminal (v i) ORIGINAL SOURCE:

(x i) SEQUENCE DESCRIPTION: SEQ ID NO:25:

Phe Ala Asp Xaa Xaa Asp Ile
1                   5

(2) INFORMATION FOR SEQ ID NO:26:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: NO (v) FRAGMENT TYPE:

(v i) ORIGINAL SOURCE:

(x i) SEQUENCE DESCRIPTION: SEQ ID NO:26:

TTTGCWGATW WWSGWGATAT 20

(2) INFORMATION FOR SEQ ID NO:27:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: NO (v) FRAGMENT TYPE:

(v i) ORIGINAL SOURCE:

( x i ) SEQUENCE DESCRIPTION: SEQ ID NO:27:

TTCGCSGATW WCSGSGACAT 20

( 2 ) INFORMATION FOR SEQ ID NO:28:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:28:

Pro Gln Phe Xaa Arg Trp
1                5

( 2 ) INFORMATION FOR SEQ ID NO:29:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:29:

CCAWCKKARR AATTGWGG 18

( 2 ) INFORMATION FOR SEQ ID NO:30:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:30:

CCASCKGWAG AWCTGSGG 18

( 2 ) INFORMATION FOR SEQ ID NO:31:

( i ) SEQUENCE CHARACTERISTICS:
        ( A ) LENGTH: 7 amino acids (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO:31:

Glu Trp Gly Xaa Xaa Xaa Cys
 1               5

(2) INFORMATION FOR SEQ ID NO:32:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:32:

CAAWAWTCWT CWCCCCATTC                                                                             20

(2) INFORMATION FOR SEQ ID NO:33:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:33:

CAGWASTCST CSCCCCACTC                                                                             20

(2) INFORMATION FOR SEQ ID NO:34:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO ( v ) FRAGMENT TYPE:

( v i ) ORIGINAL SOURCE:

( x i ) SEQUENCE DESCRIPTION: SEQ ID NO:34:

ATCGATCAGC TGGGAAGAAA TACTTCATCT 30

( 2 ) INFORMATION FOR SEQ ID NO:35:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:35:

ATCGATGGGC CCCGAAGTTT GTTCATTATT 30

( 2 ) INFORMATION FOR SEQ ID NO:36:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:36:

TCTCGTCAGC TGACGATCTC TAGTGCTATT 30

( 2 ) INFORMATION FOR SEQ ID NO:37:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:37:

ACGAGTGGGC CCTGTCACAA CTTCCTGAGT 30

BINDING DOMAINS FROM *PLASMODIUM VIVAX* AND *PLASMODIUM FALCIPARUM* ERYTHROCYTE BINDING PROTEINS

This application is a continuation of U.S. patent application Ser. No. 08/119,677, filed Sep. 10, 1993 now abandoned.

BACKGROUND OF THE INVENTION

Malaria infects 200–400 million people each year causing 1–2 million deaths, thus remaining one of the most important infectious diseases in the world. Approximately 25 percent of all deaths of children in rural Africa between the ages of one and four years are caused by malaria. Due to the importance of the disease as a worldwide health problem, considerable effort is being expended to identify and develop malaria vaccines.

Malaria in humans is caused by four species of the parasite Plasmodium: *P. falciparum, P. vivax, P. knowlesi* and *P. malariae*. The major cause of malaria in humans if *P. falciparum* which infects 200 million to 400 million people every year, killing 1 to 4 million.

*P. vivax* (one of the four species infective to humans) cannot be cultured in vitro, as has been possible with *P. knowlesi* (a malarial strain found in old world monkeys which also invade human erythrocytes) and *P. falciparum*. Although *P. vivax* bears substantial phylogenetic similarity to *P. knowlesi*, the two species are different in many important respects. For example, *P. vivax* is not infective of many simian species and infection is poorly established in others, whereas *P. knowlesi* is poorly infective of humans while readily infecting many simian species.

The basis of various potential vaccines to combat malaria is appreciated through an understanding of the life cycle of the parasite. Infection in humans begins when young malarial parasites or "sporozoites" are injected into the bloodstream of a human by the mosquito. Following injection, the parasite localizes to liver cells. After approximately one week the parasites or "merozoites" are released into the bloodstream. The entry of the parasites into the bloodstream begins the "erythrocytic" phase. Each parasite enters the red blood cell in order to grow and develop. When the merozoite matures in the red blood cell, it is known as a trophozoite. The trophozoite undergoes several rounds of nuclear division (schizogony) until it ruptures the erythrocyte, releasing from 6 to 24 merozoites. After several asexual schizogonic cycles, some parasites, instead of becoming schizonts through asexual reproduction, develop into morphologically distinct forms known as "gametocytes" which are long-lived and undergo sexual development.

Sexual development of the malaria parasites involve the female or "macrogametocyte" and the male parasite or "microgametocyte." These gametocytes do not undergo any further development in humans. Upon ingestion of the gametocytes into the mosquito, the complicated sexual cycle begins in the midgut of the mosquito. The red blood cells disintegrate in the midgut of the mosquito after 10 to 20 minutes. The microgametocyte continues to develop through exflagellation and releases 8 highly flagellated microgametes. Fertilization occurs upon fusion of the microgamete and the macrogamete. The fertilized parasite is known as a zygote which develops into an "ookinete." The ookinete embeds in the midgut of the mosquito, transforming into an oocyst within which many small sporozoites form. Before embedding in the midgut, the ookinete must first penetrate the peritrophic membrane which apparently acts as a barrier for invasion of ingested parasites. When the oocyst ruptures the sporozoites migrate to the salivary gland of the mosquito via the hemolymph. Once in the saliva of the mosquito, the parasite can be injected into a host.

The erythrocytic stage of the Plasmodium life cycle is of special relevance to vaccine development because the clinical and pathologic features of malaria in the host are attributable to this stage. In *P. vivax*, and *P. knowlesi*, Duffy blood group determinants present on Duffy positive erythrocytes are essential for invasion of human erythrocytes (Miller et al., Science 189: 561–563, (1975); Miller et al., N. Engl. J. Med. 295: 302–304, (1976)). In *P. falciparum*, invasion of merozoites into erythrocytes appears to be dependent on binding to sialic acids on glycophorins on the erythrocyte (Miller, et al., J. Exp. Med. 146: 277–281, (1971); Pasvol, et al., Lancet. ii: 947–950 (1982); Pasvol, et al., Nature, 279: 64–66 (1982); Perkins, J. Exp. Med. 160: 788–798 (1984)). Studies with the monkey parasite *P. knowlesi* allow a clearer understanding of the multiple events that occur during invasion. It is likely that even though *P. vivax* and *P. falciparum* bind to the Duffy antigen and sialic acids respectively, they share common strategies of invasion with each other and with *P. knowlesi*.

In *P. knowlesi*, during invasion a merozoite first attaches to an erythrocyte on any surface of the merozoite, then reorients so that its apical end is in contact with the erythrocyte (Dvorak et al., Science 187: 748–750, (1975)). Both attachment and reorientation of merozoites occur equally well on Duffy positive and Duffy negative cells. A junction then forms between the apical end of the merozoite and the Duffy positive erythrocyte followed by vacuole formation and entry of the merozoite into the vacuole. Aikawa et al., J. Cell Biol. 77: 72–82 (1978). Junction formation and merozoite entry into the erythrocyte do not occur on Duffy negative cells (Miller et al., J. Exp. Med. 149: 172–184 (1979)), suggesting that a receptor specific for the Duffy determinant is involved in apical junction formation but not initial attachment.

The apical end of the merozoite is defined by the presence of three organelles: rhopteries, dense granules and micronemes. The rhopteries and dense granules release their contents at vacuole formation (Ladda et al., 1969; Aikawa et al., J. Cell Biol., 77: 72–82 (1978); Torn et al., Infection and Immunity 57: 3230–3233 (1989); Bannister and Dluzewski, Blood Cells 16: 257–292 (1990)). To date the function of the microneme is unknown. Nevertheless, the location of the micronemes suggest that they are involved in the invasion process. Duffy Antigen Binding Protein (DABP) and Sialic Acid Binding Protein (SABP) have been localized to the micronemes of *P. knowlesi* and *P. falciparum* respectively (Adams et al., Cell 63: 141–153 (1990); Sim et al., Mol. Biochem. Parasitol. 51: 157–160 (1992)).

DABP and SABP are soluble proteins that appear in the culture supernatant after infected erythrocytes release merozoites. Immunochemical data indicate that DABP and SABP which are the respective ligands for the *P. vivax* and *P. falciparum* Duffy and sialic acid receptors on erythrocytes, possess specificities of binding which are identical either in soluble or membrane bound form.

DABP is a 135 kDa protein which binds specifically to Duffy blood group determinants (Wertheimer et al., Exp. Parasitol. 69: 340–350 (1989); Barnwell, et al., J. Exp. Med. 169: 1795–1802 (1989)). Thus, binding of DABP is specific to human Duffy positive erythrocytes. There are four major Duffy phenotypes for human erythrocytes: Fy(a), Fy(b), Fy(ab) and Fy(negative), as defined by the anti-Fy$^a$ and anti-Fy$^b$ sera (Hadley et al., In Red Cell Antigens and Antibodies, G. Garratty, ed. (Arlington, Va.:American Association of Blood Banks) pp. 17–33 (1986)). DABP binds equally to both Fy(a) and Fy(b) erythrocytes which are equally susceptible to invasion by *P. vivax*; but not to Fy(negative) erythrocytes.

In the case of SABP, a 175 kDa protein, binding is specific to the glycophorin sialic acid residues on erythrocytes (Camus and Hadley, Science 230:553–556 (1985); Orlandi, et al., J. Cell Biol. 116:901–909 (1992)). Thus, neuraminidase treatment (which cleaves off sialic acid residues) render erythrocytes immune to *P. falciparum* invasion.

The specificities of binding and correlation to invasion by the parasite thus indicate that DABP and SABP are the proteins of *P. vivax* and *P. falciparum* which interact with sialic acids and the Duffy antigen on the erythrocyte. The genes encoding both proteins have been cloned and the DNA and predicted protein sequences have been determined (B. Kim Lee Sim, et al., J. Cell Biol. 111: 1877–1884 (1990); Fang, X., et al., Mol. Biochem Parasitol. 44: 125–132 (1991)).

Despite considerable research efforts worldwide, because of the complexity of the Plasmodium parasite and its interaction with its host, it has not been possible to discover a satisfactory solution for prevention or abatement of the blood stage of malaria. Because malaria is such a large worldwide health problem, there is a need for methods that abate the impact of this disease. The present invention provides effective preventive and therapeutic measures against Plasmodium invasion.

SUMMARY OF THE INVENTION

The present invention provides compositions comprising an isolated DABP binding domain polypeptides and/or isolated SABP binding domain polypeptides. The DABP binding domain polypeptides preferably comprise between about 200 and about 300 amino acid residues while the SABP binding domain polypeptides preferably comprises between about 200 and about 600 amino acid residues. A preferred DABP binding domain polypeptide has residues 1 to about 325 of the amino acid sequence found in SEQ ID No. 2. A preferred SABP binding domain polypeptide has residues 1 to about 616 of the amino acid sequence of SEQ ID No. 4.

The present invention also includes pharmaceutical compositions comprising a pharmaceutically acceptable carrier and an isolated DABP binding domain polypeptide in an amount sufficient to induce a protective immune response to *Plasmodium vivax* merozoites in an organism. In addition, isolated SABP binding domain polypeptide in an amount sufficient to induce a protective immune response to *Plasmodium falciparum* may be added to the pharmaceutical composition.

Also provided are pharmaceutical compositions comprising a pharmaceutically acceptable carrier and an isolated SABP binding domain polypeptide in an amount sufficient to induce a protective immune response to *Plasmodium falciparum* merozoites in an organism. In addition, isolated DABP binding domain polypeptide in an amount sufficient to induce a protective immune response to *Plasmodium vivax* may be added to the pharmaceutical composition.

Isolated polynucleotides which encode a DABP binding domain polypeptides or SABP binding domain polypeptides are also disclosed. In addition, the present invention includes a recombinant cell comprising the polynucleotide encoding the DABP binding domain polypeptide.

The current invention further includes methods of inducing a protective immune response to Plasmodium merozoites in a patient. The methods comprise administering to the patient an immunologically effective amount of a pharmaceutical composition comprising a pharmaceutically acceptable carrier and an isolated DABP binding domain polypeptide, an SABP binding domain polypeptide or a combination thereof.

The present disclosure also provides DNA sequences from additional *P. falciparum* genes in the erythrocyte binding ligand (EBL) family that have regions conserved with the *P. falciparum* 175 kD and *P. vivax* 135 kD binding proteins.

DEFINITIONS

As used herein a "DABP binding domain polypeptide" or a "SABP binding domain polypeptide" are polypeptides substantially identical (as defined below) to a sequence from the cysteine-rich, amino-terminal region of the Duffy antigen binding protein (DABP) or sialic acid binding protein (SABP), respectively. Such polypeptides are capable of binding either the Duffy antigen or sialic acid residues on glycophorin. In particular, DABP binding domain polypeptides consist of amino acid residues substantially similar to a sequence of SABP within a binding domain from the N-terminal amino acid (residue 1) to about residue 325. SABP binding domain polypeptides consist of residues substantially similar to a sequence of DABP within a binding domain from the N-terminal amino acid (residue 1) to about residue 616.

The binding domain polypeptides encoded by the genes of the EBL family consist of those residues substantially identical to the sequence of the binding domains of DABP and SABP as defined above. The EBL family comprises sequences with substantial similarity to the conserved regions of the DABP and SABP. These include those sequences reported here as EBL-e1 (SEQ ID NO: 5 and SEQ ID NO: 6), E31a (SEQ ID NO: 7 and SEQ ID NO: 8), EBL-e2 (SEQ ID NOs 9 and 10) and Proj3 (SEQ ID NO: 11 and SEQ ID NO: 12).

The polypeptides of the invention can consist of the full length binding domain or a fragment thereof. Typically DABP binding domain polypeptides will consist of from about 50 to about 325 residues, preferably between about 75 and 300, more preferably between about 100 and about 250 residues. SABP binding domain polypeptides will consist of from about 50 to about 616 residues, preferably between about 75 and 300, more preferably between about 100 and about 250 residues.

Particularly preferred polypeptides of the invention are those within the binding domain that are conserved between SABP and the EBL family. Residues within these conserved domains are shown in FIG. 1, below.

Two polynucleotides or polypeptides are said to be "identical" if the sequence of nucleotides or amino acid residues in the two sequences is the same when aligned for maximum correspondence. Optimal alignment of sequences for comparison may be conducted by the local homology algorithm of Smith and Waterman *Adv. Appl. Math.* 2: 482 (1981), by the homology alignment algorithm of Needleman and Wunsch *J. Mol. Biol.* 48:443 (1970), by the search for similarity method of Pearson and Lipman *Proc. Natl. Acad. Sci.* (*U.S.A.*) 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection. These references are incorporated herein by reference.

The term "substantial identity" means that a polypeptide comprises a sequence that has at least 80% sequence identity, preferably 90%, more preferably 95% or more, compared to a reference sequence over a comparison window of about 20 residues to about 600 residues—typically about 50 to about 500 residues usually about 250 to 300 residues. The values of percent identity are determined using the programs above. Particularly preferred peptides of the present invention comprise a sequence in which at least 70% of the cysteine residues conserved in DABP and SABP are present. Additionally, the peptide will comprise a sequence in which at least 50% of the Tryptophan residues conserved in DABP and SABP are present. The term substantial similarity is also specifically defined here with respect to those amino acid residues found to be conserved between DABP, SABP and the sequences of the EBL family. These conserved amino acids consist prominently of tryptophan and cysteine residues conserved among all sequences reported here. In addition the conserved amino acid residues include phenylalanine residues which may be substituted with tyrosine. These amino acid residues may be determined to be conserved after the sequences have been aligned using methods outlined above by someone skilled in the art.

Another indication that polypeptide sequences are substantially identical is if one protein is immunologically reactive with antibodies raised against the other protein. Thus, the polypeptides of the invention include polypeptides immunologically reactive with antibodies raised against the SABP binding domain, the DABP binding domain or raised against the conserved regions of the EBL family.

Another indication that nucleotide sequences are substantially identical is if two molecules hybridize to each other under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is at least about 0.02 molar at pH 7 and the temperature is at least about 60° C.

The phrases "isolated" or "biologically pure" refer to material which is substantially or essentially free from components which normally accompany it as found in its native state. Thus, the binding domain polypeptides of this invention do not contain materials normally associated with their in situ environment, e.g., other proteins from a merozoite membrane. However, even where a protein has been isolated to a homogenous or dominant band by PAGE, there can be trace contaminants in the range of 5–10% of native protein which co-purify with the desired protein. Isolated polypeptides of this invention do not contain such endogenous co-purified protein.

Protein purity or homogeneity may be indicated by a number of means well known in the art, such as polyacrylamide gel electrophoresis of a protein sample, followed by visualization upon staining. For certain purposes high resolution will be needed and HPLC or a similar means for purification utilized.

The term "residue" refers to an amino acid (D or L) or amino acid mimetic incorporated in a oligopeptide by an amide bond or amide bond mimetic. An amide bond mimetic of the invention includes peptide backbone modifications well known to those skilled in the art.

BRIEF DESCRIPTION OF THE DRAWINGS

FIG. 1 represents an alignment of the predicted amino acid sequences of the DABP binding domain (SEQ ID NO: 13) (Vivax), the two homologous SABP domains (SABP F1 (SEQ ID NO: 14) and SABP F2(SEQ ID NO: 15)) and the sequenced members of the EBL gene family (ebl-e1 (SEQ ID NO: 16), E31a (SEQ ID NO: 17), EBL-e2 (SEQ ID NO: 18) and the three homologous Proj3 domains.

FIG. 3 shows primers (SEQ ID NO:23, SEQ ID NO:24, SEQ ID NO:26, SEQ ID NO:27, SEQ ID NO:29, SEQ ID NO:30, SEQ ID NO:32 and SEQ ID NO:33) useful for isolating sequences encoding the conserved motifs of the invention.

DESCRIPTION OF THE PREFERRED EMBODIMENT

Figure 2:
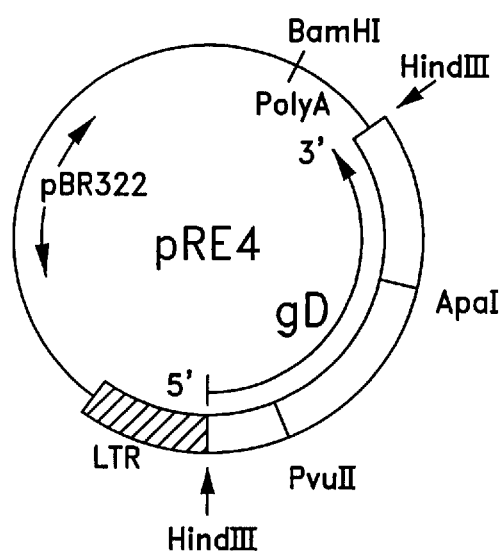
FIG. 2 represents a schematic of the pRE4 cloning vector.

The binding of merozoites and schizonts to erythrocytes is mediated by specific binding proteins on the surface of the merozoite or schizont and is necessary for erythrocyte invasion. In the case of *P. falciparum*, this binding involves specific interaction between sialic acid glycophorin residues on the erythrocyte and the sialic acid binding protein (SABP) on the surface of the merozoite or schizont. The ability of purified SABP to bind erythrocytes with chemically or enzymatically altered sialic acid residues paralleled the ability of *P. falciparum* to invade these erythrocytes. Furthermore, sialic acid deficient erythrocytes neither bind SABP nor support invasion by *P. falciparum*. The DNA encoding SABP from *P. falciparum* has also been cloned and sequenced.

In *P. vivax*, specific binding to the erythrocytes involves interaction between the Duffy blood group antigen on the erythrocyte and the Duffy antigen binding protein (DABP) on the merozoite. Duffy binding proteins were defined biologically as those soluble proteins that appear in the culture supernatant after the infected erythrocytes release merozoites which bind to human Duffy positive, but not to human Duffy negative erythrocytes. It has been shown that binding of the *P. vivax* DABP protein to Duffy positive erythrocytes is blocked by antisera to the Duffy blood group determinants. Purified Duffy blood group antigens also block the binding to erythrocytes. DABP has also been shown to bind Duffy blood group determinants on Western blots.

Duffy positive blood group determinants on human erythrocytes are essential for invasion of human erythrocytes by *Plasmodium vivax*. Both attachment and reorientation of *P. vivax* merozoites occur equally well on Duffy positive and negative erythrocytes. A junction then forms between the apical end of the merozoite and the Duffy-positive erythrocyte, followed by vacuole formation and entry of the merozoite into the vacuole. Junction formation and merozoite entry into the erythrocyte do not occur on Duffy negative cells, suggesting that the receptor specific for the Duffy determinant is involved in apical junction formation but not initial attachment. The DNA sequences encoding the DABP from *P. vivax* and *P. knowlesi* have been cloned and sequenced.

*P. vivax* red cell invasion has an absolute requirement for the Duffy blood group antigen. Isolates of *P. falciparum*, however, vary in their dependency on sialic acid for invasion. Certain *P. falciparum* clones have been developed which invade sialic acid deficient erythrocytes at normal rates. This suggests that certain strains of *P. falciparum* can interact with other ligands on the erythrocyte and so may possess multiple erythrocyte binding proteins with differing specificities.

A basis for the present invention is the discovery of the binding domains in both DABP and SABP. Comparison of the predicted protein sequences of DABP and SABP reveals an amino-terminal, cysteine-rich region in both proteins with a high degree of similarity between the two proteins. The amino-terminal, cysteine-rich region of DABP contains about 325 amino acids, whereas the amino-terminal, cysteine-rich region of SABP contains about 616 amino acids. This is due to an apparent duplication of the amino-terminal, cysteine-rich region in the SABP protein. The cysteine residues are conserved between the two regions of SABP and DABP, as are the amino acids surrounding the cysteine residues and a number of aromatic amino acid residues in this region. The amino-terminal cysteine rich region and another cysteine-rich region near the carboxyl-terminus show the most similarity between the DABP and SABP proteins. The region of the amino acid sequence between these two cysteine-rich regions show only limited similarity between DABP and SABP.

Other *P. falciparum* open reading frames and genes with regions that have substantial identity to binding domains of SABP and DABP have been identified. Multiple copies of these sequences exist in the parasite genome, indicating their important activity in host-parasite interactions. A family of these sequences (the EBL family) have been cloned from chromosome 7 subsegment libraries that were constructed during genetic studies of the chloroquine resistance locus (Wellems et. al., *PNAS* 88: 3382–3386 (1991)). Alignment of EBL sequences identified domains highly conserved with the *P. falciparum* 175 kD protein; these conserved domains have in turn been used to identify genes (ebl-e1, ebl-e2) one of which (ebl-e1) resides on chromosome 13. Genetic linkage studies have placed this gene within a region of chromosome 13 that affects invasion of malarial parasites in human red blood cells (Wellems et al., *Cell* 49:633–642 (1987)).

Southern hybridization experiments using probes from these open reading frames have indicated that additional copies of these conserved sequences are located elsewhere in the genome. The largest of the open reading frames on chromosome 7 is 8 kilobases and contains four tandem repeats homologous to the N-terminal, cysteine-rich unit of SABP and DABP.

FIG. 1 represents an alignment of the EBL family with the DABP binding domain (SEQ ID NO: 13) and two homologous regions of SABP. (F1 (SEQ ID NO:14) and F2 (SEQ ID NO:15)); The EBL family is divided into two subfamilies to achieve optimal alignment. Conserved cysteine residues are shown in bold face and conserved aromatic residues are underlined.

The polypeptides of the invention can be used to raise monoclonal antibodies specific for the binding domains of SABP, DABP or the conserved regions in the EBL gene family. The antibodies can be used for diagnosis of malarial infection or as therapeutic agents to inhibit binding of merozoites to erythrocytes. The production of monoclonal antibodies against a desired antigen is well known to those of skill in the art and is not reviewed in detail here.

The multitude of techniques available to those skilled in the art for production and manipulation of various immunoglobulin molecules can thus be readily applied to inhibit binding. As used herein, the terms "immunoglobulin" and "antibody" refer to a protein consisting of one or more polypeptides substantially encoded by immunoglobulin genes. Immunoglobulins may exist in a variety of forms besides antibodies, including for example, Fv, Fab, and F(ab)$_2$, as well as in single chains. For a general review of immunoglobulin structure and function see, *Fundamental Immunology*, 2d Ed., W. E. Paul ed., Ravens Press, New York, (1989).

Antibodies which bind polypeptides of the invention may be produced by a variety of means. The production of non-human monoclonal antibodies, e.g., murine, lagomorpha, equine, etc., is well known and may be accomplished by, for example, immunizing the animal with a preparation containing the polypeptide. Antibody-producing cells obtained from the immunized animals are immortalized and screened, or screened first for the production of antibody which inhibits binding between and meroxoites and erythrocytes and then immortalized. For a discussion of general procedures of monoclonal antibody production see Harlow and Lane, *Antibodies, A Laboratory Manual* Cold Spring Harbor Publications, New York (1988).

Thus, the present invention allows targeting of protective immune responses or monoclonal antibodies to sequences in the binding domains that are conserved between SABP, DABP and encoded regions of the EBL family. Identification of the binding regions of these proteins facilitates vaccine development because it allows for a focus of effort upon the functional elements of the large molecules. The particular sequences within the binding regions refine the target to critical regions that have been conserved during evolution, and are thus preferred for use as vaccines against the parasite.

The genes of the EBL family (which have not previously been sequenced) can be used as markers to detect the presence of the *P. falciparum* parasite in patients. This can be accomplished by means well known to practitioners in the art using tissue or blood from symptomatic patients in PCR reactions with oligonucleotides complementary to portions of the genes of the EBL family. Furthermore, sequencing the EBL family provides a means for skilled practitioners to generate defined probes to be used as genetic markers in a variety of applications.

Additionally, the present invention defines a conserved motif present in, but not restricted to other members of the subphylum Apicomplexa which participates in host parasite interaction. This motif can be identified in Plasmodium species and other parasitic protozoa by the polymerase chain reaction using the synthetic oligonucleotide primers shown in FIG. 3 (SEQ ID NO:23, SEQ ID NO:24, SEQ ID NO:26, SEQ ID NO:27, SEQ ID NO:29, SEQ ID NO:30, SEQ ID NO:32 and SEQ ID NO:33). PCR methods are described in detail below. These primers are designed from regions in the conserved motif showing the highest degree of conservation among DABP, SABP and the EBL family. FIG. 3 shows these regions and the consensus amino acid sequences derived from them (SEQ ID NO:22, SEQ ID NO:25, SEQ ID NO:28, and SEQ ID NO:31).

A. General Methods

Much of the nomenclature and general laboratory procedures required in this application can be found in Sambrook, et al., Molecular Cloning *A Laboratory Manual* (2nd Ed.), Vol. 1–3, Cold Spring Harbor Laboratory, Cold Spring Harbor, N.Y., 1989. The manual is hereinafter referred to as "Sambrook, et al."

B. Methods for isolating DNA encoding SABP, DABP and EBL binding regions

The nucleic acid compositions of this invention, whether RNA, cDNA, genomic DNA, or a hybrid of the various combinations, may be isolated from natural sources or may be synthesized in vitro. The nucleic acids claimed may be present in transformed or transfected whole cells, in a transformed or transfected cell lysate, or in a partially purified or substantially pure form.

Techniques for nucleic acid manipulation of genes encoding the binding domains of the invention, such as subcloning nucleic acid sequences encoding polypeptides into expression vectors, labelling probes, DNA hybridization, and the like are described generally in Sambrook et al., incorporated herein by reference.

Recombinant DNA techniques can be used to produce the binding domain polypeptides. In general, the DNA encoding the SABP and DABP binding domains are first cloned or isolated in a form suitable for ligation into an expression vector. After ligation, the vectors containing the DNA fragments or inserts are introduced into a suitable host cell for expression of the recombinant binding domains. The polypeptides are then isolated from the host cells.

There are various methods of isolating the DNA sequences encoding the SABP, DABP and EBL binding domains. Typically, the DNA is isolated from a genomic or cDNA library using labelled oligonucleotide probes specific for sequences in the DNA. Restriction endonuclease digestion of genomic DNA or cDNA containing the appropriate genes can be used to isolate the DNA encoding the binding domains of these proteins. Since the DNA sequences of the SABP and DABP genes are known, a panel of restriction endonucleases can be constructed to give cleavage of the DNA in the desired regions. After restriction endonuclease digestion, DNA encoding SABP binding domain or DABP binding domain is identified by its ability to hybridize with nucleic acid probes, for example on Southern blots, and these DNA regions are isolated by standard methods familiar to those of skill in the art. See Sambrook, et al.

The polymerase chain reaction can also be used to prepare DABP, SABP and EBL binding domain DNA. Polymerase chain reaction technology (PCR) is used to amplify nucleic acid sequences of the DABP and SABP binding domains directly from mRNA, from cDNA, and from genomic libraries or cDNA libraries. The primers shown in FIG. 3 are particularly preferred for this process.

Appropriate primers and probes for amplifying the SABP and DABP binding region DNA's are generated from analysis of the DNA sequences. In brief, oligonucleotide primers complementary to the two 3' borders of the DNA region to be amplified are synthesized. The polymerase chain reaction is then carried out using the two primers. See *PCR Protocols: A Guide to Methods and Applications.* (Innis, M, Gelfand, D., Sninsky, J. and White, T., eds.), Academic Press, San Diego (1990). Primers can be selected to amplify the entire DABP regions or to amplify smaller segments of the DABP and SABP binding domains, as desired.

Oligonucleotides for use as probes are chemically synthesized according to the solid phase phosphoramidite triester method first described by Beaucage, S. L. and Caruthers, M. H., 1981, Tetrahedron Letts., 22(20):1859–1862 using an automated synthesizer, as described in Needham-VanDevanter, D. R., et al. 1984, Nucleic Acids Res., 12:6159–6168. Purification of oligonucleotides is by either native acrylamide gel electrophoresis or by anion-exchange HPLC as described in Pearson, J. D. and Regnier, F. E., 1983, J. Chrom., 255:137–149.

The sequence of the synthetic oligonucleotides can be verified using the chemical degradation method of Maxam, A. M. and Gilbert, 1980, in W., Grossman, L. and Moldave, D., eds. Academic Press, New York, Methods in Enzymology, 65:499–560.

Other methods known to those of skill in the art may also be used to isolate DNA encoding all or part of the SABP or DABP binding domains. See Sambrook, et al.

C. Expression of DABP, SABP and EBL Binding Domain Polypeptides

Once the binding domain DNAs are isolated and cloned, one may express the desired polypeptides in a recombinantly engineered cell such as bacteria, yeast, insect (especially employing baculoviral vectors), and mammalian cells. It is expected that those of skill in the art are knowledgeable in the numerous expression systems available for expression of the DNA encoding the DABP and SABP binding domains. No attempt to describe in detail the various methods known for the expression of proteins in prokaryotes or eukaryotes will be made.

In brief summary, the expression of natural or synthetic nucleic acids encoding binding domains will typically be achieved by operably linking the DNA or cDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding the binding domains. To obtain high level expression of a cloned gene, it is desirable to construct expression plasmids which contain, at the minimum, a strong promoter to direct transcription, a ribosome binding site for translational initiation, and a transcription/translation terminator.

1. Expression in Prokaryotes

Examples of regulatory regions suitable for this purpose in *E. coli* are the promoter and operator region of the *E. coli* tryptophan biosynthetic pathway as described by Yanofsky, C., 1984, J. Bacteriol., 158:1018–1024 and the leftward promoter of phage lambda ($P_L$) as described by Herskowitz, I. and Hagen, D., 1980, Ann. Rev. Genet., 14:399–445. The inclusion of selection markers in DNA vectors transformed in *E. coli* is also useful. Examples of such markers include genes specifying resistance to ampicillin, tetracycline, or chloramphenicol. See Sambrook et al. for details concerning selection markers for use in *E. coli*.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA.

Expression systems for expressing the DABP and SABP binding domains are available using *E. coli*, Bacillus sp. (Palva, I et al., 1983, Gene 22:229–235; Mosbach, K. et al. Nature, 302:543–545) and Salmonella. *E. coli* systems are preferred.

The binding domain polypeptides produced by prokaryote cells may not necessarily fold properly. During purification from *E. coli*, the expressed polypeptides may first be denatured and then renatured. This can be accomplished by solubilizing the bacterially produced proteins in a chaotropic agent such as guanidine HCl and reducing all the cysteine residues with a reducing agent such as beta-mercaptoethanol. The polypeptides are then renatured, either by slow dialysis or by gel filtration. U.S. Pat. No. 4,511,503.

Detection of the expressed antigen is achieved by methods known in the art as radioimmunoassays, Western blotting techniques or immunoprecipitation. Purification from *E. coli* can be achieved following procedures described in U.S. Pat. No. 4,511,503.

2. Synthesis of SABP, DABP and EBL Binding Domains in Eukaryotes

A variety of eukaryotic expression systems such as yeast, insect cell lines and mammalian cells, are known to those of skill in the art. As explained briefly below, the DABP and SABP binding domains may also be expressed in these eukaryotic systems.

a. Expression in Yeast

Synthesis of heterologous proteins in yeast is well known and described. *Methods in Yeast Genetics*, Sherman, F., et al., Cold Spring Harbor Laboratory, (1982) is a well recognized work describing the various methods available to produce the binding domains in yeast.

Examples of promoters for use in yeast include GAL1,10 (Johnson, M., and Davies, R. W., 1984, Mol. and Cell. Biol., 4:1440–1448) ADH2 (Russell, D., et al. 1983, J. Biol. Chem., 258:2674–2682), PH05 (EMBO J. 6:675–680, 1982), and MFα1 (Herskowitz, I. and Oshima, Y., 1982, in The Molecular Biology of the Yeast Saccharomyces, (eds. Strathern, J. N. Jones, E. W., and Broach, J. R., Cold Spring Harbor Lab., Cold Spring Harbor, N.Y., pp. 181–209. A multicopy plasmid with a selective marker such as Leu-2, URA-3, Trp-1, and His-3 is also desirable.

A number of yeast expression plasmids like YEp6, YEp13, YEp4 can be used as vectors. A gene of interest can be fused to any of the promoters in various yeast vectors. The above-mentioned plasmids have been fully described in the literature (Botstein, et al., 1979, Gene, 8:17–24; Broach, et al., 1979, Gene, 8:121–133).

Two procedures are used in transforming yeast cells. In one case, yeast cells are first converted into protoplasts using zymolyase, lyticase or glusulase, followed by addition of DNA and polyethylene glycol (PEG). The PEG-treated protoplasts are then regenerated in a 3% agar medium under selective conditions. Details of this procedure are given in the papers by J. D. Beggs, 1978, Nature (London), 275:104–109; and Hinnen, A., et al., 1978, Proc. Natl. Acad. Sci. USA, 75:1929–1933. The second procedure does not involve removal of the cell wall. Instead the cells are treated with lithium chloride or acetate and PEG and put on selective plates (Ito, H., et al., 1983, J. Bact., 153:163–168).

The binding domains can be isolated from yeast by lysing the cells and applying standard protein isolation techniques to the lysates. The monitoring of the purification process can be accomplished by using Western blot techniques or radio-immunoassays of other standard immunoassay techniques.

b. Expression in Mammalian and Insect Cell Cultures

Illustrative of cell cultures useful for the production of the binding domains are cells of insect or mammalian origin. Mammalian cell systems often will be in the form of monolayers of cells although mammalian cell suspensions may also be used. Illustrative examples of mammalian cell lines include VERO and HeLa cells, Chinese hamster ovary (CHO) cell lines, W138, BHK, Cos-7 or MDCK cell lines.

As indicated above, the vector, e. g., a plasmid, which is used to transform the host cell, preferably contains DNA sequences to initiate transcription and sequences to control the translation of the antigen gene sequence. These sequences are referred to as expression control sequences. When the host cell is of insect or mammalian origin illustrative expression control sequences are obtained from the SV-40 promoter (Science, 222:524–527, 1983), the CMV I.E. Promoter (Proc. Natl. Acad. Sci. 81:659–663, 1984) or the metallothionein promoter (Nature 296:39–42, 1982). The cloning vector containing the expression control sequences is cleaved using restriction enzymes and adjusted in size as necessary or desirable and ligated with DNA coding for the SABP or DABP polypeptides by means well known in the art.

As with yeast, when higher animal host cells are employed, polyadenlyation or transcription terminator sequences from known mammalian genes need to be incorporated into the vector. An example of a terminator sequence is the polyadenlyation sequence from the bovine growth hormone gene. Sequences for accurate splicing of the transcript may also be included. An example of a splicing sequence is the VPl intron from SV40 (Sprague, J. et al., 1983, J. Virol. 45: 773–781).

Additionally, gene sequences to control replication in the host cell may be incorporated into the vector such as those found in bovine papilloma virus type-vectors. Saveria-Campo, M., 1985, "Bovine Papilloma virus DNA a Eukaryotic Cloning Vector" in DNA Cloning Vol. II a Practical Approach Ed. D. M. Glover, IRL Press, Arlington, Va. pp. 213–238.

The host cells are competent or rendered competent for transformation by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation and microinjection of the DNA directly into the cells.

The transformed cells are cultured by means well known in the art. Biochemical Methods in Cell Culture and Virology, Kuchler, R. J., Dowden, Hutchinson and Ross, Inc., (1977). The expressed DABP and SABP binding domain polypeptides are isolated from cells grown as suspensions or as monolayers. The latter are recovered by well known mechanical, chemical or enzymatic means.

c. Expression in recombinant vaccinia virus-or adenovirus-infected cells

In addition to use in recombinant expression systems, the isolated binding domain DNA sequences can also be used to transform viruses that transfect host cells in the patient. Live attenuated viruses, such as vaccinia or adenovirus, are convenient alternatives for vaccines because they are inexpensive to produce and are easily transported and administered. Vaccinia vectors and methods useful in immunization protocols are described, for example, in U.S. Pat. No. 4,722,848, incorporated herein by reference.

Suitable viruses for use in the present invention include, but are not limited to, pox viruses, such as canarypox and cowpox viruses, and vaccinia viruses, alpha viruses, adenoviruses, and other animal viruses. The recombinant viruses can be produced by methods well known in the art, for example, using homologous recombination or ligating two plasmids. A recombinant canarypox or cowpox virus can be made, for example, by inserting the DNA's encoding the DABP and SABP binding domain polypeptides into plasmids so that they are flanked by viral sequences on both sides. The DNA's encoding the binding domains are then inserted into the virus genome through homologous recombination.

A recombinant adenovirus can be produced, for example, by ligating together two plasmids each containing about 50% of the viral sequence and the DNA sequence encoding erythrocyte binding domain polypeptide. Recombinant RNA viruses such as the alpha virus can be made via a cDNA intermediate using methods known in the art.

In the case of vaccinia virus (for example, strain WR), the DNA sequence encoding the binding domains can be inserted in the genome by a number of methods including homologous recombination using a transfer vector, pTKgpt-OFIS as described in Kaslow, et al., *Science* 252:1310–1313 (1991), which is incorporated herein by reference.

Alternately the DNA encoding the SABP and DABP binding domains may be inserted into another plasmid designed for producing recombinant vaccinia, such as pGS62, Langford, C. L., et al., 1986, *Mol. Cell. Biol.* 6:3191–3199. This plasmid consists of a cloning site for insertion of foreign genes, the P7.5 promoter of vaccinia to direct synthesis of the inserted gene, and the vaccinia TK gene flanking both ends of the foreign gene.

Confirmation of production of recombinant virus can be achieved by DNA hybridization using cDNA encoding the DABP and SABP binding domain polypeptides and by immunodetection techniques using antibodies specific for the expressed binding domain polypeptides. Virus stocks may be prepared by infection of cells such as HELA S3 spinner cells and harvesting of virus progeny.

The recombinant virus of the present invention can be used to induce anti-SABP and anti-DABP binding domain antibodies in mammals, such as mice or humans. In addition, the recombinant virus can be used to produce the SABP and DABP binding domains by infecting host cells in vitro, which in turn express the polypeptide (see section on expression of SABP and DABP binding domains in eukaryotic cells, above).

The present invention also relates to host cells infected with the recombinant virus. The host cells of the present invention are preferably mammalian, such as BSC-1 cells. Host cells infected with the recombinant virus express the DABP and SABP binding domains on their cell surfaces. In addition, membrane extracts of the infected cells induce protective antibodies when used to inoculate or boost previously inoculated mammals.

D. Purification of the SABP, DABP and EBL Binding Domain Polypeptides

The binding domain polypeptides produced by recombinant DNA technology may be purified by standard techniques well known to those of skill in the art. Recombinantly produced binding domain polypeptides can be directly expressed or expressed as a fusion protein. The protein is then purified by a combination of cell lysis (e. g., sonication) and affinity chromatography. For fusion products, subsequent digestion of the fusion protein with an appropriate proteolytic enzyme release the desired SABP and DABP binding domains.

The polypeptides of this invention may be purified to substantial purity by standard techniques well known in the art, including selective precipitation with such substances as ammonium sulfate, column chromatography, immunopurification methods, and others. See, for instance, R. Scopes, *Protein Purification: Principles and Practice*, Springer-Verlag: New York (1982), incorporated herein by reference.

E. Production of Binding Domains by protein chemistry techniques

The polypeptides of the invention can be synthetically prepared in a wide variety of ways. For instance polypeptides of relatively short size, can be synthesized in solution or on a solid support in accordance with conventional techniques. Various automatic synthesizers are commercially available and can be used in accordance with known protocols. See, for example, Stewart and Young, *Solid Phase Peptide Synthesis*, 2d. ed., Pierce Chemical Co. (1984).

Alternatively, purified and isolated SABP, DABP or EBL family proteins may be treated with proteolytic enzymes in order to produce the binding domain polypeptides. For example, recombinant DABP and SABP proteins may be used for this purpose. The DABP and SABP protein sequence may then be analyzed to select proteolytic enzymes to be used to generate polypeptides containing desired regions of the DABP and SABP binding domain. The desired polypeptides are then purified by using standard techniques for protein and peptide purification. For a review of standard techniques see, *Methods in Enzymology*, "Guide to Protein Purification", M. Deutscher, ed. Vol. 182 (1990), pages 619–626, which is incorporated herein by reference.

F. Modification of nucleic acid and polypeptide sequences

The nucleotide sequences used to transfect the host cells used for production of recombinant binding domain polypeptides can be modified according to standard techniques to yield binding domain polypeptides, with a variety of desired properties. The binding domain polypeptides of the present invention can be readily designed and manufactured utilizing various recombinant DNA techniques well known to those skilled in the art. For example, the binding domain polypeptides can vary from the naturally-occurring sequence at the primary structure level by amino acid insertions, substitutions, deletions, and the like. These modifications can be used in a number of combinations to produce the final modified protein chain.

The amino acid sequence variants can be prepared with various objectives in mind, including facilitating purification and preparation of the recombinant polypeptides. The modified polypeptides are also useful for modifying plasma half-life, improving therapeutic efficacy, and lessening the severity or occurrence of side effects during therapeutic use. The amino acid sequence variants are usually predetermined variants not found in nature but exhibit the same immunogenic activity as naturally occurring polypeptides. For instance, polypeptide fragments comprising only a portion (usually at least about 60–80%, typically 90–95%) of the primary structure may be produced. For use as vaccines, polypeptide fragments are typically preferred so long as at least one epitope capable of eliciting production of blocking antibodies remains.

In general, modifications of the sequences encoding the binding domain polypeptides may be readily accomplished by a variety of well-known techniques, such as site-directed mutagenesis (see, Giliman and Smith, *Gene* 8:81–97 (1979) and Roberts, S. et al., *Nature* 328:731–734 (1987)). One of ordinary skill will appreciate that the effect of many mutations is difficult to predict. Thus, most modifications are evaluated by routine screening in a suitable assay for the desired characteristic. For instance, changes in the immunological character of the polypeptide can be detected by an appropriate competitive binding assay. Modifications of other properties such as redox or thermal stability, hydrophobicity, susceptibility to proteolysis, or the tendency to aggregate are all assayed according to standard techniques.

G. Diagnostic and Screening Assays

The polypeptides of the invention can be used in diagnostic applications for the detection of merozoites in a biological sample. The presence of parasites can be detected using several well recognized specific binding assays based on immunological results. (See U.S. Pat. Nos. 4,366,241; 4,376,110; 4,517,288; and 4,837,168, which are hereby incorporated by reference.) For instance, labeled monoclonal antibodies to polypeptides of the invention can be used to detect merozoites in a biological sample. Alternatively, labelled polypeptides of the invention can be used to detect the presence of antibodies to SABP or DABP in a biological sample. For a review of the general procedures in diagnostic immunoassays, see also *Basic and Clinical Immunology* 7th Edition (D. Stites and A. Terr ed.) 1991, which is hereby incorporated by reference.

In addition, modified polypeptides, antibodies or other compounds capable of inhibiting the interaction between SABP or DABP and erythrocytes can be assayed for biological activity. For instance, polypeptides can be recombinantly expressed on the surface of cells and the ability of the cells to bind erythrocytes can be measured as described below. Alternatively, peptides or antibodies can tested for the ability to inhibit binding between erythrocytes and merozoites or SABP and DABP.

Cell-free assays can also be used to measure binding of DABP or SABP polypeptides to isolated Duffy antigen or glycophorin polypeptides. For instance, the erythrocyte proteins can be immobilized on a solid surface and binding of labelled SABP or DABP polypeptides can be measured.

Many assay formats employ labelled assay components. The labelling systems can be in a variety of forms. The label may be coupled directly or indirectly to the desired component of the assay according to methods well known in the art. A wide variety of labels may be used. The component may be labelled by any one of several methods. The most common method of detection is the use of autoradiography with $^3H$, $^{125}I$, $^{35}S$, $^{14}C$, or $^{32}p$ labelled compounds or the like. Non-radioactive labels include ligands which bind to labelled antibodies, fluorophores, chemiluminescent agents, enzymes, and antibodies which can serve as specific binding pair members for a labelled ligand. The choice of label depends on sensitivity required, ease of conjugation with the compound, stability requirements, and available instrumentation.

In addition, the polypeptides of the invention can be assayed using animal models, well known to those of skill in the art. For *P. falciparum* the in vivo models include Aotus sp. monkeys or chimpanzees; for *P. vivax* the in vivo models include Saimiri monkeys.

H. Pharmaceutical compositions complising binding domain polypeptides

The polypeptides of the invention are useful in therapeutic and prophylactic applications for the treatment of malaria. Pharmaceutical compositions of the invention are suitable for use in a variety of drug delivery systems. Suitable formulations for use in the present invention are found in *Remington's Pharmaceutical Sciences*, Mack Publishing Company, Philadelphia, Pa., 17th ed. (1985), which is incorporated herein by reference. For a brief review of methods for drug delivery, see, Langer, *Science* 249:1 527–1533 (1990), which is incorporated herein by reference.

The polypeptides of the present invention can be used in pharmaceutical and vaccine compositions that are useful for administration to mammals, particularly humans. The polypeptides can be administered together in certain circumstances, e.g. where infection by both *P. falciparum* and *P. vivax* is likely. Thus, a single pharmaceutical composition can be used for the treatment or prophylaxis of malaria caused by both parasites.

The compositions are suitable for single administrations or a series of administrations. When given as a series, inoculations subsequent to the initial administration are given to boost the immune response and are typically referred to as booster inoculations.

The pharmaceutical compositions of the invention are intended for parenteral, topical, oral or local administration. Preferably, the pharmaceutical compositions are administered parenterally, e.g., intravenously, subcutaneously, intradermally, or intramuscularly. Thus, the invention provides compositions for parenteral administration that comprise a solution of the agents described above dissolved or suspended in an acceptable carrier, preferably an aqueous carrier. A variety of aqueous carriers may be used, e.g., water, buffered water, 0.4% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient and more preferably at a concentration of 25%–75%.

For aerosol administration, the polypeptides are preferably supplied in finely divided form along with a surfactant and propellant. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included, as desired, as with, e.g., lecithin for intranasal delivery.

In certain embodiments patients with malaria may be treated with SABP or DABP polypeptides or other specific blocking agents (e.g. monoclonal antibodies) that prevent binding of Plasmodium merozoites and schizonts to the erythrocyte surface.

The amount administered to the patient will vary depending upon what is being administered, the state of the patient and the manner of administration. In therapeutic applications, compositions are administered to a patient already suffering from malaria in an amount sufficient to inhibit spread of the parasite through erythrocytes and thus cure or at least partially arrest the symptoms of the disease and its complications. An amount adequate to accomplish this is defined as "therapeutically effective dose." Amounts effective for this use will depend on the severity of the disease and the weight and general state of the patient. But will generally be in the range of about 1 mg to about 5 am per day, preferably about 100 mg per day, for a 70 kg patient.

Alternatively, the polypeptides of the invention can be used prophylactically as vaccines. The vaccines of the invention contain as an active ingredient an immunogenically effective amount of the binding domain polypeptide or of a recombinant virus as described herein. The immune response may include the generation of antibodies; activation of cytotoxic T lymphocytes (CTL) against cells presenting peptides derived from the peptides encoded by the SABP, DABP or EBL sequences of the present invention, or other mechanisms well known in the art. See e.g. Paul *Fundamental Immunology Second Edition* published by Raven press New York (incorporated herein by reference) for a description of immune response. Useful carriers are well known in the art, and include, for example, thyroglobulin, albumins such as human serum albumin, tetanus toxoid, polyamino acids such as poly(D-lysine:D-glutamic acid), influenza, hepatitis B virus core protein, hepatitis B virus recombinant vaccine. The vaccines can also contain a physiologically tolerable (acceptable) diluent such as water, phosphate buffered saline, or saline, and further typically include an adjuvant. Adjuvants such as incomplete Freund's adjuvant, aluminum phosphate, aluminum hydroxide, or alum are materials well known in the art.

The DNA or RNA encoding the SABP or DABP binding domains and the EBL gene family motifs may be introduced into patients to obtain an immune response to the polypeptides which the nucleic acid encodes. Wolff et. al., *Science* 247: 1465–1468 (1990) which is incorporated herein by reference describes the use of nucleic acids to produce expression of the genes which the nucleic acids encode.

Vaccine compositions containing the polypeptides, nucleic acids or viruses of the invention are administered to a patient to elicit a protective immune response against the polypeptide. A "protective immune response" is one which prevents or inhibits the spread of the parasite through erythrocytes and thus at least partially prevent the symptoms of the disease and its complications. An amount sufficient to accomplish this is defined as an "immunogenically effective dose." Amounts effective for this use will depend on the composition, the manner of administration, the weight and general state of health of the patient, and the judgment of the prescribing physician. For peptide compositions, the general range for the initial immunization (that is for therapeutic or prophylactic administration) is from about 100 μg to about 1 gm of peptide for a 70 kg patient, followed by boosting dosages of from about 100 μg to about 1 gm of the polypeptide pursuant to a boosting regimen over weeks to months depending upon the patient's response and condition e.g. by measuring levels of parasite in the patient's blood. For nucleic acids, typically 30–1000 μg of nucleic acid is injected into a 70 kg patient, more typically about 50–150 μg of nucleic acid is injected into a 70 kg patient followed by boosting doses as appropriate.

The following example is offered by way of illustration, not by way of limitation.

EXAMPLE

Identification of the amino-terminal, cysteine-rich region of SABP and DABP as binding domains for erythrocytes 1. Expression of the SABP binding domain polypeptide on the surface of Cos cells.

To demonstrate that the amino-terminal, cysteine-rich region of the SABP protein is the sialic acid binding region, this region of the protein was expressed on the surface of mammalian Cos cells in vitro. This DNA sequence is from position 1 to position 1848 of the SABP DNA sequence (SEQ ID NO 3). Polymerase chain reaction technology (PCR) was used to amplify this region of the SABP DNA directly from the cloned gene.

Sequences corresponding to restriction endonuclease sites for PvuII or ApaI were incorporated into the oligonucleotide sequence of the probes used in PCR amplification in order to facilitate insertion of the PCR-amplified regions into the pRE4 vector (see below). The specific oligonucleotides, 5'-ATCGATCAGCTGGGAAGAAATACTTCATCT-3' (SEQ ID NO: 34) and 5'-ATCGATGGGCCCCGAAGTTTGTTCATTATT-3' (SEQ ID NO: 35) were synthesized. These oligonucleotides were used as primers to PCR-amplify the region of the DNA sequence encoding the cysteine-rich amino terminal region of the SABP protein.

PCR conditions were based on the standard described in Saiki, et al., Science 239: 487–491 (1988). Template DNA was provided from cloned fragments of the gene encoding SABP which had been spliced and re-cloned as a single open-reading frame piece.

The vector, pRE4, used for expression in Cos cells is shown in FIG. 1. The vector has an SV40 origin of replication, an ampicillin resistance marker and the Herpes simplex virus glycoprotein D gene (HSV glyd) cloned downstream of the Rous sarcoma virus long terminal repeats (RSV LTR). Part of the extracellular domain of the HSV glyd gene was excised using the PvuII and ApaI sites in HSV glyd.

As described above, the PCR oligonucleotide primers contained the PvuII or ApaI restriction sites. The PCR-amplified DNA fragments obtained above were digested with the restriction enzymes PvuII and ApaI and cloned into the PvuII and ApaI sites of the vector pRE4. These constructs were designed to express regions of the SABP protein as chimeric proteins with the signal sequence of HSV glyd at the N-terminal end and the transmembrane and cytoplasmic domain of HSV glyd at the C-terminal end. The signal sequence of HSV glyd targets these chimeric proteins to the surface of Cos cells and the transmembrane segment of HSV glyd anchors these chimeric proteins to the Cos cell surface.

Mammalian Cos cells were transfected with the pRE4 constructs containing the PCR-amplified SABP DNA regions, by calcium phosphate precipitation according to standard techniques.

2. Expression of the DABP binding domain polypeptide on the surface of Cos cells.

To demonstrate that the amino-terminal, cysteine-rich region of the DABP protein is the binding domain, this region was expressed on the surface of Cos cells. This region of the DNA sequence from position 1-975 was first PCR-amplified (SEQ ID NO 1).

Sequences corresponding to restriction endonuclease sites for PvuII or ApaI were incorporated into the oligonucleotide probes used for PCR amplification in order to facilitate subsequent insertion of the amplified DNA into the pRE4 vector, as described above. The oligonucleotides, 5'-TCTCGTCAGCTGACGATCTCTAGTGCTATT-3' (SEQ ID NO: 36) and 5'-ACGAGTGGGCCCTGTCACAACTTCCTGAGT-3' (SEQ ID NO: 37) were synthesized. These oligonucleotides were used as primers to amplify the region of the DABP DNA sequence encoding the cysteine-rich, amino-terminal region of the DABP protein directly from the cloned DABP gene, using the same conditions described above.

The same pRE4 vector described above in the section on expression of SABP regions in Cos cells was also used as a vector for the DABP DNA regions.

3. Binding studies with erythrocytes.

To demonstrate their ability to bind human erythrocytes, the transfected Cos cells expressing binding domains from DABP and SABP were incubated with erythrocytes for two hours at 37° C. in culture media (DMEM/10% FBS). The non-adherent erythrocytes were removed with five washes of phosphate-buffered saline and the bound erythrocytes were observed by light microscopy. Cos cells expressing the amino terminal, cysteine-rich SABP polypeptides on their surface bound untreated human erythrocytes, but did not bind neuraminidase treated erythrocytes, that is, erythrocytes which lack sialic acid residues on their surface (data not shown). Cos cells expressing other regions of the SABP protein on their surface did not bind human erythrocytes (data not shown). These results identified the amino-terminal, cysteine-rich region of SABP as the erythrocyte binding domain and indicated that the binding of Cos cells expressing these regions to human erythrocytes is specific. Furthermore, the binding of the expressed region to erythrocytes is identical to the binding pattern seen for the authentic SABP-175 molecule upon binding to erythrocytes.

Similarly, Cos cells expressing the amino-terminal cysteine-rich region of DABP on their surface bound Duffy-positive human erythrocytes, but did not bind Duffy-negative human erythrocytes, that is erythrocytes which lack the Duffy blood group antigen (data not shown). Cos cells expressing other regions of the DABP protein on their surface did not bind human erythrocytes (data not shown). These results identified the amino-terminal cysteine rich region of DABP as the erythrocyte binding domain and indicated that the binding of the Cos cells was specific.

What is claimed is:

1. A composition comprising an isolated cysteine-rich binding domain polypeptide derived from the *P. falciparum* 175 kDa sialic acid binding protein of SEQ ID NO:4, wherein said cysteine-rich binding domain polypeptide consists of an amino acid sequence of about 50 to about 616 residues comprising cysteine residues that are in substantially similar relative positions as positions of cysteine residues in an amino acid sequence of a *P. vivax* Duffy Antigen binding protein of SEQ ID NO: 2.

2. The composition of claim 1, wherein the cysteine-rich binding domain polypeptide comprises between about 200 and about 600 amino acid residues.

3. The composition of claim 1, wherein the cysteine-rich binding domain polypeptide consists of an amino acid sequence comprising residues 158 to 739 of the amino acid sequence of SEQ ID NO. 4.

4. The composition of claim 1, wherein the cysteine-rich binding domain polypeptide is recombinantly produced.

5. A pharmaceutical composition comprising a pharmaceutically acceptable carrier and an isolated cysteine-rich binding domain polypeptide derived from the *P. falciparum* 175 kDa sialic acid binding protein of SEQ ID NO: 4, wherein said cysteine-rich binding domain polypeptide consists of an amino acid sequence of about 50 to about 616 residues comprising cysteine residues that are in substantially similar relative positions as positions of cysteine residues in an amino acid sequence of a *P. vivax* Duffy Antigen binding protein of SEQ ID NO: 2, in an amount sufficient to induce a partial protective immune response that reduces the severity of infection by *Plasmodium falciparum* merozoites in an organism.

6. The composition of claim 1, wherein the cysteine-rich binding domain polypeptide consists of an amino acid sequence comprising residues 158 to 427 of SEQ ID NO:4.

7. The composition of claim 1, wherein the cysteine-rich binding domain polypeptide consists of an amino acid sequence comprising residues 462 to 739 of SEQ ID NO:4.

8. The composition of claim 7, wherein said cysteine-rich binding domain polypeptide comprises a sequence of amino acid residues in which at least 70% of cysteine residues conserved in the *P. falciparum* sialic acid binding protein of SEQ ID NO:4 and the *P. vivax* Duffy antigen binding protein of SEQ ID NO:2 are present.

9. A method of inducing a partially protective immune response to *Plasmodium falciparum* merozoites in a patient, the method comprising administration to the patient of an immunologically effective amount of a pharmaceutical composition comprising a pharmaceutically acceptable carrier and an isolated cysteine-rich binding domain polypeptide derived from a *P. falciparum* 175 kDa sialic acid binding protein of SEQ ID NO:4 wherein the cysteine-rich binding domain polypeptide consists of an amino acid sequence of about 50 to about 616 residues comprising cysteine residues that are in substantially similar relative positions as positions of cysteine residues in an amino acid sequence of a Duffy Antigen binding protein of *P. vivax* of SEQ ID NO:2, wherein the partially protective immune response reduces the severity of infection by *P. falciparum*.

10. The method of claim 9, wherein the patient is a human.

11. A method of inducing a partially protective immune response to *Plasmodium vivax* merozoites in a patient, the method comprising administration to the patient of an immunologically effective amount of a pharmaceutical composition comprising a pharmaceutically acceptable carrier and an isolated cysteine-rich binding domain polypeptide derived from a *P. vivax* Duffy Antigen binding protein of SEQ ID NO:2, wherein the *P. vivax* cysteine-rich binding domain polypeptide consists of an amino acid sequence of about 50 to 325 residues comprising cysteine residues in substantially similar relative positions as positions of cysteine residues present in a *P. falciparum* 175 kDa sialic acid binding protein of SEQ ID NO: 4, and wherein the partially protective immune response reduces the severity of infection by *P. vivax*.

12. A method of inducing a partially protective immune response to *Plasmodium falciparum* merozoites and *Plasmodium vivax* merozoites in a patient, the method comprising administration to the patient of an immunologically effective amount of a pharmaceutical composition comprising a pharmaceutically acceptable carrier and a combination of an isolated first cysteine-rich binding domain polypeptide derived from the *P. falciparum* 175 kDa sialic acid binding protein of SEQ ID NO:4, wherein the first cysteine-rich binding domain polypeptide consists of an amino acid sequence of about 50 to about 616 residues, and an isolated second cysteine-rich binding domain polypeptide derived from *P. vivax* Duffy Antigen binding protein of SEQ ID NO:2, wherein the second cysteine-rich binding domain polypeptide consists of an amino acid sequence of about 50 to about 325 residues, and wherein the first cysteine-rich binding domain polypeptide comprises cysteine residues that are in substantially similar relative positions as positions of cysteine residues present in the amino acid sequence of the second cysteine-rich binding domain polypeptide, and wherein the partially protective immune response reduces the severity of infection by *P. falciparum* and *P. vivax*.

* * * * *